(12) United States Patent
Otsubo et al.

(10) Patent No.: US 9,453,021 B2
(45) Date of Patent: Sep. 27, 2016

(54) PYRIMIDODIAZEPINONE COMPOUND

(75) Inventors: Nobumasa Otsubo, Mishima (JP); Shuko Okazaki, Tokyo (JP); Yukihito Tsukumo, Shizuoka (JP); Kyoichiro Iida, Kanagawa (JP); Masayoshi Nakoji, Shizuoka (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 0 days.

(21) Appl. No.: 14/116,702

(22) PCT Filed: May 10, 2012

(86) PCT No.: PCT/JP2012/061957
§ 371 (c)(1),
(2), (4) Date: Feb. 4, 2014

(87) PCT Pub. No.: WO2012/153796
PCT Pub. Date: Nov. 15, 2012

(65) Prior Publication Data
US 2014/0171422 A1    Jun. 19, 2014

(30) Foreign Application Priority Data
May 10, 2011    (JP) .............................. 2011-105083

(51) Int. Cl.
| | | |
|---|---|---|
| A61K 31/551 | (2006.01) | |
| C07D 487/14 | (2006.01) | |
| A61K 31/5517 | (2006.01) | |
| C07D 519/00 | (2006.01) | |
| C07D 471/04 | (2006.01) | |
| C07D 495/04 | (2006.01) | |

(52) U.S. Cl.
CPC ......... *C07D 487/14* (2013.01); *A61K 31/5517* (2013.01); *C07D 471/04* (2013.01); *C07D 495/04* (2013.01); *C07D 519/00* (2013.01)

(58) Field of Classification Search
CPC .......................... A61K 31/551; C07D 487/14
USPC ........................................... 514/220; 540/496
See application file for complete search history.

(56) References Cited

U.S. PATENT DOCUMENTS

| 4,761,411 A | 8/1988 | Glamkowski et al. |
|---|---|---|
| 2007/0207998 A1 | 9/2007 | Schrattenholz |
| 2010/0190775 A1 | 7/2010 | Otsubo et al. |
| 2010/0247688 A1 | 9/2010 | Pfeifer et al. |

FOREIGN PATENT DOCUMENTS

| EP | 0 518 484 | 12/1992 |
|---|---|---|
| JP | 59-219285 | 12/1984 |
| JP | 06-239750 | 8/1994 |
| JP | 2008-506661 | 3/2008 |
| JP | 2010-531854 | 9/2010 |
| WO | WO-2006/051410 | 5/2006 |
| WO | WO-2007/117180 | 10/2007 |
| WO | WO-2008/149834 | 12/2008 |
| WO | WO-2009/032754 | 3/2009 |

OTHER PUBLICATIONS

Simmons et al., "Update on diabetic neuropathy", Current Opinion Neurology, vol. 15, pp. 595-603 (2002).
Ziegler, MD, "Painful Diabetic Neuropathy", Diabetes Care, vol. 32, Supplement 2, pp. S414-S419 (2009).
Dooley et al., "$Ca^{2+}$ channel $\alpha_2\delta$ ligands: novel modulators of neurotransmission", Trends in Pharmacological Sciences, vol. 28, No. 2, pp. 75-82 (2007).
Gee et al., "The Novel Anticonvulsant Drug, Gabapentin (Neurontin), Binds to the $\alpha_2\delta$ Submit of a Calcium Channel*", The Journal of Biological Chemistry, vol. 271, No. 10, pp. 5768-5776 (1996).
Gong et al., "Tissue-specific Expression and Gabapentin-Binding Properties of Calcium Channel $\alpha 2\delta$ Subunit Subtypes", J. Membrane Biol., vol. 184, pp. 35-3 (2001).
International Search Report and Written Opinion mailed Jul. 17, 2012, in corresponding PCT application No. PCT/JP2012/061957.

*Primary Examiner* — Brenda Coleman
(74) *Attorney, Agent, or Firm* — Mintz Levin Cohn Ferris Glovsky and Popeo, P.C.; David G. Conlin; Christopher R. Cowles

(57) ABSTRACT

Provided are a compound represented by general formula (I), or the pharmaceutically acceptable salt thereof,

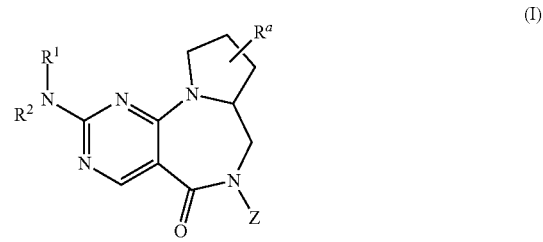

(wherein $R^a$ represents a hydrogen atom or the like, $R^1$ and $R^2$ may be the same or different, and each represents a hydrogen atom, optionally substituted lower alkyl or cycloalkyl, or $R^1$ and $R^2$ are combined together with the adjacent nitrogen atom thereto to form nitrogen-containing heterocyclic group, and Z represents a bicyclic heterocyclic group in which optionally substituted two six-membered rings are fused to each other, or the like) and the like.

13 Claims, No Drawings

PYRIMIDODIAZEPINONE COMPOUND

CROSS-REFERENCE TO RELATED APPLICATIONS

This application is the U.S. national phase application pursuant to 35 U.S.C. §371 of PCT International Patent Application No. PCT/JP2012/061957, filed May 10, 2012, which claims priority to Japanese Patent Application No. 2011-105083, filed May 10, 2011.

TECHNICAL FIELD

The present invention relates to a compound or a pharmaceutically acceptable salt thereof useful as a therapeutic and/or preventive agent for, for example, pain (specifically, diabetic pain, and the like).

BACKGROUND ART

Diabetic neuropathy has the highest incidence among all diabetes complications, and greatly affects the quality of life (QOL) of diabetes patients. Although various types of diabetic neuropathies have been identified, the primary goal of diabetic neuropathy treatment is to relieve pain [Current Opinion Neurology, 2002, Vol. 15, p. 595-603]. To date, drugs such as capsaicin ointments, antidepressants, anticonvulsants, and opioids have been used for diabetic pain [Diabetes Care, 2009, Vol. 32, p. 414-419]. However, because of the diversity of the onset mechanism, the therapeutic effects are unsatisfactory, and development of new drugs is desired.

Meanwhile, it is reported that some γ-aminobutyric acid (GABA) derivatives such as gabapentin and pregabalin are effective against central nervous system (CNS) diseases, perceptual disorders, and the like, and these are known as antiepileptic drugs and analgesics [TRENDS in Pharmacological Science, 2007, Vol. 28, p. 75-82]. Because gabapentin and pregabalin have high affinity for $\alpha_2\delta$ protein, it is suggested that the effect on $\alpha_2\delta$ protein plays an important role in the antiepileptic, antalgic, and other pharmacological effects of these drugs [The Journal of Biological Chemistry, 1996, Vol. 271, p. 5768-5776, Journal of Membrane Biology, 2001, Vol. 184, p. 35-43].

Therefore, compounds having high affinity for $\alpha_2\delta$ protein ($\alpha_2\delta$ ligands) are considered to be useful as therapeutic and/or preventive agents for CNS diseases, perceptual disorders, and the like. Specifically, $\alpha_2\delta$ ligands are considered useful as therapeutic and/or preventive agents for diseases such as pain (for example, neuropathic pain, trigeminal neuralgia, diabetic pain, postherpetic neuralgia, phantom pain, neuropathic lower back pain, HIV-related pain, fibromyalgia syndrome, cancer pain, inflammatory pain, acute pain, chronic pain, postoperative pain, pain after teeth extraction, chronic musculoskeletal pain, nociceptive pain, psychogenic pain, menstrual pain, and the like), migraine, pruritus, lower urinary tract symptoms, irritable bowel syndrome, epilepsy, restless legs syndrome, hot flash, mood disorder, sleep disorder, and the like.

Meanwhile, a pyrimidodiazepinone derivative having an affinity for $\alpha_2\delta$ protein and useful as a therapeutic agent for pain, pruritus, and the like is known. For instance, the compound represented by the following formula (1-146) and the like is known (see Patent Document 1).

[Chemical Formula 1]

(1-146)

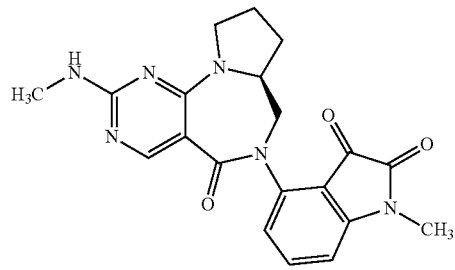

PRIOR ART DOCUMENT LIST

Patent Document

Patent Document 1: WO2008/149834

SUMMARY OF THE INVENTION

Problems to be Solved by the Invention

An object of the present invention is to provide a compound or a pharmaceutically acceptable salt thereof useful as a therapeutic and/or preventive agent for, for example, pain (specifically, diabetic pain, and the like).

Means for Solving the Problems

The present invention is related to the following (1) to (28).

(1) A compound represented by general formula (I), or a pharmaceutically acceptable salt thereof,

[Chemical Formula 2]

(I)

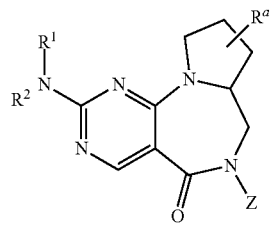

(wherein $R^a$ represents a hydrogen atom, halogen, hydroxy, or lower alkoxy, $R^1$ and $R^2$ may be the same or different, and each represents a hydrogen atom, optionally substituted lower alkyl or cycloalkyl, or $R^1$ and $R^2$ are combined together with the adjacent nitrogen atom thereto to form a nitrogen-containing heterocyclic group, and Z represents a bicyclic heterocyclic group in which optionally substituted two six-membered rings are fused to each other, or a bicyclic heterocyclic group in which an optionally substituted five-membered heterocyclic ring and an optionally substituted six-membered heterocyclic ring are fused to each other).

(2) The compound or the pharmaceutically acceptable salt thereof according to (1), wherein $R^a$ is a hydrogen atom.

(3) The compound or the pharmaceutically acceptable salt thereof according to (1) or (2), wherein Z is a bicyclic heterocyclic group in which optionally substituted two six-membered rings are fused to each other.

(4) The compound or the pharmaceutically acceptable salt thereof according to (1) or (2), wherein Z is a bicyclic heterocyclic group in which an optionally substituted five-membered heterocyclic ring and an optionally substituted six-membered heterocyclic ring are fused to each other.

(5) The compound or the pharmaceutically acceptable salt thereof according to any one of (1) to (3), wherein the bicyclic heterocyclic ring moiety of the bicyclic heterocyclic group in which two six-membered rings are fused to each other is a heterocyclic ring represented by any one of the following formulae (A) to (Q).

[Chemical Formula 3]

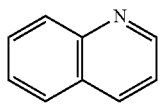
(A)

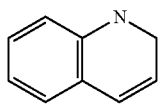
(B)

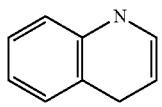
(C)

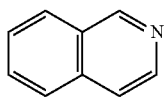
(D)

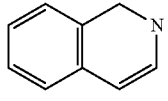
(E)

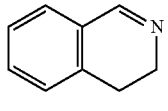
(F)

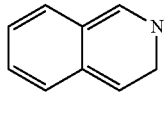
(G)

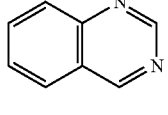
(H)

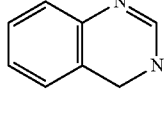
(J)

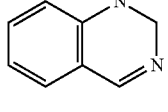
(K)

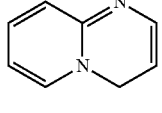
(L)

-continued

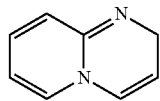
(M)

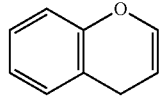
(N)

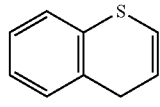
(O)

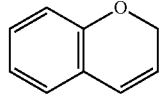
(P)

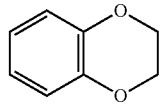
(Q)

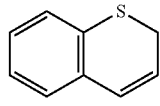
(R)

(6) The compound or the pharmaceutically acceptable salt thereof according to any one of (1) to (3), wherein the bicyclic heterocyclic ring moiety of the bicyclic heterocyclic group in which two six-membered rings are fused to each other is a heterocyclic ring represented by the following formula (A), (B), (D), (E), (J), or (L).

[Chemical Formula 4]

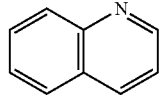
(A)

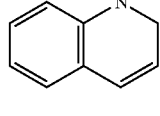
(B)

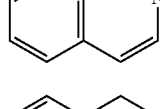
(D)

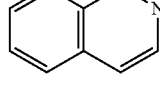
(E)

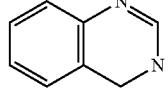
(J)

(7) The compound or the pharmaceutically acceptable salt thereof according to any one of (1) to (3), wherein the bicyclic heterocyclic ring moiety of the bicyclic heterocyclic group in which two six-membered rings are fused to each other is a heterocyclic ring represented by the following formula (E), (J), or (L).

[Chemical Formula 5]

(E)

(J)

(L)

(8) The compound or the pharmaceutically acceptable salt thereof according to any one of (1) to (3), wherein the bicyclic heterocyclic group in which two six-membered rings are fused to each other is a group represented by the following formula (A1), (A2), (B1), (B2), (D1), (D2), (E1), (E2), (J1), (J2), (L1), or (L2).

[Chemical Formula 6]

(A1)

(A2)

(B1)

(B2)

(D1)

(D2)

(E1)

(E2)

(J1)

(J2)

(L1)

(L2)

(9) The compound or the pharmaceutically acceptable salt thereof according to any one of (1) to (3), wherein the bicyclic heterocyclic group in which optionally substituted two six-membered rings are fused to each other is a group represented by the following formula (L1a), (J1a), (J2a), or (E1a),

[Chemical Formula 7]

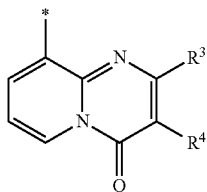
(L1a)

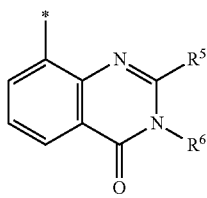
(J1a)

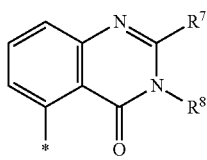
(J2a)

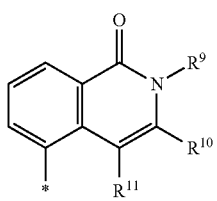
(E1a)

(wherein $R^3$, $R^4$, $R^5$, $R^6$, $R^7$, $R^8$, $R^9$, $R^{10}$, and $R^{11}$ may be the same or different, and each represents a hydrogen atom, or optionally substituted lower alkyl).

(10) The compound or the pharmaceutically acceptable salt thereof according to any one of (1) to (3), wherein the bicyclic heterocyclic group in which optionally substituted two six-membered rings are fused to each other is a group represented by the following formula (L1a) or (J1a),

[Chemical Formula 8]

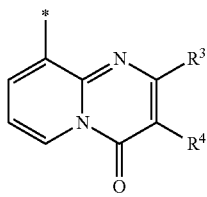
(L1a)

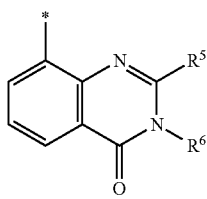
(J1a)

(wherein $R^3$, $R^5$, and $R^6$ have the same definitions as described above, respectively).

(11) The compound or the pharmaceutically acceptable salt thereof according to (10), wherein $R^3$, $R^4$, $R^5$, and $R^6$ may be the same or different, and each represents a hydrogen atom; methyl; ethyl; or ethyl or propyl substituted with a fluorine atom, methoxy, or dimethylamino.

(12) The compound or the pharmaceutically acceptable salt thereof according to any one of (1) to (3), wherein Z is a group represented by the following formula (L1b), (J1b), (J2b), or (E1b),

[Chemical Formula 9]

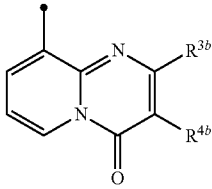
(L1b)

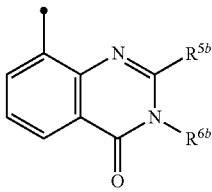
(J1b)

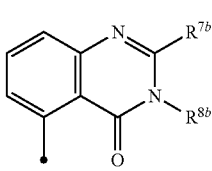
(J2b)

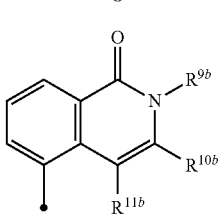
(E1b)

(wherein, $R^{3b}$, $R^{4b}$, $R^{5b}$, $R^{6b}$, $R^{7b}$, $R^{8b}$, $R^{9b}$, $R^{10b}$, and $R^{11b}$ may be the same or different, and each represents a hydrogen atom, or lower alkyl).

(13) The compound or the pharmaceutically acceptable salt thereof according to (12), wherein $R^{3b}$, $R^{4b}$, $R^{5b}$, $R^{6b}$, $R^{7b}$, $R^{8b}$, $R^{9b}$, $R^{10b}$, and $R^{11b}$ may be the same or different, and each represents a hydrogen atom, methyl, ethyl, or propyl.

(14) The compound or the pharmaceutically acceptable salt thereof according to (1), (2), or (4), wherein Z is a group represented by the following formula (S1), (T1), or (U1),

[Chemical Formula 10]

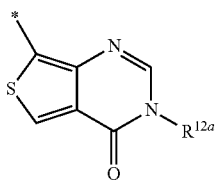
(S1)

-continued

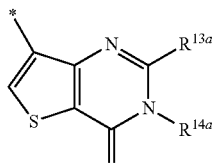
(T1)

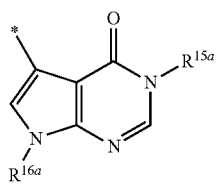
(U1)

(wherein, $R^{12a}$, $R^{13a}$, $R^{14a}$, $R^{15a}$, and $R^{16a}$ may be the same or different, and each represents a hydrogen atom, or optionally substituted lower alkyl).

(15) The compound or the pharmaceutically acceptable salt thereof according to any one of (1) to (14), wherein $R^1$ is lower alkyl or cycloalkyl, and $R^2$ is a hydrogen atom.

(16) The compound or the pharmaceutically acceptable salt thereof according to any one of (1) to (14), wherein $R^1$ is lower alkyl, and $R^2$ is a hydrogen atom.

(17) The compound or the pharmaceutically acceptable salt thereof according to any one of (1) to (14), wherein $R^1$ is methyl or ethyl, and $R^2$ is a hydrogen atom.

(18) The compound or the pharmaceutically acceptable salt thereof according to (1), wherein the compound represented by general formula (I) is any one of:
(S)-6-(2,3-dimethyl-4-oxo-4H-pyrido[1,2-a]pyrimidin-9-yl)-2-ethylamino-6,7,7a,8,9,10-hexahydro-5H-pyrimido[5,4-f]pyrrolo[1,2-a][1,4]diazepin-5-one (compound 7),
(S)-6-(2,3-dimethyl-4-oxo-4H-pyrido[1,2-a]pyrimidin-9-yl)-2-methylamino-6,7,7a,8,9,10-hexahydro-5H-pyrimido[5,4-f]pyrrolo[1,2-a][1,4]diazepin-5-one (compound 8),
(S)-6-(3-methyl-4-oxo-3,4-dihydroquinazolin-8-yl)-2-methylamino-6,7,7a,8,9,10-hexahydro-5H-pyrimido[5,4-f]pyrrolo[1,2-a][1,4]diazepin-5-one (compound 10),
(S)-2-ethylamino-6-(2,3-dimethyl-4-oxo-3,4-dihydroquinazolin-8-yl)-6,7,7a,8,9,10-hexahydro-5H-pyrimido[5,4-f]pyrrolo[1,2-a][1,4]diazepin-5-one (compound 11),
(S)-6-(3-ethyl-4-oxo-3,4-dihydroquinazolin-8-yl)-2-methylamino-6,7,7a,8,9,10-hexahydro-5H-pyrimido[5,4-f]pyrrolo[1,2-a][1,4]diazepin-5-one (compound 14),
(S)-2-ethylamino-6-(3-methyl-4-oxo-3,4-dihydroquinazolin-5-yl)-6,7,7a,8,9,10-hexahydro-5H-pyrimido[5,4-f]pyrrolo[1,2-a][1,4]diazepin-5-one (compound 15),
(S)-6-(3-(3-(dimethylamino)propyl)-4-oxo-3,4-dihydroquinazolin-8-yl)-2-(methylamino)-6,7,7a,8,9,10-hexahydro-5H-pyrimido[5,4-f]pyrrolo[1,2-a][1,4]diazepin-5-one (compound 38),
(S)-6-(3-(3-(dimethylamino)propyl)-4-oxo-3,4-dihydroquinazolin-8-yl)-2-(ethylamino)-6,7,7a,8,9,10-hexahydro-5H-pyrimido[5,4-f]pyrrolo[1,2-a][1,4]diazepin-5-one (compound 39),
(S)-2-ethylamino-6-(2-(methoxymethyl)-3-methyl-4-oxo-3,4-dihydroquinazolin-8-yl)-6,7,7a,8,9,10-hexahydro-5H-pyrimido[5,4-f]pyrrolo[1,2-a][1,4]diazepin-5-one (compound 65), and
(S)-6-(3-methyl-4-oxo-3,4-dihydroquinazolin-8-yl)-2-propylamino-6,7,7a,8,9,10-hexahydro-5H-pyrimido[5,4-f]pyrrolo[1,2-a][1,4]diazepin-5-one (compound 71).

(19) The compound or the pharmaceutically acceptable salt thereof according to (1), wherein the compound represented by general formula (I) is any one of:
(S)-7-(2-(ethylamino)-5-oxo-7a,8,9,10-tetrahydro-5H-pyrimido[5,4-f]pyrrolo[1,2-a][1,4]diazepin-6(7H)-yl)-3-methylthieno[3,4-d]pyrimidin-4(3H)-one (compound 97),
(S)-6-(3-methyl-4-oxo-4,7-dihydro-3H-pyrrolo[2,3-d]pyrimidin-5-yl)-2-(methylamino)-6,7,7a,8,9,10-hexahydro-5H-pyrimido[5,4-f]pyrrolo[1,2-a][1,4]diazepin-5-one (compound 112), and
(S)-2-(ethylamino)-6-(3-methyl-4-oxo-4,7-dihydro-3H-pyrrolo[2,3-d]pyrimidin-5-yl)-6,7,7a,8,9,10-hexahydro-5H-pyrimido[5,4-f]pyrrolo[1,2-a][1,4]diazepin-5-one (compound 113).

(20) The compound or the pharmaceutically acceptable salt thereof according to (1), wherein the compound represented by general formula (I) is any one of:
(S)-6-(2,3-dimethyl-4-oxo-4H-pyrido[1,2-a]pyrimidin-9-yl)-2-methylamino-6,7,7a,8,9,10-hexahydro-5H-pyrimido[5,4-f]pyrrolo[1,2-a][1,4]diazepin-5-one (compound 8),
(S)-6-(3-methyl-4-oxo-3,4-dihydroquinazolin-8-yl)-2-methylamino-6,7,7a,8,9,10-hexahydro-5H-pyrimido[5,4-f]pyrrolo[1,2-a][1,4]diazepin-5-one (compound 10),
(S)-6-(3-(3-(dimethylamino)propyl)-4-oxo-3,4-dihydroquinazolin-8-yl)-2-(methylamino)-6,7,7a,8,9,10-hexahydro-5H-pyrimido[5,4-f]pyrrolo[1,2-a][1,4]diazepin-5-one (compound 38),
(S)-6-(3-(3-(dimethylamino)propyl)-4-oxo-3,4-dihydroquinazolin-8-yl)-2-(ethylamino)-6,7,7a,8,9,10-hexahydro-5H-pyrimido[5,4-f]pyrrolo[1,2-a][1,4]diazepin-5-one (compound 39), and
(S)-2-(ethylamino)-6-(3-methyl-4-oxo-4,7-dihydro-3H-pyrrolo[2,3-d]pyrimidin-5-yl)-6,7,7a,8,9,10-hexahydro-5H-pyrimido[5,4-f]pyrrolo[1,2-a][1,4]diazepin-5-one (compound 113).

(21) A therapeutic and/or preventive agent for diabetic pain, which comprises, as an active ingredient, the compound or the pharmaceutically acceptable salt thereof according to any one of (1) to (20).

(22) A therapeutic and/or preventive agent for pain, which comprises, as an active ingredient, the compound or the pharmaceutically acceptable salt thereof according to any one of (1) to (20).

(23) A method of treating and/or preventing diabetic pain, which comprises administering an effective amount of the compound or the pharmaceutically acceptable salt thereof according to any one of (1) to (20).

(24) A method of treating and/or preventing pain, which comprises administering an effective amount of the compound or the pharmaceutically acceptable salt thereof according to any one of (1) to (20).

(25) The compound or the pharmaceutically acceptable salt thereof according to any one of (1) to (20) for use in the treatment and/or prevention of diabetic pain.

(26) The compound or the pharmaceutically acceptable salt thereof according to any one of (1) to (20) for use in the treatment and/or prevention of pain.

(27) Use of the compound or the pharmaceutically acceptable salt thereof according to any one of (1) to (20) for the manufacture of a therapeutic and/or preventive agent for diabetic pain.

(28) Use of the compound or the pharmaceutically acceptable salt thereof according to any one of (1) to (20) for the manufacture of a therapeutic and/or preventive agent for pain.

Effects of the Invention

The present invention provides a compound represented by general formula (I) or a pharmaceutically acceptable salt thereof having affinity for $\alpha_2\delta$ protein, and useful as a therapeutic and/or preventive agent for, for example, pain (specifically, diabetic pain, and the like), and the like.

MODE FOR CARRYING OUT THE INVENTION

In the following, compounds represented by general formula (I) are referred to as Compounds (I). The compounds having the other formula numbers are referred to in the same manner.

In the definition of each group of general formula (I), examples of the lower alkyl, and the lower alkyl moiety of the lower alkoxy include linear or branched alkyl having 1 to 10 carbon atoms, more specifically, methyl, ethyl, propyl, isopropyl, butyl, isobutyl, sec-butyl, tert-butyl, pentyl, isopentyl, neopentyl, hexyl, heptyl, octyl, nonyl, decyl, and the like.

Examples of the cycloalkyl include cycloalkyl having 3 to 8 carbon atoms, more specifically, cyclopropyl, cyclobutyl, cyclopentyl, cyclohexyl, cycloheptyl, cyclooctyl, and the like.

Examples of the nitrogen-containing heterocyclic group formed together with the adjacent nitrogen atom include a five- or six-membered monocyclic heterocyclic group that contains at least one nitrogen atom (the monocyclic heterocyclic group may contain other nitrogen atom(s), oxygen atom(s), or sulfur atom(s)), more specifically, aziridinyl, azetidinyl, pyrrolidinyl, piperidino, azepanyl, pyrrolyl, imidazolidinyl, imidazolyl, pyrazolidinyl, pyrazolinyl, pyrazolyl, piperazinyl, homopiperazinyl, oxazolidinyl, 2H-oxazolyl, thioxazolidinyl, 2H-thioxazolyl, morpholino, thiomorpholinyl, and the like.

Examples of the bicyclic heterocyclic group in which two six-membered rings are fused to each other include a bicyclic fused heterocyclic group in which two six-membered rings are fused to each other, and that contains at least one atom selected from a nitrogen atom, an oxygen atom, and a sulfur atom, more specifically, tetrahydroquinolyl, tetrahydroisoquinolyl, dihydro-2H-chromanyl, dihydro-4H-chromanyl, dihydro-2H-thiochromanyl, dihydro-4H-thiochromanyl, tetrahydroquinoxalinyl, tetrahydroquinazolinyl, dihydrobenzodioxanyl, quinolinyl, isoquinolinyl, cinnolinyl, phthalazinyl, quinazolinyl, quinoxalinyl, naphthyridinyl, pyrido[1,2-a]pyrimidinyl, dihydroquinazolinyl, dihydroquinolinyl, dihydroisoquinolinyl, and the like.

Preferred are groups with a bond, as represented by the following formula (ZA).

[Chemical Formula 11]

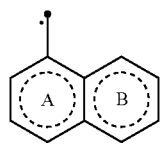

(ZA)

(wherein ring A and ring B each represent a six-membered ring consisting of atoms selected from a carbon atom, a nitrogen atom, an oxygen atom, and a sulfur atom, and one of the ring A and the ring B contains at least one atom selected from a nitrogen atom, an oxygen atom, and a sulfur atom).

Examples of the bicyclic heterocyclic group moiety of the bicyclic heterocyclic group in which an optionally substituted five-membered heterocyclic ring and an optionally substituted six-membered heterocyclic ring are fused to each other include a bicyclic fused heterocyclic group in which a five-membered ring containing at least one atom selected from a nitrogen atom, an oxygen atom, and a sulfur atom, and a six-membered ring containing at least one atom selected from a nitrogen atom, an oxygen atom, and a sulfur atom are fused to each other, more specifically, thieno[2,3-c]pyridyl, pyrrolo[2,3-c]pyridyl, thieno[3,4-d]pyrimidyl, thieno[3,2-d]pyrimidyl, thieno[3,2-c]pyridyl, furo[3,2-c]pyridyl, pyrrolo[2,3-d]pyrimidyl, thieno[2,3-d]pyrimidyl, pyrazolo[3,4-c]pyridyl, pyrazolo[4,3-d]pyrimidyl, furo[2,3-c]pyridyl, pyrrolo[3,2-c]pyridyl, 1,2,3,4-tetrahydropyrrolo[1,2-a]pyradyl, and the like.

Examples of the substituents (a) of the bicyclic heterocyclic group in which optionally substituted two six-membered rings are fused to each other, and the bicyclic heterocyclic group in which an optionally substituted five-membered heterocyclic ring and an optionally substituted six-membered heterocyclic ring are fused to each other, which may be the same or different and in number of 1 to 3, include substituents selected from the group consisting of oxo, halogen, hydroxy, sulfanyl, nitro, cyano, carboxy, carbamoyl, $C_{1-10}$alkyl which may be substituted with the groups exemplified in the below substituents (b) of the optionally substituted lower alkyl, $C_{3-8}$cycloalkyl, $C_{6-14}$aryl, an aliphatic heterocyclic group, an aromatic heterocyclic group, $C_{1-10}$alkoxy, $C_{3-8}$cycloalkoxy, $C_{6-14}$aryloxy, $C_{7-16}$aralkyloxy, $C_{2-11}$alkanoyloxy, $C_{7-15}$aroyloxy, $C_{1-10}$alkylsulfanyl, —$NR^{Xb}R^{Yb}$ (wherein, $R^{Xb}$ and $R^{Yb}$ may be the same or different, and each represents a hydrogen atom, $C_{1-10}$alkyl, $C_{3-8}$cycloalkyl, $C_{6-14}$aryl, an aromatic heterocyclic group, $C_{7-16}$aralkyl, $C_{2-11}$alkanoyl, $C_{7-15}$aroyl, $C_{1-10}$alkoxycarbonyl, or $C_{7-16}$aralkyloxycarbonyl), $C_{2-11}$alkanoyl, $C_{7-15}$aroyl, $C_{1-10}$alkoxycarbonyl, $C_{6-14}$aryloxycarbonyl, $C_{1-10}$alkylcarbamoyl, di$C_{1-10}$alkylcarbamoyl, and the like. Preferred examples include oxo; $C_{1-10}$alkyl which may be substituted with a group selected from halogen, hydroxy, $C_{1-10}$alkoxy, and —$NR^{Xbb}R^{Ybb}$ (wherein $R^{Xbb}$ and $R^{Ybb}$ may be the same or different, and each represents a hydrogen atom, or $C_{1-10}$alkyl); $C_{3-8}$cycloalkyl; and the like. More preferred examples include oxo; $C_{1-10}$alkyl which may be substituted with a fluorine atom, hydroxy, methoxy, or dimethylamino; and cyclopropyl; and the like.

Examples of the substituents (b) of the optionally substituted lower alkyl, which may be the same or different and in number of 1 to 3, include substituents selected from the group consisting of halogen, hydroxy, sulfanyl, nitro, cyano, carboxy, carbamoyl, $C_{3-8}$cycloalkyl, $C_{6-14}$aryl, an aliphatic heterocyclic group, an aromatic heterocyclic group, $C_{3-8}$cycloalkoxy, $C_{1-10}$alkoxy, $C_{6-14}$aryloxy, $C_{7-16}$aralkyloxy, $C_{2-11}$alkanoyloxy, $C_{7-15}$aroyloxy, $C_{1-10}$alkylsulfanyl, —$NR^{X}R^{Y}$ (wherein $R^{X}$ and $R^{Y}$ may be the same or different, and each represents a hydrogen atom, $C_{1-10}$alkyl, $C_{3-8}$cycloalkyl, $C_{6-14}$aryl, an aromatic heterocyclic group, $C_{7-16}$aralkyl, $C_{2-11}$alkanoyl, $C_{7-15}$aroyl, $C_{1-10}$alkoxycarbonyl, or $C_{7-16}$aralkyloxycarbonyl), $C_{2-11}$alkanoyl, $C_{7-15}$aroyl, $C_{1-10}$alkoxycarbonyl, $C_{6-14}$aryloxycarbonyl, $C_{1-10}$alkylcarbamoyl, di$C_{1-10}$alkylcarbamoyl, and the like. Preferred examples include halogen, hydroxy, $C_{1-10}$alkoxy, —$NR^{Xaa}R^{Yaa}$ (wherein $R^{Xaa}$ and $R^{Yaa}$ may be the same or different, and each represents a hydrogen atom, or $C_{1-10}$alkyl), and the like. More preferred examples include a fluorine atom, hydroxy, methoxy, dimethylamino, and the like.

In the above examples of the substituents, examples of the $C_{1-10}$alkyl, and the $C_{1-10}$alkyl moiety of the $C_{1-10}$alkoxy, the $C_{2-11}$alkanoyloxy, the $C_{1-10}$alkylsulfanyl, the $C_{2-11}$alkanoyl, the $C_{1-10}$alkoxycarbonyl, the $C_{1-10}$alkylcarbamoyl, and the di$C_{1-10}$alkylcarbamoyl include the groups exemplified in the above examples for the lower alkyl. The two $C_{1-10}$alkyl moieties of the di$C_{1-10}$alkylcarbamoyl may be the same or different.

Examples of the $C_{3-8}$cycloalkyl, and the cycloalkyl moiety of the $C_{3-8}$cycloalkoxy include the groups exemplified in the above examples for the cycloalkyl.

Examples of the $C_{6-14}$aryl, and the aryl moiety of the $C_{6-14}$aryloxy, the $C_{7-15}$aroyl, the $C_{7-15}$aroyloxy, and the $C_{6-14}$aryloxycarbonyl include phenyl, naphthyl, azulenyl, anthryl, and the like.

Examples of the aryl moiety of the $C_{7-16}$aralkyloxy, $C_{7-16}$aralkyl, and the $C_{7-16}$aralkyloxycarbonyl include the groups exemplified in the above examples for the $C_{6-14}$aryl, and examples of the alkyl moiety of the same include $C_{1-10}$alkylene, more specifically, groups formed by removing a hydrogen atom from the groups exemplified in the above examples for the lower alkyl.

Examples of the aliphatic heterocyclic group include a five- or six-membered monocyclic aliphatic heterocyclic group containing at least one atom selected from a nitrogen atom, an oxygen atom, and a sulfur atom; a bicyclic or tricyclic fused aliphatic heterocyclic group formed by fusing three- to eight-membered rings and containing at least one atom selected from a nitrogen atom, an oxygen atom, and a sulfur atom; and the like, more specifically, aziridinyl, azetidinyl, pyrrolidinyl, piperidino, piperidinyl, azepanyl, 1,2,5,6-tetrahydropyridyl, imidazolidinyl, pyrazolidinyl, piperazinyl, homopiperazinyl, pyrazolinyl, oxiranyl, tetrahydrofuranyl, tetrahydro-2H-pyranyl, 5,6-dihydro-2H-pyranyl, oxazolidinyl, morpholino, morpholinyl, thioxazolidinyl, thiomorpholinyl, 2H-oxazolyl, 2H-thioxazolyl, dihydroindolyl, dihydroisoindolyl, dihydrobenzofuranyl, benzoimidazolidinyl, dihydrobenzooxazolyl, dihydrobenzothioxazolyl, benzodioxolinyl, tetrahydroquinolyl, tetrahydroisoquinolyl, dihydro-2H-chromanyl, dihydro-4H-chromanyl, dihydro-2H-thiochromanyl, dihydro-4H-thiochromanyl, tetrahydroquinoxalinyl, tetrahydroquinazolinyl, dihydrobenzodioxanyl, and the like.

Examples of the aromatic heterocyclic group include a five- or six-membered monocyclic aromatic heterocyclic group containing at least one atom selected from a nitrogen atom, an oxygen atom, and a sulfur atom; a bicyclic or tricyclic fused aromatic heterocyclic group formed by fusing three- to eight-membered rings and containing at least one atom selected from a nitrogen atom, an oxygen atom, and a sulfur atom; and the like, more specifically, furyl, thienyl, pyrrolyl, imidazolyl, pyrazolyl, oxazolyl, isooxazolyl, oxadiazolyl, thiazolyl, isothiazolyl, thiadiazolyl, triazolyl, tetrazolyl, pyridyl, pyridazinyl, pyrimidinyl, pyrazinyl, triazinyl, benzofuranyl, benzothiophenyl, benzooxazolyl, benzothiazolyl, isoindolyl, indolyl, indazolyl, benzoimidazolyl, benzotriazolyl, oxazolopyrimidinyl, thiazolopyrimidinyl, pyrrolopyridinyl, pyrrolopyrimidinyl, imidazopyridinyl, purinyl, quinolinyl, isoquinolinyl, cinnolinyl, phthalazinyl, quinazolinyl, quinoxalinyl, naphthyridinyl, and the like.

The halogen means each atom of fluorine, chlorine, bromine, and iodine.

Examples of the pharmaceutically acceptable salts of Compound (I) include pharmaceutically acceptable acid addition salts, metal salts, ammonium salts, organic amine addition salts, amino acid addition salts, and the like. Examples of the pharmaceutically acceptable acid addition salts of Compound (I) include inorganic acid salts such as hydrochloride, hydrobromate, nitrate, sulfate, and phosphate; organic acid salts such as acetate, oxalate, maleate, fumarate, citrate, benzoate, methanesulfonate, and the like. Examples of the pharmaceutically acceptable metal salts include alkali metal salts such as sodium salt, potassium salt, and the like; alkali-earth metal salts such as magnesium salt, calcium salt, and the like; aluminum salts; zinc salts; and the like. Examples of the pharmaceutically acceptable ammonium salts include salts of ammonium, tetramethylammonium, or the like. Examples of the pharmaceutically acceptable organic amine addition salts include addition salts of morpholine, piperidine, or the like. Examples of the pharmaceutically acceptable amino acid addition salts include addition salts of lysine, glycine, phenylalanine, aspartic acid, glutamic acid, or the like.

Producing processes of Compound (I) are described below.

In the producing processes below, when the defined groups undergo changes under the conditions of the producing processes, or are inappropriate for carrying out the producing processes, the desired products can be produced by using a protective group introducing and removing method commonly used in organic synthesis chemistry [for example, such as the method described in Protective Groups in Organic Synthesis, Third Edition; T. W. Greene; John Wiley & Sons Inc. (1999)]. Further, the order of the reaction steps in procedures such as the introduction of substituents may be changed, if necessary.

Producing Process 1

Compound (IA) in which $R^a$ of Compound (I) is a hydrogen atom can be produced, for example, according to the following steps.

[Chemical Formula 12]

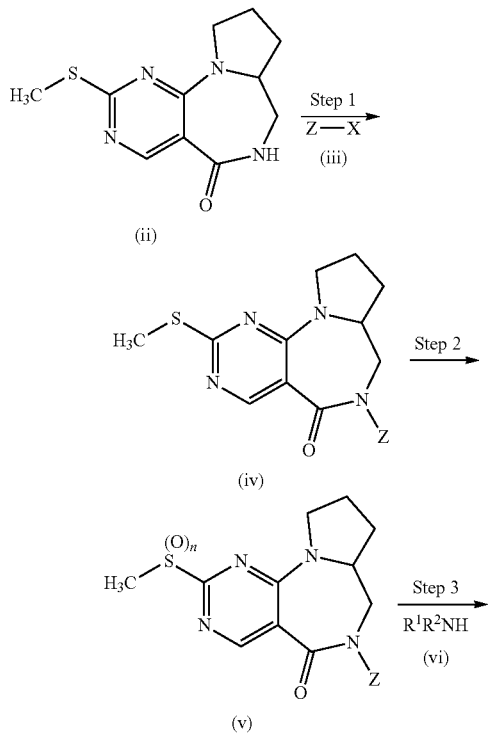

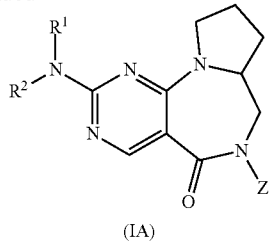

(IA)

(wherein Z, R¹, and R² have the same definitions as described above, respectively, X represents an iodine atom, a bromine atom, or a chlorine atom, and n represents 1 or 2).

Step 1

Compound (iv) can be produced by reacting Compound (II) obtained according to the method described in WO2008/149834 with 1 to 10 equivalents of Compound (iii) in a solvent in the presence of a catalytic amount to 10 equivalents of a copper compound or a palladium compound at a temperature between room temperature and 140° C. for 5 minutes to 72 hours. The reaction also can be performed in the presence of a catalytic amount to 10 equivalents of a base, or further in the presence of a catalytic amount to 10 equivalents of an organophosphorus compound.

Examples of the copper compound include copper(0), copper(I) iodide, copper(II) iodide, copper(II) acetate, copper(II) oxide, copper(I) chloride, and the like. Preferred examples include copper(I) iodide, copper(II) acetate, and the like. Examples of the palladium compound include palladium(II) acetate, bis(triphenylphosphine)palladium(II) chloride, tetrakis(triphenylphosphine)palladium(0), [1,2-bis(diphenylphosphino)ethane]palladium(II) chloride, (1,1'-bis(diphenylphosphino)ferrocene)palladium(II) chloride, and the like. Preferred examples include palladium(II) acetate, bis(triphenylphosphine)palladium(II) chloride, tetrakis(triphenylphosphine)palladium(0), and the like. Examples of the base include potassium carbonate, cesium carbonate, lithium chloride, potassium chloride, potassium tert-butoxide, sodium tert-butoxide, triethylamine, potassium acetate, sodium ethoxide, sodium carbonate, sodium hydroxide, potassium phosphate, ethylenediamine, glycine, N-methylpyrrolidine, pyridine, and the like. Preferred examples include potassium carbonate, cesium carbonate, potassium tert-butoxide, potassium phosphate, ethylenediamine, and the like. Examples of the organophosphorus compound include triphenylphosphine, tri(2-furyl)phosphine, 2-dicyclohexylphosphino-2'-(N,N-dimethylamino)biphenyl, diphenylphosphinoferrocene, and the like. Preferred examples include 2-dicyclohexylphosphino-2'-(N,N-dimethylamino)biphenyl, and the like. Examples of the solvent include diethyl ether, tetrahydrofuran (THF), 1,4-dioxane, N,N-dimethylformamide (DMF), N,N-dimethylacetoamide (DMA), dimethylsulfoxide (DMSO), benzene, toluene, xylene, dichloromethane, chloroform, carbon tetrachloride, 1,2-dichloroethane, acetonitrile, ethyl acetate, methyl acetate, methyl ethyl ketone, methanol, ethanol, propanol, isopropyl alcohol, butanol, hexane, and the like. Preferred examples include THF, 1,4-dioxane, DMF, and the like.

Herein, compound (iii) can be obtained as a commercially available product, or by using known methods (for example, *Jikken Kagaku Kouza* 13, 5th Edition, The Chemical Society of Japan).

Step 2

Compound (v) can be produced by treating Compound (iv) with 1 equivalent to a large excess amount, preferably 1 to 10 equivalents of an oxidizing agent in a solvent at a temperature between 0° C. and the boiling point of the solvent used, preferably between 0° C. and 50° C., for 5 minutes to 72 hours.

Examples of the solvent include dichloromethane, chloroform, 1,2-dichloroethane, THF, 1,4-dioxane, dimethoxyethane, diethyl ether, diisopropyl ether, methanol, ethanol, isopropyl alcohol, benzene, toluene, xylene, acetonitrile, ethyl acetate, water, and the like. These can be used alone or by being mixed. Preferred examples include dichloromethane, and the like.

Examples of the oxidizing agent include m-chloroperbenzoic acid (m-CPBA), benzoyl peroxide, peracetic acid, hydrogen peroxide, sodium periodate, and the like. Preferred examples include m-CPBA, and the like.

Among Compounds (v), compounds in which n is 1 and compounds in which n is 2 are obtained, for example, by adjusting the equivalent number of the oxidizing agent, the reaction temperature, and the like, and these may be obtained as a mixture. In the case of a mixture, the proportions and the like are not particularly limited, and the compounds may directly be used in the next step, in any case.

Step 3

Compound (I) can be produced by reacting Compound (v) with 1 equivalent to a large excess amount, preferably 1 to 5 equivalents of Compound (vi) in a solvent at a temperature between 0° C. and the boiling point of the solvent used, preferably between room temperature and the boiling point of the solvent used, for 5 minutes to 72 hours.

Examples of the solvent include dichloromethane, chloroform, THF, 1,4-dioxane, 1,2-dichloroethane, dimethoxyethane, DMF, DMA, N-methylpyrrolidone (NMP), DMSO, benzene, toluene, xylene, acetonitrile, ethyl acetate, and the like. These may be used alone or by being mixed. Preferred examples include THF, 1,2-dichloroethane, and the like.

Herein, compound (vi) can be obtained as, for example, a commercially available product, and the like.

Producing Process 2

Compound (IB) in which $R^a$ of Compound (I) is halogen, hydroxy, or lower alkoxy can be produced, for example, according to the methods described in Examples 115 to 120.

The transformation of the functional groups contained in Z of Compound (I) can be performed by using known methods [for example, methods described in Comprehensive Organic Transformations, 2nd edition, R. C. Larock, Vch Verlagsgesellschaft Mbh (1999), and the like] or modified methods thereof.

The intermediates and the target compounds in each producing process above can be isolated and purified by being subjected to various separation and purification methods commonly used in organic synthesis chemistry, including, for example, filtration, extraction, washing, drying, concentration, recrystallization, various chromatography techniques, and the like. The intermediates can be used in the next reaction without being purified.

Compound (I) may exist as stereoisomers such as geometric isomers and optical isomers, and tautomers, and the like. All possible isomers including those above and mixtures thereof, are encompassed within the scope of the present invention.

To obtain a salt of Compound (I), when Compound (I) is obtained in the form of a salt, it may be purified as it is. Further, when Compound (I) is obtained in a free form, Compound (I) can be dissolved or suspended in a suitable solvent, followed by addition of an acid or a base to form a salt. Then, the resulting salt can be isolated and purified.

Compound (I) and a pharmaceutically acceptable salt thereof may exist in the form of adducts with water or various solvents. Such adducts are also encompassed within the scope of the present invention.

Specific examples of Compound (I) obtained in the present invention are presented in Tables 1 to 11 below. It should be noted that the compounds of the present invention are not limited to the following.

TABLE 1

(I)

| Example No. | Compound No. | R¹ | Z |
|---|---|---|---|
| 1 | 1 | $CH_3CH_2$— | (pyrido[1,2-a]pyrimidin-4-one) |
| 2 | 2 | $CH_3$— | |
| 3 | 3 | $CH_3CH_2$— | (2-methyl pyrido[1,2-a]pyrimidin-4-one) |
| 4 | 4 | $CH_3$— | |
| 5 | 5 | $CH_3CH_2$— | (2-ethyl pyrido[1,2-a]pyrimidin-4-one) |
| 6 | 6 | $CH_3$— | |
| 7 | 7 | $CH_3CH_2$— | (2,3-dimethyl pyrido[1,2-a]pyrimidin-4-one) |
| 8 | 8 | $CH_3$— | |
| 9 | 9 | $CH_3CH_2$— | (3-methyl quinazolin-4-one) |
| 10 | 10 | $CH_3$— | |

TABLE 2

(I)

| Example No. | Compound No. | R¹ | Z |
|---|---|---|---|
| 11 | 11 | $CH_3CH_2$— | (2,3-dimethyl quinazolin-4-one) |
| 12 | 12 | $CH_3$— | |
| 13 | 13 | $CH_3CH_2$— | (3-ethyl quinazolin-4-one) |
| 14 | 14 | $CH_3$— | |
| 15 | 15 | $CH_3CH_2$— | (3-methyl quinazolin-4-one isomer) |
| 16 | 16 | $CH_3$— | |
| 17 | 17 | $CH_3CH_2$— | (2-methyl isoquinolin-1-one) |
| 18 | 18 | $CH_3$— | |

TABLE 3

(I)

| Example No. | Compound No. | R¹ | Z |
|---|---|---|---|
| 19 | 19 | $CH_3CH_2$— | (3-methyl pyrido[1,2-a]pyrimidin-4-one) |
| 20 | 20 | $CH_3$— | |

TABLE 3-continued

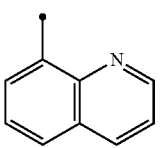
(I)

| Example No. | Compound No. | R¹ | Z |
|---|---|---|---|
| 21 | 21 | CH₃CH₂— | 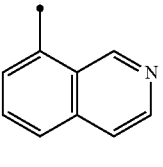 |
| 22 | 22 | CH₃— | |
| 23 | 23 | CH₃CH₂— | 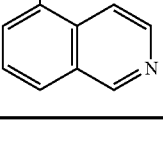 |
| 24 | 24 | CH₃— | |
| 25 | 25 | CH₃CH₂— | 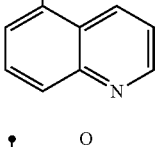 |
| 26 | 26 | CH₃— | |

TABLE 4

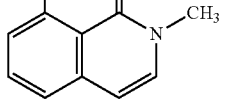
(I)

| Example No. | Compound No. | R¹ | Z |
|---|---|---|---|
| 27 | 27 | CH₃CH₂— | (quinoline) |
| 28 | 28 | CH₃— | |
| 29 | 29 | CH₃CH₂— | (N-methylisoquinolinone) |
| 30 | 30 | CH₃— | |

TABLE 4-continued (I)

| Example No. | Compound No. | R¹ | Z |
|---|---|---|---|
| 31 | 31 | CH₃CH₂— | (N-methylquinolinone) |
| 32 | 32 | CH₃— | |

TABLE 5

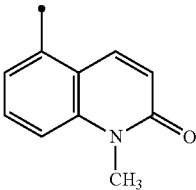
(I)

| Example No. | Compound No. | R¹ | Z |
|---|---|---|---|
| 33 | 33 | H— | (3-ethylquinazolinone) |
| 34 | 34 | CH₃— | (3-(2-methoxyethyl)quinazolinone) |
| 35 | 35 | CH₃CH₂— | |
| 36 | 36 | CH₃— | (3-(3-methoxypropyl)quinazolinone) |
| 37 | 37 | CH₃CH₂— | |

TABLE 5-continued
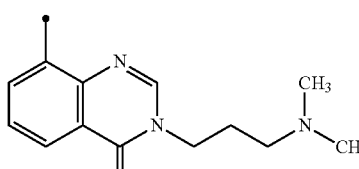
| Example No. | Compound No. | R¹ | Z |
|---|---|---|---|
| 38 | 38 | CH₃— | 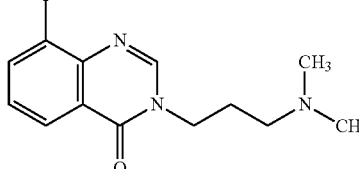 |
| 39 | 39 | CH₃CH₂— | |
| 40 | 40 | CH₃— | 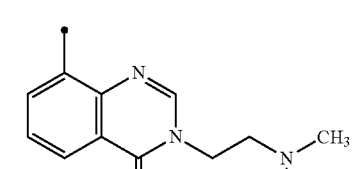 |
| 41 | 41 | CH₃CH₂— | |
| 42 | 42 | CH₃— | 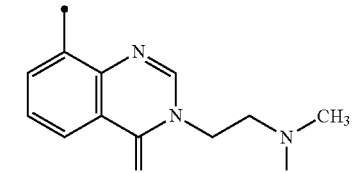 |
| 43 | 43 | CH₃CH₂— | |
TABLE 6
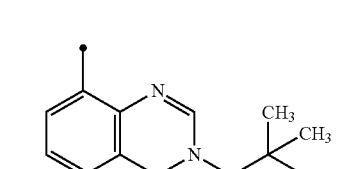
| Example No. | Compound No. | R¹ | Z |
|---|---|---|---|
| 44 | 44 | H— | 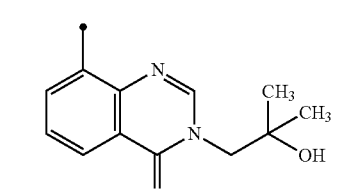 |
| 45 | 45 | CH₃CH₂— | 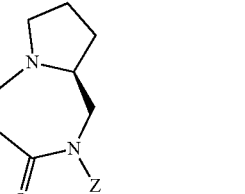 |
| 46 | 46 | CH₃— | |
| 47 | 47 | CH₃CH₂— | 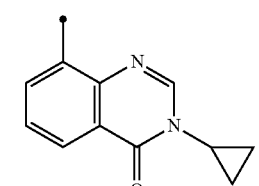 |
| 48 | 48 | CH₃— | |
| 49 | 49 | H— | |
| 50 | 50 | CH₃CH₂— | 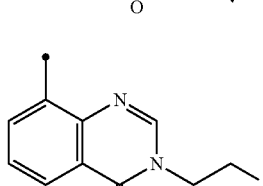 |
| 51 | 51 | CH₃— | |
| 52 | 52 | CH₃CH₂— | 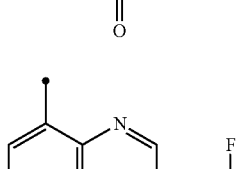 |
| 53 | 53 | CH₃— | |
| 54 | 54 | CH₃CH₂— | 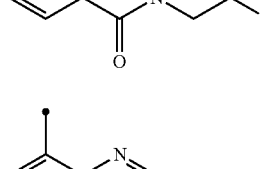 |
| 55 | 55 | CH₃— | |
| 56 | 56 | CH₃CH₂— | 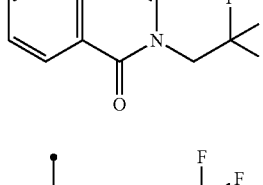 |
| 57 | 57 | CH₃— | |
| 58 | 58 | H— | |

TABLE 7

(I)

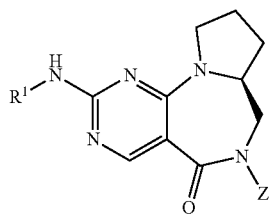

| Example No. | Compound No. | R¹ | Z |
|---|---|---|---|
| 59 | 59 | CH₃CH₂— | (quinazolinone with 2-CH₃, N-CH₂CH₂F) |
| 60 | 60 | CH₃— | |
| 61 | 61 | CH₃— | (quinazolinone with 2-CH₃, N-CH₂CHF₂) |
| 62 | 62 | CH₃CH₂— | (quinazolinone with N-CH₂CH₂OH) |
| 63 | 63 | CH₃— | |
| 64 | 64 | H— | |
| 65 | 65 | CH₃CH₂— | (quinazolinone with 2-CH₂OCH₃, N-CH₃) |
| 66 | 66 | CH₃— | |
| 67 | 67 | CH₃CH₂— | (pyrido[3,4]pyrimidinone with N-CH₃) |
| 68 | 68 | CH₃— | |
| 69 | 69 | FCH₂CH₂— | (quinazolinone with N-CH₃) |
| 70 | 70 | F₂CHCH₂— | |
| 71 | 71 | CH₃CH₂CH₂— | |

TABLE 8

(I)

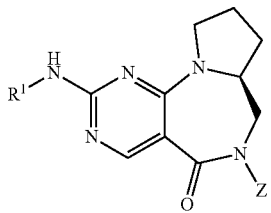

| Example No. | Compound No. | R¹ | Z |
|---|---|---|---|
| 72 | 72 | FCH₂CH₂— | (pyrido[1,2-a]pyrimidinone with 2-CH₃, 3-CH₃) |
| 73 | 73 | F₂CHCH₂— | |
| 74 | 74 | CH₃CH₂CH₂— | |
| 75 | 75 | CH₃CH₂— | (pyrido[1,2-a]pyrimidinone with 2-CF₃) |
| 76 | 76 | CH₃— | |
| 77 | 77 | CH₃CH₂— | (isoquinolinone with N-ethyl) |
| 78 | 78 | CH₃— | |
| 79 | 79 | H— | |
| 80 | 80 | H— | (isoquinolinone with N-CH₃) |
| 81 | 81 | CH₃CH₂— | (3,4-dihydroisoquinolinone with N-CH₃) |
| 82 | 82 | CH₃— | |
| 83 | 83 | CH₃CH₂— | (3,4-dihydroquinolin-2-one with N-CH₃) |
| 84 | 84 | CH₃— | |

TABLE 9

| Example No. | Compound No. | R¹ | Z |
|---|---|---|---|
| 85 | 85 | H— | quinazolinone-3-methyl |
| 86 | 86 | CH₃CH₂— | quinazolinone-3-ethyl |
| 87 | 87 | CH₃— | |
| 88 | 88 | CH₃CH₂— | 2-methylquinazolinone-3-methyl |
| 89 | 89 | CH₃— | |
| 90 | 90 | CH₃CH₂— | thieno[3,2-c]pyridinone-N-methyl |
| 91 | 91 | CH₃— | |
| 92 | 92 | H— | |
| 93 | 93 | CH₃CH₂— | pyrrolo-pyridinone-dimethyl |
| 94 | 94 | CH₃— | |
| 95 | 95 | H— | |
| 96 | 96 | CH₃— | thieno[3,4-d]pyrimidinone-3-methyl |
| 97 | 97 | CH₃CH₂— | |
| 98 | 98 | CH₃— | thieno[2,3-d]pyrimidinone-3-methyl |
| 99 | 99 | CH₃CH₂— | |

TABLE 10

| Example No. | Compound No. | R¹ | Z |
|---|---|---|---|
| 100 | 100 | CH₃— | thieno[3,2-d]pyrimidinone-N-(2-fluoroethyl) |
| 101 | 101 | CH₃CH₂— | |
| 102 | 102 | CH₃— | 2-methyl-thieno[3,2-d]pyrimidinone-N-(2-fluoroethyl) |
| 103 | 103 | CH₃CH₂— | |
| 104 | 104 | CH₃— | thieno[2,3-c]pyridinone-N-methyl |
| 105 | 105 | CH₃CH₂— | |
| 106 | 106 | CH₃— | furo[2,3-c]pyridinone-N-methyl |
| 107 | 107 | CH₃CH₂— | |
| 108 | 108 | H— | |
| 109 | 109 | CH₃— | pyrrolo[2,3-d]pyrimidinone-N,N'-dimethyl |
| 110 | 110 | CH₃CH₂— | |
| 111 | 111 | H— | |
| 112 | 112 | CH₃— | pyrrolo-pyrimidinone-N-methyl |
| 113 | 113 | CH₃CH₂— | |
| 114 | 114 | CH₃— | thieno[2,3-d]pyrimidinone-N-methyl |

TABLE 11

(structure I shown: pyrrolo-pyrimidine-diazepine core with R¹NH— group and X substituent on pyrrolidine ring, linked to a quinazolinone bearing N—CH₃)

| Example No. | Compound No. | R¹ | X |
|---|---|---|---|
| 115 | 115 | CH₃CH₂— | F |
| 116 | 116 | CH₃— | F |
| 117 | 117 | CH₃CH₂— | OMe |
| 118 | 118 | CH₃CH₂— | OH |
| 119 | 119 | CH₃CH₂— | OH |
| 120 | 120 | CH₃CH₂— | OMe |

Next, the pharmacological effects of representative compounds (I) are described below in detail using Test Examples.

Test Example 1

α₂δ Protein Binding Experiment

Experiment was conducted according to the methods described in European Journal of Pharmacology, 1993, 244, p. 293-301, using the report of Woodruff G N et al. as a reference (Journal of Biological Chemistry, 1996, 271, p. 5768-5776).

(1) Preparation of Membrane Fraction from Rat Cerebral Cortex

A male SD rat was purchased at the age of 6 weeks, and kept for at least 7 days prior to experiment. The cerebral cortex was removed, and gently washed with Tris-sucrose buffer A (containing 0.32 mol/L sucrose, 5 mmol/L tris-acetate, 1 mmol/L ethylenediaminetetraacetic acid (EDTA), 1 mmol/L ethylene glycol tetraacetic acid (EGTA), and a protease inhibitor cocktail tablet, pH 7.4). The cerebral cortex was placed in Tris-sucrose buffer A, and homogenized in 15 strokes (250 rpm) using a teflon homogenizer to obtain a crude extract. The crude extract was centrifuged at 4° C. for 10 minutes at 2,000 rpm, and the supernatant was collected. After adding Tris-sucrose buffer A to the resulting precipitate, the same homogenization and centrifugation procedures as above were performed, and the resulting supernatant was mixed with the previously obtained supernatant to obtain a total collected supernatant. The total collected supernatant was centrifuged at 4° C. for 30 minutes at 20,000 rpm, and the supernatant (cytosolic fraction) was removed. Tris-acetate buffer A (containing 5 mmol/L tris-acetate, 1 mmol/L EDTA, 1 mmol/L EGTA, and a protease inhibitor cocktail tablet, pH 8.0) was added to the remaining precipitate (cell membrane fraction), and the mixture was stirred for 1 hour. The stirred extract was centrifuged at 4° C. for 30 minutes at 26,500 rpm, and Tris-sucrose buffer B (containing 1.2 mol/L sucrose, 5 mmol/L tris-acetate, pH 7.4) was added to the resulting precipitate. The mixture was dispensed in centrifuge tubes in 15-mL portions, and 9 mL of Tris-sucrose buffer C (containing 0.9 mol/L sucrose, 5 mmol/L tris-acetate, pH 7.4) was gently layered on the mixture in each centrifuge tube without disrupting the interface. The centrifuge tubes were centrifuged at 4° C. for 90 minutes at 43,000 rpm, and the membrane fraction at the interface of the Tris-sucrose buffer B and the Tris-sucrose buffer C was collected with a Pasteur pipette. After adding Tris-acetate buffer B (5 mmol/L tris-acetate, pH 7.4) to the collected membrane fraction, the mixture was centrifuged at 4° C. for 20 minutes at 26,500 rpm. The resulting precipitate was resuspended in Tris-acetate buffer B to obtain a cerebral cortex membrane fraction, and the cerebral cortex membrane fraction was stored at −80° C. until use in the binding experiment. For the binding experiment, the stored suspension was centrifuged at 4° C. for 30 minutes at 32,000 rpm, and Binding buffer [a 0.1 w/v % bovine serum albumin (BSA)-containing 10 mmol/L 4-(2-hydroxyethyl)-1-piperazineethanesulfonic acid (HEPES) solution adjusted to pH 7.4 with sodium hydroxide] for the binding experiment was added to the obtained precipitate, and resuspended with a syringe equipped with an injection needle to adjust to the desired concentration.

(2) [³H]-Gabapentin Binding Inhibition Experiment

A test compound (20 μL) diluted to 5 times of the final concentration with Binding buffer, [³H]-gabapentin diluted to 100 nmol/L with binding buffer [20 μL (final concentration 20 nmol/L)], and the rat cerebral cortex membrane fraction (60 μL; 12 μg membrane fraction) obtained in the (1) above were added to each well of a 96-well round-bottom plate. After being sufficiently mixed, these were allowed to react at room temperature for 1 hour. After the reaction, the reaction sample was suction filtered using a filter plate with 50 μL/well of 0.3 vol % polyethyleneimine added, and a cell harvester. The filter was then washed with ice-cooled Wash buffer (100 mmol/L NaCl, 0.1 w/v % BSA). After being washed, the filter plate was dried, and a scintillation cocktail (MicroScint-20, purchased from PerkinElmer) was added (50 μL/well), and the radioactivity on the filter was measured. The radioactivity obtained in the absence of the test compound was measured as total binding amount, and the radioactivity obtained by addition of an unlabeled gabapentin (final concentration 100 mmol/L) as a test compound was measured as non-specific binding amount. The binding inhibitory activity of the test compound was calculated according to the following equation, by using the radioactivity in the presence of the test compound as the binding amount after addition of the test compound.

[Equation 1]

$$\text{Inhibition rate (\%)} = 100 \times \frac{(\text{Total binding amount}) - (\text{Binding amount after addition of test compound})}{(\text{Total binding amount}) - (\text{Non-specific binding amount})}$$

Compounds 1 to 19, Compounds 21 to 23, Compounds 25 to 39, Compounds 44 to 69, Compounds 71 to 81, Compound 83, Compound 85, Compound 90, Compound 91, Compound 93, Compounds 96 to 113, Compound 115, Compound 117, and Compound 118 showed 50% or greater inhibitory activity at 0.1 μmol/L concentration. The $IC_{50}$ values of these compounds were calculated by using an ordinary method.

The results for some of the compounds are presented in Table 12.

TABLE 12

| Compound No. | $\alpha_2\delta$ receptor binding activity ($IC_{50}$) |
| --- | --- |
| 3 | 5.2 nmol/L |
| 7 | 2.7 nmol/L |
| 8 | 4.7 nmol/L |
| 10 | 2.6 nmol/L |
| 11 | 2.6 nmol/L |
| 14 | 4.0 nmol/L |
| 15 | 3.9 nmol/L |
| 17 | 5.0 nmol/L |
| 38 | 1.2 nmol/L |
| 39 | 0.7 nmol/L |
| 59 | 4.8 nmol/L |
| 65 | 3.8 nmol/L |
| 68 | 4.1 nmol/L |
| 71 | 3.0 nmol/L |
| 97 | 3.0 nmol/L |
| 112 | 3.6 nmol/L |
| 113 | 2.6 nmol/L |

The above test confirmed that Compound (I) or a pharmaceutically acceptable salts thereof had high affinity for $\alpha_2\delta$ protein. Therefore, it is expected that Compound (I) or a pharmaceutically acceptable salt thereof is useful as a therapeutic and/or preventive agent for diseases such as pain (for example, neuropathic pain, trigeminal neuralgia, diabetic pain, postherpetic neuralgia, phantom pain, neuropathic lower back pain, HIV-related pain, fibromyalgia syndrome, cancer pain, inflammatory pain, acute pain, chronic pain, postoperative pain, pain after teeth extraction, chronic musculoskeletal pain, nociceptive pain, psychogenic pain, menstrual pain, and the like), migraine, pruritus, lower urinary tract symptoms, irritable bowel syndrome, epilepsy, restless legs syndrome, hot flash, mood disorder, sleep disorder, and the like.

Test Example 2

Pain Relieving Effect of Compounds in Streptozotocin-Induced Diabetic Pain Model Streptozotocin (STZ)-administered rats are widely used as an insulin-dependent diabetes model. In this model, decreased pain thresholds in response to mechanical stimulation are observed as in diabetic neuropathy patients [British Journal of Pharmacology, 1997, Vol. 122, p. 1478-1482].

(1) Preparation of STZ-Induced Diabetes Model

A STZ solution was prepared as a 30 mg/mL solution by being dissolved in a 0.05 mol/L citric acid aqueous solution (pH 4 to 4.5). The STZ solution (30 mg/mL) was intraperitoneally administered in a 2 mL/kg volume to rats (60 mg/kg). Rats showing 250 mg/dL or higher blood glucose levels after 1 week from the STZ administration were obtained as diabetic rats.

(2) Measurement of Pain Relieving Effect

The evaluation of Pain was performed with von Frey filaments [product name: Touch Test Sensory Evaluator, Model Number Model 58011, Muromachi Kikai Co., Ltd.], and the results were calculated as pain thresholds. Specifically, the above diabetic rats were stimulated by the pressure applied to the underside of the feet with von Frey filaments of varying stimulus strengths, and the stimulus strength at which the mice withdrew their feet was determined. From the result, a 50% pain threshold (paw withdrawal threshold) (g) was calculated by using the Dixon's up and down method [Annual Review of Pharmacology and Toxicology, 1980, Vol. 20, p. 441-462].

Rats with a 50% pain threshold of less than 4 g were used for the evaluation of the test compounds. The test compounds were each suspended in a 0.5% methyl cellulose aqueous solution, and orally administered in a 5 mL/kg volume. After 1 hour, the pain threshold was measured using von Frey filaments. The pain relief rate of the test compound was calculated by using the following equation.

[Equation 2]

$$\text{Relief rate (\%)} = 100 \times \frac{(\text{50\% Threshold after administration of test compound}) - (\text{50\% Threshold after solvent administration})}{(\text{50\% Threshold of nomal rat}) - (\text{50\% Threshold after solvent administration})}$$

The test results are presented in Table 13. Compound 8 and Compound 10 showed good inhibition rate, and usefulness of these compounds as therapeutic and/or preventive agents for diabetic pain was confirmed. Namely, it was suggested that Compound (I) or a pharmaceutically acceptable salt thereof shows good therapeutic and/or preventive effects on diabetic pain.

TABLE 13

Relieving Effect on Streptozotocin-Induced Diabetic Pain Model

| Test Compound (dose) | Relief Rate |
| --- | --- |
| Compound 8 (1 mg/kg) | 85% |
| Compound 10 (1 mg/kg) | 91% |
| Compound 1-146 (1 mg/kg) | 6% |

From the above test, Compound (I) or a pharmaceutically acceptable salt thereof was considered to be useful particularly as a therapeutic and/or preventive agent for diabetic pain.

Compound (I) or a pharmaceutically acceptable salt thereof also had good pharmacokinetic properties.

Further, the administration of Compound (I) or a pharmaceutically acceptable salt thereof to an animal did not affect its coordinated movement, sleep time, and the like. It was thus considered that Compound (I) or a pharmaceutically acceptable salt thereof had few side effects, and was useful as a good active ingredient of therapeutic and/or preventive agents for diseases such as pain (for example, neuropathic pain, trigeminal neuralgia, diabetic pain, postherpetic neuralgia, phantom pain, neuropathic lower back pain, HIV-related pain, fibromyalgia syndrome, cancer pain, inflammatory pain, acute pain, chronic pain, postoperative pain, pain after teeth extraction, chronic musculoskeletal pain, nociceptive pain, psychogenic pain, menstrual pain, and the like), and the like.

A pharmaceutical formulation relating to the present invention may contain Compound (I) or a pharmaceutically acceptable salt thereof as an active ingredient either alone or as a mixture with any other active ingredient for the treatment. Furthermore, these pharmaceutical formulations are produced by mixing the active ingredient with one or more pharmaceutically acceptable carriers (for example, diluents, solvents, excipients, and the like), and then subjecting the mixture to any method well-known in the technical field of pharmaceutics.

As for the administration route, it is preferred to select the most effective route of the administration. Examples of the administration route include oral administration, or parenteral administration such as intravenous administration.

Examples of the dosage form include a tablet, injection, and the like.

Suitable dosage forms for the oral administration, for example, such as tablets, can be produced by using excipients such as lactose, disintegrators such as starch, lubricants such as magnesium stearate, binders such as hydroxypropyl cellulose, and the like.

Suitable dosage forms for the parenteral administration, for example, such as injections can be produced by using a diluent or a solvent, such as a salt solution, a glucose solution, or a mixture of brine and a glucose solution, and the like.

The doses and the frequencies of the administration of Compound (I) or a pharmaceutically acceptable salt thereof may vary depending upon dosage form, age and body weight of a patient, nature or seriousness of the symptom to be treated, and the like. In the oral administration, in general, a dose of 0.01 mg to 1,000 mg, preferably, 0.05 to 100 mg, is administered to an adult patient once or several times a day. In parenteral administration such as intravenous administration, a dose of 0.001 mg to 1,000 mg, preferably, 0.01 to 100 mg, is administered to an adult patient once or several times a day. However, these doses and frequencies of administration vary by the various conditions described above.

The present invention is described below in greater detail using Reference Examples and Examples. It should be noted that the scope of the invention is not limited by the following Examples.

Note that the proton nuclear magnetic resonance spectra ($^1$H NMR) used in Reference Examples and Examples were measured at 270 MHz or 300 MHz, and exchangeable protons may not be clearly observed depending on the compound and measurement conditions. Common notation is used to represent signal multiplicity. The symbol br denotes apparently wide signal. ChemBioDraw Ultra ver. 11.0.1 was used for nomenclature of compounds.

Reference Example 1

9-Bromo-4H-pyrido[1,2-a]pyrimidin-4-one
(Compound a)

Commercially available 2-amino-3-bromopyridine (2.00 g, 11.6 mmol) was dissolved in ethanol (100 mL), and Meldrum's acid (1.83 g, 12.7 mmol) and trimethyl orthoformate (1.26 mL, 11.6 mmol) were added. The mixture was stirred for 1.5 hours while evaporating methanol at 100° C. The reaction mixture was cooled to room temperature, crystallized from ethanol, and collected by filtration to give 5-[(3-bromopyridin-2-ylamino)methylene]-2,2-dimethyl-[1,3]dioxane-4,6-dione (0.890 g, 23%).

5-[(3-Bromopyridin-2-ylamino)methylene]-2,2-dimethyl-[1,3]dioxane-4,6-dione (860 mg, 2.63 mmol) was dissolved in diphenyl ether (12 mL), and the mixture was stirred at 260° C. for 15 minutes using a mantle heater. The reaction mixture was cooled to room temperature, and hexane was added. The precipitated crystals were then collected by filtration to give Compound a (420 mg, 71%).

ESI-MS: m/z 225, 227 [M+H]$^+$. $^1$H-NMR (CDCl$_3$) δ (ppm): 6.52 (d, J=6.6 Hz, 1H), 7.04 (dd, J=7.3, 7.3 Hz, 1H), 8.13 (dd, J=1.5, 7.3 Hz, 1H), 8.41 (d, J=6.6 Hz, 1H), 9.09 (dd, J=1.5, 7.3 Hz, 1H).

Reference Example 2

9-Bromo-2-methyl-4H-pyrido[1,2-a]pyrimidin-4-one
(Compound b)

Polyphosphoric acid (50.0 g) and ethyl acetoacetate (2.64 mL, 20.8 mmol) were added to commercially available 2-amino-3-bromopyridine (3.00 g, 17.3 mmol), and the mixture was stirred at 100° C. for 3 hours. The reaction mixture was poured into ice water, and neutralized with a 4.0 mol/L sodium hydroxide aqueous solution. The precipitated crystals were collected by filtration, and dried overnight under reduced pressure to give Compound b (2.94 g, 71%).

ESI-MS: m/z 239, 241 [M+H]$^+$. $^1$H-NMR (CDCl$_3$) δ (ppm): 2.53 (s, 3H), 6.37 (s, 1H), 6.95 (dd, J=7.3, 7.3 Hz, 1H), 8.06 (dd, J=1.3, 7.3 Hz, 1H), 9.01 (dd, J=1.3, 7.3 Hz, 1H).

Reference Example 3

9-Bromo-2-ethyl-4H-pyrido[1,2-a]pyrimidin-4-one
(Compound c)

Polyphosphoric acid (35.0 g) and ethyl propionylacetate (2.14 mL, 15.0 mmol) were added to commercially available 2-amino-3-bromopyridine (2.00 g, 11.6 mmol), and the mixture was stirred at 100° C. for 4.5 hours. The reaction mixture was poured into ice water, neutralized with a 4.0 mol/L sodium hydroxide aqueous solution, and extracted with ethyl acetate. The organic layer was dried over anhydrous magnesium sulfate, and concentrated under reduced pressure. The obtained residue was then purified by silica gel column chromatography (hexane/ethyl acetate=2/1) to give Compound c (2.02 g, 69%).

ESI-MS: m/z 253, 255 [M+H]$^+$. $^1$H-NMR (CDCl$_3$) δ (ppm): 1.34 (t, J=7.3 Hz, 3H), 2.78 (q, J=7.3 Hz, 2H), 6.38 (s, 1H), 6.92 (dd, J=7.3, 7.3 Hz, 1H), 8.04 (dd, J=1.6, 7.3 Hz, 1H), 8.99 (dd, J=1.6, 7.3 Hz, 1H).

Reference Example 4

9-Bromo-2,3-dimethyl-4H-pyrido[1,2-a]pyrimidin-4-one (Compound d)

Commercially available 2-amino-3-bromopyridine (24.0 g, 139 mmol) was added to polyphosphoric acid (75.0 mL) heated to 100° C., and ethyl 2-methyl-3-oxobutanoate (29.4 mL, 208 mmol) was added in three separate portions. The mixture was then stirred at 100° C. for 4 hours. The reaction mixture was poured into ice water, neutralized with a 6.0 mol/L sodium hydroxide aqueous solution, and extracted with ethyl acetate. The organic layer was washed with saturated brine, dried over anhydrous magnesium sulfate, and concentrated under reduced pressure. The obtained residue was then reslurried in diisopropyl ether to give Compound d (27.1 g, 77%).

ESI-MS: m/z 253, 255 [M+H]$^+$. $^1$H-NMR (CDCl$_3$) δ (ppm): 2.27 (s, 3H), 2.56 (s, 3H), 6.90 (dd, J=7.3, 7.3 Hz, 1H), 7.97 (dd, J=1.3, 7.3 Hz, 1H), 8.98 (dd, J=1.3, 7.3 Hz, 1H).

Reference Example 5

8-Bromo-3-methyl-3H-quinazolin-4-one (Compound e)

Commercially available 7-bromoisatin (18.0 g, 79.6 mmol) was dissolved in a 5% sodium hydroxide aqueous solution (400 mL), and 30% hydrogen peroxide water (22.5 mL, 199 mmol) was dropped at 50° C. The mixture was stirred at 50° C. for 30 minutes. The reaction mixture was cooled to room temperature, and neutralized with 2.0 mol/L hydrochloric acid. The precipitated crystals were collected by filtration, and dried overnight under reduced pressure to give 2-amino-3-bromobenzoic acid (16.9 g, 98%).

2-Amino-3-bromobenzoic acid (16.9 g, 78.0 mmol) was suspended in THF (170 mL), and 1,1'-carbonyldiimidazole (19.0 g, 117 mmol) was added. The mixture was stirred at 70° C. for 2 hours. After cooling the reaction mixture to room temperature, a 2.0 mol/L methylamine/THF solution (78.0 mL, 156 mmol) was added, and the mixture was stirred at 70° C. for 2 hours. The reaction mixture was cooled to room temperature, then concentrated under reduced pressure, and the obtained residue was dissolved in ethyl acetate. The resulting solution was washed with a 1.0 mol/L sodium hydroxide aqueous solution, a 5% citric acid aqueous solution, and saturated brine. The organic layer was dried over anhydrous magnesium sulfate, and concentrated under reduced pressure to give 2-amino-3-bromo-N-methylbenzamide (18.4 g, quantitative yield).

2-Amino-3-bromo-N-methylbenzamide (18.4 g, 78.0 mol) was dissolved in NMP (180 mL), and trimethyl orthoformate (38.4 mL, 351 mmol) and a 4.0 mol/L hydrogen chloride/1,4-dioxane solution (10.0 mL, 39.0 mmol) were added. The mixture was stirred at 110° C. for 1.5 hours. The reaction mixture was cooled to room temperature, poured into ice water, and neutralized with a saturated sodium bicarbonate aqueous solution. The mixture was extracted twice with ethyl acetate. The organic layer was washed with water and saturated brine, dried over anhydrous magnesium sulfate, and concentrated under reduced pressure. The obtained residue was reslurried in diisopropyl ether to give Compound e (16.0 g, 86%).

ESI-MS: m/z 239, 241 [M+H]$^+$. $^1$H-NMR (CDCl$_3$) δ: 3.62 (s, 3H), 7.37 (dd, J=7.9, 8.1 Hz, 1H), 8.04 (dd, J=7.9, 1.3 Hz, 1H), 8.16 (s, 1H), 8.29 (dd, J=8.1, 1.5 Hz, 1H).

Reference Example 6

8-Bromo-2,3-dimethyl-3H-quinazolin-4-one (Compound f)

2-Amino-3-bromobenzoic acid (850 mg, 3.93 mmol) obtained in Reference Example 5 was dissolved in acetic anhydride (3.7 mL, 39.3 mmol), and the solution was stirred at 100° C. for 1.25 hours. The reaction mixture was concentrated, and azeotropically distilled twice with toluene to give 8-bromo-2-methyl-4H-benzo[d][1,3]oxazin-4-one (0.944 g, quantitative yield).

8-Bromo-2-methyl-4H-benzo[d][1,3]oxazin-4-one (0.944 g, 3.93 mmol) was dissolved in THF (20 mL), and a 2.0 mol/L methylamine/THF solution (19.7 mL, 39.3 mmol) was added. The mixture was stirred at 70° C. for 1 hour. After concentrating the reaction mixture, the obtained residue was purified by silica gel column chromatography (hexane/ethyl acetate=4/1) to give Compound f (0.661 g, 66%).

ESI-MS: m/z 253, 255 [M+H]$^+$. $^1$H-NMR (CDCl$_3$) δ (ppm): 2.67 (s, 3H), 3.62 (s, 3H), 7.27 (dd, J=7.9, 7.9 Hz, 1H), 7.98 (dd, J=1.3, 7.9 Hz, 1H), 8.20 (dd, J=1.3, 7.9 Hz, 1H).

Reference Example 7

8-Bromo-3-ethyl-3H-quinazolin-4-one (Compound g)

2-Amino-3-bromobenzoic acid (800 mg, 3.70 mmol) obtained in Reference Example 5 was dissolved in THF (40 mL), and 1,1'-carbonyldiimidazole (901 mg, 5.55 mmol) was added. The mixture was stirred at 70° C. for 1.5 hours. The reaction mixture was cooled to room temperature, and a 2.0 mol/L ethylamine/THF solution (3.70 mL, 7.41 mmol) was added. The mixture was stirred at 70° C. for 2 hours. The reaction mixture was cooled to room temperature, and concentrated under reduced pressure. The obtained residue was dissolved in ethyl acetate. The resulting solution was washed with a 1.0 mol/L sodium hydroxide aqueous solution, a 5% citric acid aqueous solution, and saturated brine. The organic layer was dried over anhydrous magnesium sulfate, and concentrated under reduced pressure to give 2-amino-3-bromo-N-ethylbenzamide (883 mg, 98%).

2-Amino-3-bromo-N-ethylbenzamide (883 mg, 3.63 mol) was dissolved in NMP (12 mL), and trimethyl orthoformate (4.0 mL) and a 4.0 mol/L hydrogen chloride/1,4-dioxane solution (0.80 mL) were added. The mixture was stirred at 110° C. for 1.5 hours. The reaction mixture was cooled to room temperature, poured into ice water, and neutralized with a saturated sodium bicarbonate aqueous solution. The mixture was extracted with ethyl acetate, and the organic layer was washed with saturated brine. The product was dried over anhydrous magnesium sulfate, and concentrated under reduced pressure to give Compound g (803 mg, 87%).

ESI-MS: m/z 253, 255 [M+H]$^+$. $^1$H-NMR (CDCl$_3$) δ (ppm): 1.45 (t, J=7.3 Hz, 3H), 4.10 (q, J=7.3 Hz, 2H), 7.38 (dd, J=7.9, 7.9 Hz, 1H), 8.05 (dd, J=1.3, 7.9 Hz, 1H), 8.19 (s, 1H), 8.30 (dd, J=1.3, 7.9 Hz, 1H).

Reference Example 8

5-Bromo-3-methyl-3H-quinazolin-4-one (Compound h)

Commercially available 4-bromoisatin (2.50 g, 11.1 mmol) was dissolved in a 1.5 mol/L sodium hydroxide aqueous solution (20 mL), and 33% hydrogen peroxide water (1 mL) was dropped at 55° C. After being stirred at 55° C. for 30 minutes, the reaction mixture was cooled to room temperature, neutralized with 2.0 mol/L hydrochloric acid, and purified with HP-20 resin to give 2-amino-6-bromobenzoic acid (1.60 g, 67%).

2-Amino-6-bromobenzoic acid (1.60 g, 7.41 mmol) was dissolved in DMF (40 mL), and methylamine hydrochloride (1.50 g, 22.2 mmol), triethylamine (3.10 mL, 22.2 mmol), 1-(3-dimethylaminopropyl)-3-ethylcarbodiimide.hydrochloride (2.84 g, 14.8 mmol), and 1-hydroxybenzotriazole- .hydrate (2.27 g, 14.8 mmol) were added. The mixture was stirred overnight at room temperature. The reaction mixture was diluted by adding ethyl acetate, and washed with water, a saturated sodium bicarbonate aqueous solution, and saturated brine. The organic layer was dried over anhydrous magnesium sulfate, and concentrated under reduced pressure. The obtained residue was then purified by silica gel column chromatography (hexane/ethyl acetate=2/1) to give 2-amino-6-bromo-N-methylbenzamide (0.781 g, 46%).

2-Amino-6-bromo-N-methylbenzamide (0.780 g, 3.41 mmol) was dissolved in NMP (12 mL), and trimethyl orthoformate (4.0 mL) and 4.0 mol/L hydrogen chloride/1,4-dioxane solution (0.80 mL) were added. The mixture was stirred at 110° C. for 2.5 hours. The reaction mixture was cooled to room temperature, poured into ice water, and neutralized with a saturated sodium bicarbonate aqueous solution. The mixture was extracted with ethyl acetate. The organic layer was washed with saturated brine, dried over anhydrous magnesium sulfate, and concentrated under reduced pressure. The obtained residue was then purified by silica gel column chromatography (chloroform) to give Compound h (0.490 g, 60%).

ESI-MS: m/z 239, 241 [M+H]$^+$. $^1$H-NMR (CDCl$_3$) δ (ppm): 3.54 (s, 3H), 7.48 (dd, J=7.9, 8.3 Hz, 1H), 7.62 (dd, J=1.3, 8.3 Hz, 1H), 7.71 (dd, J=1.3, 7.9 Hz, 1H), 8.04 (s, 1H).

Reference Example 9

5-Bromo-2-methylisoquinolin-1-one (Compound j)

Commercially available 5-bromoisoquinoline (1.09 g, 5.24 mmol) was dissolved in dichloromethane (20 mL), and m-CPBA (2.09 g, 7.86 mmol) was added. The mixture was stirred at room temperature for 0.5 hours. The reaction mixture was diluted by adding chloroform, and washed with a saturated sodium bicarbonate aqueous solution and saturated brine. The organic layer was dried over anhydrous magnesium sulfate, and concentrated under reduced pressure. The obtained residue was dissolved in acetic anhydride (18 mL), and stirred for 3 hours under heat and reflux. A 2.0 mol/L sodium hydroxide aqueous solution (36 mL) was added to the residue obtained by concentrating the reaction mixture under reduced pressure, and the mixture was stirred for 1 hour under reflux. After extracting the reaction mixture with chloroform, the organic layer was dried over anhydrous magnesium sulfate, and concentrated under reduced pressure. The obtained residue was dissolved in DMF (26 mL), and potassium carbonate (2.89 g, 20.9 mmol) and methyl iodide (0.978 mL, 15.7 mmol) were added. The mixture was stirred at room temperature for 3.5 hours. The reaction mixture was extracted with ethyl acetate after adding water. The organic layer was dried over anhydrous magnesium sulfate, and concentrated under reduced pressure. The obtained residue was then purified by silica gel column chromatography (hexane/ethyl acetate=1/1) to give Compound j (0.355 g, 4 steps 28%).

ESI-MS: m/z 238, 240 [M+H]$^+$. $^1$H-NMR (CDCl$_3$) δ (ppm): 3.61 (s, 3H), 6.83 (d, J=7.9 Hz, 1H), 7.16 (d, J=7.9 Hz, 1H), 7.32 (dd, J=7.9, 7.9 Hz, 1H), 7.87 (d, J=8.1 Hz, 1H), 8.41 (d, J=8.1 Hz, 1H).

Reference Example 10

8-Bromo-2-methylisoquinolin-1(2H)-one (Compound k)

Compound k (297 mg, 48%) was obtained in the same manner as in Reference Example 9, using commercially available 8-bromoisoquinoline (547 mg, 2.63 mmol) instead of 5-bromoisoquinoline.

ESI-MS: m/z 239 [M+H]$^+$. $^1$H-NMR (CDCl$_3$) δ (ppm): 3.57 (s, 3H), 6.43 (d, J=7.3 Hz, 1H), 7.11 (d, J=7.3 Hz, 1H), 7.36 (t, J=7.9 Hz, 1H), 7.44 (dd, J=7.9, 1.5 Hz, 1H), 7.74 (dd, J=7.9, 1.5 Hz, 1H).

Reference Example 11

5-Bromo-1-methylquinolin-2(1H)-one (Compound m)

Compound m (252 mg, 44%) was obtained in the same manner as in Reference Example 9, using commercially available 5-bromoquinoline (500 mg, 2.40 mmol) instead of 5-bromoisoquinoline.

ESI-MS: m/z 239 [M+H]$^+$. $^1$H-NMR (CDCl$_3$) δ (ppm): 3.62 (s, 3H), 6.83 (d, J=7.7 Hz, 1H), 7.17 (d, J=7.7 Hz, 1H), 7.33 (t, J=7.9 Hz, 1H), 7.87 (dd, J=7.7, 1.1 Hz, 1H), 8.41 (dt, J=7.9, 1.1 Hz, 1H).

Reference Example 12

(S)-9-Methylamino-5-(1-methylindoline-2,3-dion-4-yl)-1,2,3,3a,4,5-hexahydro-5,8,10,10b-tetraazabenzo[e]azulen-6-one (Compound 1-146)

Compound 1-146 was obtained in the same manner as in Example 146 of WO2008/149834.

Reference Example 13

8-Bromo-3-(2-methoxyethyl)quinazolin-4(3H)-one (Compound aa)

THF (28 mL) and 1,1'-carbonyldiimidazole (976 mg, 6.02 mmol) were added to 2-amino-3-bromobenzoic acid (1 g, 4.63 mmol) obtained in Reference Example 5. The mixture was stirred for 30 minutes under reflux, and cooled to room temperature. After adding 2-methoxyethylamine (0.805 mL, 9.26 mmol), the mixture was stirred overnight at room temperature. The reaction mixture was concentrated under reduced pressure, and the obtained residue was dissolved in ethyl acetate, and washed with a 1 mol/L sodium hydroxide aqueous solution, a 10% citric acid aqueous solution, and saturated brine. The organic layer was dried over anhydrous sodium sulfate, and concentrated under reduced pressure to give 2-amino-3-bromo-N-(2-methoxyethyl)benzamide (1.22 g, 96%).

2-Amino-3-bromo-N-(2-methoxyethyl)benzamide (1.22 g, 4.47 mmol) above was dissolved in NMP (12 mL), and trimethyl orthoformate (2.47 mL, 22.3 mmol) and a 4 mol/L hydrogen chloride/dioxane solution (0.588 mL, 2.23 mmol) were added. The mixture was stirred at 110° C. for 2 hours. After cooling the reaction mixture to room temperature, a saturated sodium bicarbonate aqueous solution was added, and the mixture was extracted with ethyl acetate. The organic layer was washed with water and saturated brine, dried over sodium sulfate, and concentrated under reduced pressure. The obtained residue was recrystallized from heptane/toluene to give Compound aa (1.11 g, 88%).

ESI-MS: m/z 283 [M+H]$^+$. $^1$H-NMR (CDCl$_3$) δ (ppm): 8.28 (dd, J=8.1, 1.5 Hz, 1H), 8.22 (s, 1H), 8.04 (dd, J=7.7, 1.5 Hz, 1H), 7.35 (dd, J=7.9, 7.8 Hz, 1H), 4.19 (t, J=4.8 Hz, 2H), 3.67 (t, J=4.8 Hz, 2H), 3.32 (s, 3H).

Reference Example 14

8-Bromo-3-(3-methoxypropyl)quinazolin-4(3H)-one (Compound ab)

Compound ab was obtained in the same manner as in Reference Example 13, using 3-methoxypropylamine.

ESI-MS: m/z 297 [M+H]$^+$. $^1$H-NMR (CDCl$_3$) δ (ppm): 8.28 (dd, J=8.1, 1.5 Hz, 1H), 8.17 (s, 1H), 8.03 (dd, J=7.7, 1.5 Hz, 1H), 7.36 (dd, J=7.9, 7.9 Hz, 1H), 4.13 (t, J=6.6 Hz, 2H), 3.40 (t, J=5.9 Hz, 2H), 3.35 (s, 3H), 2.07 (tt, J=5.9, 5.9 Hz, 2H).

Reference Example 15

8-Bromo-3-(3-(dimethylamino)propyl)quinazolin-4(3H)-one (Compound ac)

Compound ac was obtained in the same manner as in Reference Example 13, using N,N-dimethylpropane-1,3-diamine.

ESI-MS: m/z 310 [M+H]$^+$. $^1$H-NMR (CDCl$_3$) δ (ppm): 8.28 (d, J=7.8 Hz, 1H), 8.24 (s, 1H), 8.03 (d, J=7.8 Hz, 1H), 7.35 (dd, J=7.8, 7.9 Hz, 1H), 4.09 (t, J=6.8 Hz, 2H), 2.30 (t, J=6.3 Hz, 2H), 2.21 (s, 6H), 2.00-1.89 (m, 2H).

Reference Example 16

8-Bromo-3-(2-(dimethylamino)ethyl)quinazolin-4(3H)-one (Compound ad)

Compound ad was obtained in the same manner as in Reference Example 13, using N,N-dimethylethylenediamine.

ESI-MS: m/z 296 [M+H]$^+$. $^1$H-NMR (CDCl$_3$) δ (ppm): 8.28 (d, J=7.8 Hz, 1H), 8.20 (s, 1H), 8.03 (d, J=7.8 Hz, 1H), 7.35 (dd, J=8.3, 8.3 Hz, 1H), 4.08 (t, J=5.9 Hz, 2H), 2.64 (t, J=5.9 Hz, 2H), 2.27 (s, 6H).

Reference Example 17

8-Bromo-3-(2-hydroxy-2-methylpropyl)quinazolin-4(3H)-one (Compound ae)

Compound ae was obtained in the same manner as in Reference Example 13, using 1-amino-2-methylpropan-2-ol.

ESI-MS: m/z 297 [M+H]$^+$. $^1$H-NMR (CDCl$_3$) δ (ppm): 8.31 (s, 1H), 8.25 (d, J=8.8 Hz, 1H), 8.03 (d, J=7.8 Hz, 1H), 7.35 (dd, J=7.8, 7.8 Hz, 1H), 4.09 (s, 2H), 2.64 (s, 1H), 1.31 (s, 6H).

Reference Example 18

8-Bromo-3-cyclopropyl-3H-quinazolin-4-one (Compound af)

Compound af was obtained in the same manner as in Reference Example 13, using cyclopropylamine.

ESI-MS: m/z 265, 267 [M+H]$^+$. $^1$H-NMR (CDCl$_3$) δ (ppm): 0.93 (m, 2H), 1.23 (m, 2H), 3.27 (m, 1H), 7.36 (dd, J=7.9, 7.9 Hz, 1H), 8.03 (dd, J=1.3, 7.9 Hz, 1H), 8.23 (s, 1H), 8.28 (dd, J=1.3, 7.9 Hz, 1H).

Reference Example 19

8-Bromo-3-(2-fluoroethyl)-3H-quinazolin-4-one (Compound ag)

Compound ag was obtained in the same manner as in Reference Example 13, using 2-fluoroethylamine hydrochloride.

ESI-MS: m/z 271, 273 [M+H]$^+$. $^1$H-NMR (CDCl$_3$) δ (ppm): 4.33 (dt, J=3.9, 27.3 Hz, 2H), 4.74 (dt, J=3.9, 46.8 Hz, 2H), 7.39 (dd, J=7.8, 7.8 Hz, 1H), 8.06 (dd, J=1.9, 7.8 Hz, 1H), 8.18 (s, 1H), 8.28 (dd, J=1.9, 7.8 Hz, 1H).

Reference Example 20

8-Bromo-3-(2,2-difluoroethyl)-3H-quinazolin-4-one (Compound ah)

Compound ah was obtained in the same manner as in Reference Example 13, using 2,2-difluoroethylamine.

ESI-MS: m/z 289, 291 [M+H]$^+$. $^1$H-NMR (CDCl$_3$) δ (ppm): 4.35 (dt, J=4.4, 13.6 Hz, 2H), 6.14 (dt, J=4.0, 55.7 Hz, 1H), 7.41 (dd, J=7.7, 8.1 Hz, 1H), 8.08 (dd, J=1.5, 7.7 Hz, 1H), 8.13 (s, 1H), 8.28 (dd, J=1.5, 8.1 Hz, 1H).

Reference Example 21

8-Bromo-3-(2,2,2-trifluoroethyl)-3H-quinazolin-4-one (Compound ai)

Compound ai was obtained in the same manner as in Reference Example 13, using 2,2,2-trifluoroethylamine.

ESI-MS: m/z 307, 309 [M+H]$^+$. $^1$H-NMR (CDCl$_3$) δ (ppm): 4.69 (q, J=8.8 Hz, 2H), 7.42 (dd, J=7.7, 7.7 Hz, 1H), 8.09 (dd, J=1.5, 7.7 Hz, 1H), 8.16 (s, 1H), 8.31 (dd, J=1.5, 7.7 Hz, 1H).

Reference Example 22

8-Bromo-3-ethyl-2-trifluoromethyl-3H-quinazolin-4-one (Compound aj)

2-Amino-3-bromobenzoic acid (1.00 g, 4.63 mmol) obtained in Reference Example 5 was dissolved in acetonitrile (15 mL), and pyridine (1.872 mL, 23.1 mmol) was added. After cooling the mixture to 0° C., anhydrous trifluoroacetic acid (1.96 mL, 13.9 mmol) was added, and the mixture was stirred at room temperature for 4 hours. The reaction mixture was concentrated under reduced pressure, and the obtained residue was purified by silica gel column chromatography (chloroform/methanol=9/1) to give 8-bromo-2-trifluoromethyl-4H-benzo[d][1,3]oxazin-4-one (0.93 g, 68%).

8-Bromo-2-trifluoromethyl-4H-benzo[d][1,3]oxazin-4-one (0.80 g, 2.72 mmol) was dissolved in THF (18 mL), and a 2.0 mol/L ethylamine/THF solution (6.80 mL, 13.6 mmol) was added. The mixture was stirred at 70° C. for 22 hours. The reaction mixture was concentrated under reduced pressure, and the obtained residue was purified by silica gel column chromatography (heptane/ethyl acetate=4/1) to give Compound aj (0.763 g, 87%).

ESI-MS: m/z 321, 323 [M+H]⁺. ¹H-NMR (CDCl₃) δ (ppm): 1.41 (t, J=6.8 Hz, 3H), 4.26 (q, J=6.8 Hz, 2H), 7.46 (dd, J=7.8. 7.8 Hz, 1H), 8.09 (dd, J=1.9, 7.8 Hz, 1H), 8.29 (dd, J=1.9, 7.8 Hz, 1H).

Reference Example 23

8-Bromo-3-methyl-2-trifluoromethyl-3H-quinazolin-4-one (Compound ak)

8-Bromo-2-trifluoromethyl-4H-benzo[d][1,3]oxazin-4-one (0.50 g, 1.70 mmol) obtained in Reference Example 22 was dissolved in THF (11 mL), and a 2.0 mol/L methylamine/THF solution (4.25 mL, 8.50 mmol) was added. The mixture was stirred at 70° C. for 22 hours. The reaction mixture was concentrated under reduced pressure, and the obtained residue was purified by silica gel column chromatography (heptane/ethyl acetate=4/1) to give Compound ak (0.465 g, 89%).
ESI-MS: m/z 307, 309 [M+H]⁺. ¹H-NMR (CDCl₃) δ (ppm): 3.74 (s, 3H), 7.47 (dd, J=7.7. 8.1 Hz, 1H), 8.10 (dd, J=1.5, 7.7 Hz, 1H), 8.30 (dd, J=1.5, 8.1 Hz, 1H).

Reference Example 24

8-Bromo-3-(2-fluoroethyl)-2-methyl-3H-quinazolin-4-one (Compound al)

8-Bromo-2-methyl-4H-benzo[d][1,3]oxazin-4-one (0.477 g, 1.99 mmol) obtained in Reference Example 6 was dissolved in THF (13 mL), and 2-fluoroethylamine hydrochloride (0.989 g, 9.94 mmol) and triethylamine (1.94 mL, 13.9 mmol) were added. The mixture was stirred at 70° C. for 20 hours. The reaction mixture was concentrated under reduced pressure, and the obtained residue was purified by silica gel column chromatography (heptane/ethyl acetate=3/1) to give Compound al (0.201 g, 36%).
ESI-MS: m/z 285, 287 [M+H]⁺. ¹H-NMR (CDCl₃) δ (ppm): 2.75 (s, 3H), 4.44 (dt, J=4.9, 25.4 Hz, 2H), 4.77 (dt, J=4.9, 47.8 Hz, 2H), 7.30 (dd, J=7.8, 7.8 Hz, 1H), 8.02 (dd, J=1.9, 7.8 Hz, 1H), 8.21 (dd, J=1.9, 7.8 Hz, 1H).

Reference Example 25

8-Bromo-3-(2,2-difluoroethyl)-2-methyl-3H-quinazolin-4-one (Compound am)

8-Bromo-2-methyl-4H-benzo[d][1,3]oxazin-4-one (0.500 g, 2.08 mmol) obtained in Reference Example 6 was dissolved in THF (14 mL), and 2,2-difluoroethylamine (0.600 g, 8.51 mmol) was added. The mixture was stirred at 70° C. for 2 days. The reaction mixture was concentrated under reduced pressure, and the obtained residue was purified by silica gel column chromatography (heptane/ethyl acetate=4/1) to give Compound am (0.157 g, 25%).
ESI-MS: m/z 303, 305 [M+H]⁺.

Reference Example 26

8-Bromo-3-(2-(tert-butyldimethylsiloxy)ethyl)-3H-quinazolin-4-one (Compound an)

2-Amino-3-bromobenzoic acid (1.50 g, 6.94 mmol) obtained in Reference Example 5 was dissolved in THF (69 mL), and 1,1'-carbonyldiimidazole (1.35 g, 8.33 mmol) was added. The mixture was stirred at 70° C. for 2 hours. The reaction mixture was cooled to room temperature, and 2-aminoethanol (1.26 mL, 20.8 mmol) was added. The mixture was stirred at 70° C. for 4 hours. The reaction mixture was cooled to room temperature, and concentrated under reduced pressure. The obtained residue was dissolved in ethyl acetate, and washed with a 1.0 mol/L sodium hydroxide aqueous solution, a 5% citric acid aqueous solution, and saturated brine. The organic layer was dried over anhydrous magnesium sulfate, and concentrated under reduced pressure to give 2-amino-3-bromo-N-(2-hydroxyethyl)benzamide (1.59 g, 88%).
2-Amino-3-bromo-N-(2-hydroxyethyl)benzamide (1.83 g, 7.06 mmol) was dissolved in NMP (23.5 mL), and trimethyl orthoformate (7.7 mL) and a 4.0 mol/L hydrogen chloride/1,4-dioxane solution (8.8 mL) were added. The mixture was stirred at 110° C. for 3 hours. The reaction mixture was cooled to room temperature, poured into ice water, and neutralized with a saturated sodium bicarbonate aqueous solution. The mixture was then extracted once with ethyl acetate. The organic layer was washed with saturated brine, dried over anhydrous magnesium sulfate, and concentrated under reduced pressure. The obtained residue was purified by silica gel column chromatography (chloroform/methanol=20/1) to give 8-bromo-3-(2-hydroxyethyl)-3H-quinazolin-4-one (1.90 g, quantitative).
ESI-MS: m/z 269, 271 [M+H]⁺. ¹H-NMR (CDCl₃) δ (ppm): 2.50 (br s, 1H), 4.00 (dt, J=4.8, 4.8 Hz, 2H), 4.18 (t, J=4.8 Hz, 2H), 7.33 (dd, J=7.7, 7.7 Hz, 1H), 8.00 (dd, J=1.5, 7.7 Hz, 1H), 8.22 (s, 1H), 8.23 (dd, J=1.5, 7.7 Hz, 1H).
Subsequently, 8-Bromo-3-(2-hydroxyethyl)-3H-quinazolin-4-one (2.10 g, 7.80 mmol) was dissolved in DMF (78 mL), and cooled to 0° C. After adding tert-butylchlorodimethylsilane (2.35 g, 15.6 mmol) and imidazole (2.13 g, 31.2 mmol), the mixture was stirred at room temperature for 1.5 hours. The reaction mixture was diluted with ethyl acetate, and washed with water and saturated brine. The organic layer was dried over anhydrous magnesium sulfate, and concentrated under reduced pressure. The obtained residue was purified by silica gel column chromatography (ethyl acetate) to give Compound an (2.29 g, quantitative).
ESI-MS: m/z 383, 385 [M+H]⁺. ¹H-NMR (CDCl₃) δ (ppm): 0.02 (s, 3H), 0.05 (s, 3H), 0.89 (s, 9H), 3.97 (t, J=4.9 Hz, 2H), 4.18 (t, J=4.9 Hz, 2H), 7.41 (dd, J=7.8, 7.8 Hz, 1H), 8.09 (dd, J=1.9, 7.8 Hz, 1H), 8.25 (s, 1H), 8.34 (dd, J=1.9, 7.8 Hz, 1H).

Reference Example 27

8-Bromo-2-methoxymethyl-3-methyl-3H-quinazolin-4-one (Compound ao)

Pyridine (0.883 mL, 10.9 mmol) and 2-methoxyacetylchloride (0.438 mL, 4.80 mmol) were added to 2-amino-3-bromo-N-methylbenzamide (0.500 g, 2.18 mmol) obtained in Reference Example 5, and the mixture was stirred at room temperature for 2.5 hours. After making the reaction mixture acidic by addition of 2 mol/L hydrochloric acid, the mixture was extracted twice with ethyl acetate. The organic layer was washed with saturated brine, dried over anhydrous magnesium sulfate, and concentrated under reduced pressure. The obtained residue was purified by silica gel column chromatography (chloroform/methanol=12/1) to give 3-bromo-2-(2-methoxyacetamido)-N-methylbenzamide (0.380 g, 58%).
3-Bromo-2-(2-methoxyacetamido)-N-methylbenzamide (0.380 g, 1.26 mmol) was dissolved in acetic acid (30 mL), and concentrated sulfuric acid (1.1 mL) was added. The mixture was stirred at 100° C. for 6 hours. The reaction mixture was concentrated under reduced pressure, neutralized with a saturated sodium bicarbonate aqueous solution, and extracted three times with chloroform. The organic layer was washed with saturated brine, dried over anhydrous magnesium sulfate, and concentrated under reduced pressure. The obtained residue was purified by silica gel column chromatography (heptane/ethyl acetate=4/1) to give Compound ao (0.283 g, 79%).

ESI-MS: m/z 283, 285 [M+H]$^+$. $^1$H-NMR (CDCl$_3$) δ (ppm): 3.50 (s, 3H), 3.69 (s, 3H), 4.62 (s, 2H), 7.32 (dd, J=7.7, 7.7 Hz, 1H), 8.00 (dd, J=1.5, 7.7 Hz, 1H), 8.22 (dd, J=1.5, 7.7 Hz, 1H).

Reference Example 28

8-Bromo-3-methyl-3H-pyrido[4,3-d]pyrimidin-4-one (Compound ap)

4-Aminonicotinic acid (5.0 g, 36.2 mmol) was suspended in acetic acid (90 mL), and a solution of bromine (3.73 mL, 72.4 mmol) in acetic acid (27 mL) was added. The mixture was stirred at room temperature for 2 hours. The reaction mixture was diluted with diethyl ether, and the solid was collected by filtration, and dried under reduced pressure. The resulting solid was dissolved in formamide (20 mL), and the solution was stirred at 180° C. for 5 hours. After cooling the reaction mixture to room temperature, water was added, and the mixture was extracted with ethyl acetate. The organic layer was washed with saturated brine, dried over anhydrous magnesium sulfate, and concentrated under reduced pressure. The obtained residue was reslurried in ethyl acetate to give 8-bromo-3 methyl-3H-pyrido[4,3-d]pyrimidin-4-one (1.02 g, 13%).

8-Bromo-3-methyl-3H-pyrido[4,3-d]pyrimidin-4-one (1.02 g, 4.51 mmol) was dissolved in DMF (23 mL), and 60% sodium hydride (0.361 g, 9.03 mmol) was added at 0° C. The mixture was stirred at 0° C. for 15 minutes. After adding methyl iodide (1.13 mL, 18.1 mmol), and stirring the mixture at room temperature for 3 hours, the reaction was quenched by addition of a saturated ammonium chloride aqueous solution. After extracting the reaction mixture with ethyl acetate, the organic layer was washed with saturated brine, dried over anhydrous magnesium sulfate, and concentrated under reduced pressure. The obtained residue was purified by silica gel column chromatography (heptane/ethyl acetate=1/3) to give Compound ap (0.270 g, 25%).

ESI-MS: m/z 240, 242 [M+H]$^+$. $^1$H-NMR (CDCl$_3$) δ (ppm): 3.64 (s, 3H), 8.30 (s, 1H), 9.03 (s, 1H), 9.43 (s, 1H).

Reference Example 29

9-Bromo-2-trifluoromethyl-4H-pyrido[1,2-a]pyrimidin-4-one (Compound aq)

Commercially available 2-amino-3-bromopyridine (965 mg, 5.41 mmol), and ethyl 4,4,4-trifluoro-3-oxobutanoate (2.11 mL, 14.0 mmol) were added to polyphosphoric acid (45 g) heated to 100° C., and the mixture was stirred at 100° C. for 4 hours. The reaction mixture was poured into ice water, neutralized with a 3.0 mol/L sodium hydroxide aqueous solution, and extracted with ethyl acetate. The organic layer was dried over anhydrous magnesium sulfate, and concentrated under reduced pressure. The obtained residue was purified by silica gel column chromatography (ethyl acetate) to give Compound aq (192 mg, 12%).

ESI-MS: m/z 293, 295 [M+H]$^+$. $^1$H-NMR (CDCl$_3$) δ (ppm): 6.78 (dd, J=7.3, 7.3 Hz, 1H), 7.06 (s, 1H), 7.93 (dm, J=7.3 Hz, 1H), 8.03 (dd, J=7.3, 1.3 Hz, 1H).

Reference Example 30

5-Bromo-2-ethylisoquinolin-1(2H)-one (Compound ar)

Commercially available 5-bromoisoquinoline (4.85 g, 23.3 mmol) was dissolved in dichloromethane (78 mL), and m-CPBA (9.28 g, 35.0 mmol) was added. The mixture was stirred at room temperature for 0.5 hours. The reaction mixture was diluted by adding chloroform, and washed with a saturated sodium bicarbonate aqueous solution and saturated brine. The organic layer was dried over anhydrous magnesium sulfate, and concentrated under reduced pressure. The obtained residue was dissolved in acetic anhydride (78.0 mL), and stirred for 1 hour under reflux. A 2.0 mol/L sodium hydroxide aqueous solution (156 mL) was added to the residue obtained by concentrating the reaction mixture under reduced pressure, and the mixture was stirred for 2 hours under reflux. The reaction mixture was cooled to room temperature, and neutralized with a 2.0 mol/L hydrochloric acid aqueous solution. The precipitated crystals were collected by filtration, and dried under reduced pressure to give 5-bromoisoquinolin-1(2H)-one (2.28 g, 10.1 mmol, 43%).

5-Bromoisoquinolin-1(2H)-one (501 mg, 2.23 mmol) was dissolved in DMF (10 mL), and sodium hydride (134 mg, 3.35 mmol) and ethyl iodide (0.271 mL, 3.35 mmol) were added. The mixture was stirred overnight at room temperature. After adding a saturated ammonium chloride aqueous solution, the reaction mixture was extracted with ethyl acetate. The organic layer was dried over anhydrous magnesium sulfate, and concentrated under reduced pressure. The obtained residue was purified by silica gel column chromatography (heptane/ethyl acetate=80/20) to give Compound ar (268 mg, 1.06 mmol, 47%).

ESI-MS: m/z 252, 254 [M+H]$^+$. $^1$H-NMR (CDCl$_3$) δ (ppm): 1.39 (t, J=7.2 Hz, 3H), 4.06 (q, J=7.2 Hz, 2H), 6.85 (dd, J=7.7, 1.1 Hz, 1H), 7.17 (d, J=8.1 Hz, 1H), 7.32 (dd, J=7.7, 7.7 Hz, 1H), 7.87 (dd, J=7.7, 1.1 Hz, 1H), 8.41 (d, J=8.1 Hz, 1H).

Reference Example 31

5-Bromo-2-methyl-3,4-dihydroisoquinolin-1(2H)-one (Compound as)

Commercially available 4-bromo-2,3-dihydro-1H-inden-1-one (1.02 g, 4.69 mmol) was dissolved in dichloromethane (20 mL), and methanesulfonic acid (20 mL) and sodium azide (610 mg, 308 mmol) were added. The mixture was stirred overnight at room temperature. The reaction mixture was poured into ice water, neutralized with a 3.0 mol/L sodium hydroxide aqueous solution, and extracted with chloroform. The organic layer was dried over anhydrous magnesium sulfate, and concentrated under reduced pressure. The obtained residue was purified by silica gel column chromatography (chloroform/methanol=95/5). The obtained product was dissolved in DMF (24 mL), and sodium hydride (221 mg, 5.52 mmol) and methyl 4-methylbenzenesulfonate (0.501 mL, 3.31 mmol) were added. The mixture was stirred overnight at room temperature. After adding water, the reaction mixture was extracted with ethyl acetate. The organic layer was dried over anhydrous magnesium sulfate, and concentrated under reduced pressure. The obtained residue was purified by silica gel column chromatography (heptane/ethyl acetate=70/30) to give Compound as (295 mg, 1.22 mmol, 26%).

ESI-MS: m/z 240, 242 [M+H]$^+$. $^1$H-NMR (CDCl$_3$) δ (ppm): 3.10 (t, J=6.8 Hz, 2H), 3.16 (s, 3H), 3.58 (t, J=6.8 Hz, 2H), 7.21 (dd, J=7.8, 7.8 Hz, 1H), 7.65 (d, J=7.8 Hz, 1H), 8.07 (d, J=7.8 Hz, 1H).

Reference Example 32

5-Bromo-1-methyl-3,4-dihydroisoquinolin-2(1H)-one (Compound at)

Compound at (449 mg, 1.87 mmol, 39%) was obtained from the fraction eluted by silica gel column chromatography (heptane/ethyl acetate=85/15) in Reference Example 31.

ESI-MS: m/z 240, 242 [M+H]$^+$. $^1$H-NMR (CDCl$_3$) δ (ppm): 2.65 (t, J=7.3 Hz, 2H), 3.05 (t, J=7.3 Hz, 2H), 3.35 (s, 3H), 6.94 (d, J=7.8 Hz, 1H), 7.12 (dd, J=7.8, 7.8 Hz, 1H), 7.27 (d, J=7.8 Hz, 1H).

Reference Example 33

8-Bromo-3-ethyl-3H-quinazolin-4-one (Compound au)

2-Amino-6-bromobenzoic acid (0.955 g, 4.42 mmol) obtained in Reference Example 8 was dissolved in DMF (22 mL). After adding ethylamine hydrochloride (1.08 g, 13.3 mmol), triethylamine (1.85 mL, 13.3 mmol), 1-(3-dimethylaminopropyl)-3-ethylcarbodiimide hydrochloride (1.70 g, 8.84 mmol), and 1-hydroxybenzotriazolelhydrate (1.35 g, 8.84 mmol), the mixture was stirred at room temperature for 2 days. The reaction mixture was diluted by adding ethyl acetate, and washed with water, a saturated sodium bicarbonate aqueous solution, and saturated brine. The organic layer was dried over anhydrous magnesium sulfate, and concentrated under reduced pressure. The obtained residue was purified by silica gel column chromatography (heptane/ethyl acetate=7/3) to give 2-amino-6-bromo-N-ethylbenzamide (0.744 g, 69%).

2-Amino-6-bromo-N-ethylbenzamide (0.75 g, 3.09 mmol) was dissolved in NMP (10 mL), and trimethyl orthoformate (3.4 mL) and a 4.0 mol/L hydrogen chloride/1,4-dioxane solution (3.9 mL) were added. The mixture was stirred at 110° C. for 2.5 hours. The reaction mixture was cooled to room temperature, poured into ice water, and neutralized with a saturated sodium bicarbonate aqueous solution. After extracting the mixture once with ethyl acetate, the organic layer was washed with saturated brine, dried over anhydrous magnesium sulfate, and concentrated under reduced pressure. The obtained residue was purified by silica gel column chromatography (heptane/ethyl acetate=7/3) to give Compound au (0.206 g, 26%).

ESI-MS: m/z 253, 255 [M+H]$^+$. $^1$H-NMR (CDCl$_3$) δ (ppm): 1.43 (t, J=6.8 Hz, 3H), 4.05 (q, J=6.8 Hz, 2H), 7.51 (dd, J=7.8, 7.8 Hz, 1H), 7.65 (d, J=7.8 Hz, 1H), 7.75 (d, J=7.8 Hz, 1H), 8.06 (s, 1H).

Reference Example 34

5-Bromo-2,3-dimethyl-3H-quinazolin-4-one (Compound av)

2-Amino-6-bromo-N-methylbenzamide (0.75 g, 3.20 mmol) obtained in Reference Example 8 was dissolved in NMP (11 mL), and trimethyl orthoacetate (4.0 mL) and a 4.0 mol/L hydrogen chloride/1,4-dioxane solution (4.0 mL) were added. The mixture was stirred at 110° C. for 9 hours. The reaction mixture was cooled to room temperature, poured into ice water, and neutralized with a saturated sodium bicarbonate aqueous solution. After extracting the mixture once with ethyl acetate, the organic layer was washed with saturated brine, dried over anhydrous magnesium sulfate, and concentrated under reduced pressure to give Compound av (0.830 g, quant.).

ESI-MS: m/z 253, 255 [M+H]$^+$. $^1$H-NMR (CDCl$_3$) δ (ppm): 1.87 (s, 3H), 3.72 (s, 3H), 6.68 (d, J=7.8 Hz, 1H), 7.14 (d, J=7.8 Hz, 1H), 7.25 (d, J=7.8 Hz, 1H), 7.26 (s, 1H).

Reference Example 35

3-Bromo-6-methylthieno[2,3-c]pyridin-7(6H)-one (Compound aw)

Commercially available 4-bromothiophene-2-carboxylic acid (941 mg, 4.45 mmol) was dissolved in dichloromethane (45 mL), and DMF (0.02 mL) and oxalyl chloride (0.891 mL, 9.35 mmol) were added. The mixture was stirred for 0.5 hours under reflux. After concentrating the reaction mixture, the obtained residue was dissolved in THF (20 mL), and 1-(1,3-dioxolan-2-yl)-N-methylmethanamine (2.07 mL, 17.8 mmol) was added. The mixture was stirred at room temperature for 1 hour. After adding saturated ammonium chloride, the reaction mixture was extracted with ethyl acetate. The organic layer was dried over anhydrous magnesium sulfate, and concentrated under reduced pressure. The obtained residue was purified by silica gel column chromatography (heptane/ethyl acetate=50/50) to give N-{(1,3-dioxolan-2-yl)methyl}-4-bromo-N-methylthiophene-2-carboxamido (1.28 g, 4.18 mmol, 94%).

N-{(1,3-Dioxolan-2-yl)methyl}-4-bromo-N-methylthiophene-2-carboxamido (229 mg, 0.747 mmol) was dissolved in methanesulfonic acid (3 mL), and the mixture was stirred at 120° C. for 5 days. The reaction mixture was poured into a 3.0 mol/L sodium hydroxide aqueous solution, and extracted with ethyl acetate. The organic layer was dried over anhydrous magnesium sulfate, and concentrated under reduced pressure. The obtained residue was purified by silica gel column chromatography (heptane/ethyl acetate=50/50) to give Compound aw (75.0 mg, 0.307 mmol, 41%).

ESI-MS: m/z 244, 246 [M+H]$^+$. $^1$H-NMR (CDCl$_3$) δ (ppm): 3.66 (s, 3H), 6.63 (d, J=7.0 Hz, 1H), 7.27 (d, J=7.0 Hz, 1H), 7.65 (s, 1H).

Reference Example 36

3-Bromo-1,6-dimethyl-1H-pyrrolo[2,3-c]pyridin-7(6H)-one (Compound ax)

Commercially available 1-(4-bromo-1H-pyrrol-2-yl)-2,2,2-trichloroethanone (3.02 g, 9.54 mmol) was dissolved in acetonitrile, and 1-(1,3-dioxolan-2-yl)-N-methaneamine (1.10 mL, 9.46 mmol) was added. The mixture was stirred overnight at room temperature. The reaction mixture was concentrated under reduced pressure, and the obtained residue was purified by silica gel column chromatography (heptane/ethyl acetate=70/30) to give N-{(1,3-dioxolan-2-yl)methyl}-4-bromo-N-methyl-1H-pyrrole-2-carboxamido (388 mg, 1.34 mmol, 14%).

N-{(1,3-Dioxolan-2-yl)methyl}-4-bromo-N-methyl-1H-pyrrole-2-carboxamido (375 mg, 1.29 mmol) was dissolved in methanesulfonic acid (2.5 mL), and the mixture was stirred at 45° C. for 2.5 days. The reaction mixture was poured into a 3.0 mol/L sodium hydroxide aqueous solution, and the precipitated crystals were collected by filtration, and dried overnight under reduced pressure to give 3-bromo-6-methyl-1H-pyrrolo[2,3-c]pyridin-7(6H)-one (192 mg, 0.846 mmol, 65%).

3-Bromo-6-methyl-1H-pyrrolo[2,3-c]pyridin-7(6H)-one (182 mg, 0.802 mmol) was dissolved in DMF (4 mL), and potassium carbonate (665 mg, 4.81 mmol) and methyl 4-methylbenzenesulfonate (0.363 mL, 2.40 mmol) were added. The mixture was stirred at room temperature for 2 hours. After adding a saturated ammonium chloride aqueous solution, the reaction mixture was extracted with ethyl acetate. The organic layer was dried over anhydrous magnesium sulfate, and concentrated under reduced pressure. The obtained residue was purified by silica gel column chromatography (heptane/ethyl acetate=50/50) to give Compound ax (148 mg, 0.614 mmol, 76%).

ESI-MS: m/z 241, 243 [M+H]$^+$. $^1$H-NMR (CDCl$_3$) δ (ppm): 3.57 (s, 3H), 4.15 (s, 3H), 6.36 (d, J=7.0 Hz, 1H), 6.92 (d, J=7.0 Hz, 1H), 6.98 (s, 1H).

Reference Example 37

7-Bromo-3-methylthieno[3,4-d]pyrimidin-4(3H)-one (Compound ay)

Ethanol (20 mL) and triethylamine (1.77 mL, 12.7 mmol) were successively added to a mixture of commercially available methyl 4-aminothiophene-3-carboxylate (2 g, 12.7 mmol) and formamidine acetate (6.62 g, 63.6 mmol). The mixture was stirred for 1 hour under reflux, and then at 0° C. for 1 hour. The precipitated solid was collected by filtration, washed with ethanol, and dried under reduced pressure to give a residue.

The obtained residue was dissolved in acetic acid (210 mL), and bromine (0.655 mL, 12.7 mmol) was added. The mixture was stirred at 100° C. for 2 hours. The reaction mixture was concentrated under reduced pressure, and a saturated sodium bicarbonate aqueous solution was added to the obtained residue. The insoluble matter was collected by filtration, and the filtrate was extracted with chloroform. The organic layer was washed with saturated brine, dried over anhydrous sodium sulfate, and concentrated under reduced pressure. The obtained residue was combined with the insoluble matter to give 7-bromothieno[3,4-d]pyrimidin-4 (3H)-one (1.32 g).

7-Bromothieno[3,4-d]pyrimidin-4(3H)-one (660 mg) was suspended in DMF, and potassium carbonate (1.18 g, 8.57 mmol) and methyl 4-toluenesulfonate (0.517 mL, 3.43 mmol) were added. The mixture was stirred at room temperature for 2 hours. After adding water, the reaction mixture was extracted with ethyl acetate. The organic layer was washed with water and saturated brine, dried over anhydrous sodium sulfate, and concentrated under reduced pressure. The obtained residue was purified by silica gel column chromatography (heptane/acetone) to give Compound ay (292 mg, 3 steps, 42%).

ESI-MS: m/z 245 [M+H]$^+$. $^1$H-NMR (CDCl$_3$) δ (ppm): 8.27 (s, 1H), 7.85 (s, 1H), 3.52 (s, 3H).

Reference Example 38

7-Bromo-3-methylthieno[3,2-d]pyrimidin-4(3H)-one (Compound az)

Commercially available methyl 3-aminothiophene-2-carboxylate (4 g, 25.4 mmol) was dissolved in acetic acid (40 mL), and a solution of bromine (1.31 mL, 25.4 mmol) in acetic acid (4 mL) was dropped onto the mixture. The mixture was stirred overnight at room temperature. The reaction mixture was poured into ice water, and extracted with chloroform. The organic layer was washed with water and saturated brine, dried over anhydrous sodium sulfate, and concentrated under reduced pressure. The obtained residue was purified by silica gel column chromatography (heptane/ethyl acetate=95/5) to give methyl 3-amino-4-bromothiophene-2-carboxylate (1.53 g, 26%).

Methyl 3-amino-4-bromothiophene-2-carboxylate (0.48 g, 2.03 mmol) was dissolved in methanol (10 mL), and a 1 mol/L sodium hydroxide aqueous solution (10.2 mL, 10.2 mmol) was added. The mixture was stirred overnight at room temperature. The reaction mixture was neutralized with 1 mol/L hydrochloric acid, concentrated under reduced pressure, suspended in 1,2-dimethoxyethane (20 mL), and filtered through Celite. The filtrate was concentrated under reduced pressure to give 3-amino-4-bromothiophene-2-carboxylic acid (193 mg, 43%).

3-Amino-4-bromothiophene-2-carboxylic acid (190 mg, 0.856 mmol) was dissolved in THF (4 mL), and 1,1'-carbonyldiimidazole (166 mg, 1.03 mmol) was added. The mixture was stirred overnight at room temperature. After adding a 2 mol/L methylamine/THF solution (1.29 mL, 2.58 mmol), the mixture was stirred at room temperature for 15 minutes. The reaction mixture was concentrated under reduced pressure, and the obtained residue was purified by silica gel column chromatography (heptane/ethyl acetate) to give 3-amino-4-bromo-N-methylthiophene-2-carboxamide (83.4 mg, 42%).

3-Amino-4-bromo-N-methylthiophene-2-carboxamide (80 mg, 0.340 mmol) was dissolved in NMP (1 mL), and trimethyl orthoformate (0.188 mL, 1.70 mmol) and a 4 mol/L hydrogen chloride/dioxane solution (0.043 mL, 0.170 mmol) were added. The mixture was stirred at 110° C. for 1.5 hours. The reaction mixture was cooled to room temperature, and extracted with ethyl acetate after adding a saturated sodium bicarbonate aqueous solution. The organic layer was washed with water and saturated brine, dried over anhydrous sodium sulfate, and concentrated under reduced pressure. The obtained residue was purified by silica gel column chromatography (heptane/ethyl acetate) to give Compound az (53.5 mg, 76%).

ESI-MS: m/z 245 [M+H]$^+$. $^1$H-NMR (CDCl$_3$) δ (ppm): 8.18 (s, 1H), 7.78 (s, 1H), 3.66 (s, 3H).

Reference Example 39

7-Bromo-3-(2-fluoroethyl)thieno[3,2-d]pyrimidin-4 (3H)-one (Compound ba)

3-Amino-4-bromothiophene-2-carboxylic acid (1.32 g, 5.94 mmol) obtained in Reference Example 38 was dissolved in THF (7 mL), and 1,1'-carbonyldiimidazole (1.16 g, 7.13 mmol) was added. The mixture was stirred overnight at room temperature, and triethylamine (4.14 mL, 29.7 mmol) and 2-fluoroethylamine hydrochloride (1.19 g, 11.9 mmol) were added. The mixture was stirred overnight at 70° C. The reaction mixture was cooled to room temperature, and extracted with chloroform after adding saturated brine. The organic layer was dried over anhydrous sodium sulfate, and concentrated under reduced pressure. The obtained residue was purified by silica gel column chromatography (heptane/ethyl acetate) to give 3-amino-4-bromo-N-(2-fluoroethyl) thiophene-2-carboxamide (757 mg, 48%).

3-Amino-4-bromo-N-(2-fluoroethyl)thiophene-2-carboxamide (377 mg, 1.41 mmol) was dissolved in 1-methyl-2-pyrimidone (7 mL), and trimethyl orthoformate (0.780 mL, 7.06 mmol) and a 4 mol/L hydrogen chloride/dioxane solution (0.176 mL, 0.706 mmol) were added. The mixture was stirred overnight at 110° C. The reaction mixture was cooled to room temperature, and a saturated sodium bicarbonate aqueous solution was added. The precipitated solid was collected by filtration, and dried under reduced pressure to give Compound ba (271 mg, 69%).

ESI-MS: m/z 277 [M+H]$^+$. $^1$H-NMR (CDCl$_3$) δ (ppm): 8.19 (s, 1H), 7.81 (s, 1H), 4.75 (dt, J=47.2, 4.6 Hz, 2H), 4.37 (dt, J=27.0, 4.6 Hz, 2H).

Reference Example 40

7-Bromo-3-(2-fluoroethyl)-2-methylthieno[3,2-d]pyrimidin-4(3H)-one (Compound bb)

3-Amino-4-bromo-N-(2-fluoroethyl)thiophene-2-carboxamide (377 mg, 1.41 mmol) obtained in Reference Example 39 was dissolved in 1-methyl-2-pyrimidone (7 mL), and trimethyl orthoacetate (0.898 mL, 7.06 mmol) and a 4 mol/L hydrogen chloride/dioxane solution (0.176 mL, 0.706 mmol) were added. The mixture was stirred overnight at 110° C., and further stirred overnight at 110° C. after adding trimethyl orthoacetate (0.898 mL, 7.06 mmol). The reaction mixture was cooled to room temperature, and extracted with ethyl acetate after adding water. The organic layer was washed with water and saturated brine, dried over anhydrous sodium sulfate, and concentrated under reduced pressure. The obtained residue was washed with methanol to give Compound bb (157 mg, 38%).

ESI-MS: m/z 291 [M+H]$^+$. $^1$H-NMR (CDCl$_3$) δ (ppm): 7.76 (s, 1H), 4.79 (dt, J=47.5, 4.6 Hz, 2H), 4.47 (dt, J=25.4, 4.9 Hz, 2H), 2.76 (s, 3H).

Reference Example 41

3-Bromo-5-methylthieno[3,2-c]pyridin-4(5H)-one (Compound bc)

3-Bromothieno[3,2-c]pyridin-4(5H)-one (1.09 g, 4.74 mmol) synthesized according to a known method (WO2004/100947) was suspended in DMF (24 mL), and potassium carbonate (1.96 g, 14.2 mmol) and methyl 4-toluenesulfonate (0.858 mL, 5.68 mmol) were added. The mixture was stirred overnight at room temperature. After adding a saturated sodium bicarbonate aqueous solution to the reaction mixture, the insoluble matter was filtered, and the filtrate was extracted with ethyl acetate. The organic layer was washed with water and saturated brine, dried over anhydrous sodium sulfate, and concentrated under reduced pressure. The obtained residue was washed with diethyl ether to give Compound bc (670 mg, 58%).

ESI-MS: m/z 244 [M+H]$^+$. $^1$H-NMR (CDCl$_3$) δ (ppm): 7.23 (s, 1H), 7.19 (d, J=7.8 Hz, 1H), 6.62 (d, J=7.8 Hz, 1H), 3.60 (s, 3H).

Reference Example 42

3-Bromo-5-methylfuro[3,2-c]pyridin-4(5H)-one (Compound bd)

4-Bromofuran-2-carbaldehyde (2 g, 11.4 mmol) was dissolved in pyridine (8 mL), and piperidine (0.116 mL, 1.17 mmol) was added. The mixture was stirred overnight at 100° C. After adding 1 mol/L hydrochloric acid (100 mL), the reaction mixture was stirred at room temperature for 30 minutes. The insoluble matter was collected by filtration, and dried under reduced pressure to give (E)-3-(4-bromofuran-2-yl)acrylic acid (2.32 g, 94%).

(E)-3-(4-Bromofuran-2-yl)acrylic acid (2.32 g, 10.7 mmol) was dissolved in THF (25 mL), and triethylamine (1.79 mL, 12.8 mmol) and diphenyl phosphoryl azide (2.53 mL, 11.8 mmol) were added. The mixture was stirred at room temperature for 5 hours. After adding a saturated sodium bicarbonate aqueous solution, the reaction mixture was extracted with ethyl acetate. After concentrating the organic layer under reduced pressure, methanol (10 mL) and water (10 mL) were added. The insoluble matter was collected by filtration, washed with a methanol/water=1/1 mixed solvent, and dried under reduced pressure to give (E)-3-(4-bromofuran-2-yl)acrylic acid azide (2.35 g, 91%).

(E)-3-(4-Bromofuran-2-yl)acrylic acid azide (2.34 g, 9.67 mmol) was dissolved in toluene (40 mL), and stirred for 30 minutes under reflux. The reaction mixture was cooled to room temperature, and concentrated under reduced pressure. After adding 1,2-dichlorobenzene (40 mL) and iodine (0.1 g, 0.394 mmol), the reaction mixture was stirred for 2 hours under reflux. The reaction mixture was cooled to room temperature, and diethyl ether (20 mL) was added. The insoluble matter was collected by filtration, and dried under reduced pressure to give 3-bromofuro[3,2-c]pyridin-4(5H)-one (1.63 g, 79%).

3-Bromofuro[3,2-c]pyridin-4(5H)-one (1.63 g, 7.62 mmol) was suspended in DMF (38 mL), and potassium carbonate (3.16 g, 22.9 mmol) and methyl 4-toluenesulfonate (1.38 mL, 9.14 mmol) were added. The mixture was stirred overnight at room temperature. After adding a saturated sodium bicarbonate aqueous solution to the reaction mixture, the insoluble matter was filtered, and the filtrate was extracted with ethyl acetate. The organic layer was washed with water and saturated brine, dried over anhydrous sodium sulfate, and concentrated under reduced pressure. The obtained residue was purified by silica gel column chromatography (heptane/ethyl acetate) to give Compound bd (977 mg, 56%).

ESI-MS: m/z 228 [M+H]$^+$. $^1$H-NMR (CDCl$_3$) δ (ppm): 8.43 (s, 1H), 8.14 (d, J=8.8 Hz, 1H), 7.53 (d, J=8.8 Hz, 1H), 3.98 (s, 3H).

Reference Example 43

5-Iodo-3,7-dimethyl-3H-pyrrolo[2,3-d]pyrimidin-4(7H)-one (Compound be)

3H-pyrrolo[2,3-d]pyrimidin-4(7H)-one (1.5 g, 11.1 mmol) was dissolved in DMF (30 mL), and N,O-bistrimethylsilylacetamide (12 mL, 36.4 mmol) was added. The mixture was stirred at 40° C. for 3 hours. The reaction mixture was cooled to room temperature, and N-iodosuccinimide (2.62 g, 11.7 mmol) was added. The mixture was stirred overnight at room temperature. After adding water (75 mL), the reaction mixture was stirred at room temperature for 1 hour. The insoluble matter was collected by filtration, dried under reduced pressure, and washed with a chloroform/methanol=10/1 mixed solvent to give 5-iodo-3H-pyrrolo[2,3-d]pyrimidin-4(7H)-one (2.07 g, 71%).

5-Iodo-3H-pyrrolo[2,3-d]pyrimidin-4(7H)-one (800 mg, 3.06 mmol) was dissolved in DMF (30 mL), and potassium carbonate (1.27 g, 9.19 mmol) and methyl 4-toluenesulfonate (0.971 mL, 6.44 mmol) were added. The mixture was stirred overnight at room temperature. After adding water, the reaction mixture was extracted with ethyl acetate. The organic layer was washed with water and saturated brine, dried over anhydrous sodium sulfate, and concentrated under reduced pressure. The obtained residue was washed with diethyl ether to give Compound be (521 mg, 59%).

ESI-MS: m/z 290 [M+H]$^+$. $^1$H-NMR (CDCl$_3$) δ (ppm): 8.25 (s, 1H), 7.31 (s, 1H), 3.67 (s, 3H), 3.42 (s, 3H).

Reference Example 44

5-Iodo-3-methyl-7-tosyl-3H-pyrrolo[2,3-d]pyrimidin-4 (7H)-one (Compound bf)

5-Iodo-3H-pyrrolo[2,3-d]pyrimidin-4(7H)-one (800 mg, 3.06 mmol) obtained in Reference Example 43 was dissolved in DMF (30 mL), and di-tert-butyl dicarbonate (803 mg, 3.68 mmol) and N,N-dimethyl-4-aminopyridine (37.4 mg, 0.306 mmol) were added. The mixture was stirred overnight at room temperature. Water/diethyl ether=4/1 were added to the reaction mixture until the insoluble matter precipitated, and the mixture was stirred at room temperature for 30 minutes. The insoluble matter was collected by filtration, and washed with diethyl ether to give tert-butyl 5-iodo-4-oxo-3H-pyrrolo[2,3-d]pyrimidine-7(4H)-carboxylate (650 mg, 59%).

tert-Butyl 5-iodo-4-oxo-3H-pyrrolo[2,3-d]pyrimidine-7 (4H)-carboxylate (645 mg, 1.79 mmol) was dissolved in DMF (18 mL), and potassium carbonate (494 mg, 3.57 mmol) and methyl 4-toluenesulfonate (0.296 mL, 1.97 mmol) were added. The mixture was stirred overnight at room temperature. After adding water, the reaction mixture was extracted with ethyl acetate. The organic layer was washed with water and saturated brine, dried over anhydrous sodium sulfate, and concentrated under reduced pressure. The obtained residue was purified by silica gel column chromatography (chloroform/methanol) to give tert-butyl 5-iodo-3-methyl-4-oxo-3H-pyrrolo[2,3-d]pyrimidine-7 (4H)-carboxylate (577 mg, 86%).

A 5% hydrogen chloride/methanol solution (5 mL) was added to tert-butyl 5-iodo-3-methyl-4-oxo-3H-pyrrolo[2,3-d]pyrimidine-7(4H)-carboxylate (575 mg, 1.53 mmol), and the mixture was stirred at 60° C. for 2 hours. The reaction mixture was cooled to room temperature, and a saturated sodium bicarbonate aqueous solution was added to the residue obtained by concentrating the reaction mixture under reduced pressure. The insoluble matter was collected by filtration, washed with water, and dried under reduced pressure to give 5-iodo-3-methyl-3H-pyrrolo[2,3-d]pyrimidin-4(7H)-one (320 mg, 76%).

5-Iodo-3-methyl-3H-pyrrolo[2,3-d]pyrimidin-4(7H)-one (316 mg, 1.15 mmol) was suspended in THF (11.5 mL), and 4-toluenesulfonic acid chloride (263 mg, 1.38 mmol), triethylamine (0.192 mL, 1.38 mmol), and N,N-dimethylamino-4-pyridine (7.0 mg, 0.057 mmol) were added. The mixture was stirred overnight at room temperature. After adding saturated brine, the reaction mixture was extracted with chloroform. The organic layer was dried over anhydrous sodium sulfate, and concentrated under reduced pressure. The obtained residue was recrystallized from chloroform/methanol/diethyl ether to give Compound bf (418 mg, 85%).

ESI-MS: m/z 430 [M+H]$^+$. $^1$H-NMR (DMSO-d$_6$) δ (ppm): 8.36 (s, 1H), 7.99 (d, J=7.8 Hz, 2H), 7.72 (s, 1H), 7.47 (d, J=7.8 Hz, 2H), 3.39 (s, 3H), 2.38 (s, 3H).

Reference Example 45

5-Bromo-3-methyl-3H-thieno[2,3-d]pyrimidin-4-one (Compound bg)

5-Bromothieno[2,3-d]pyrimidin-4(3H)-one (0.380 g, 1.65 mmol) synthesized according to a known method (Bioorg. Med. Chem. Lett., 2011, vol. 21, No. 18, p 5521-5527) was dissolved in DMF (16 mL). After cooling the solution to 0° C., 60% sodium hydride (79.0 mg, 1.97 mmol) was added, and the mixture was stirred at 0° C. for 15 minutes. After adding methyl iodide (0.154 mL, 2.47 mmol), and stirring the mixture at room temperature for 1 hour, a saturated ammonium chloride aqueous solution was added. The mixture was extracted twice with ethyl acetate. The organic layer was washed with saturated brine, dried over anhydrous magnesium sulfate, and concentrated under reduced pressure to give Compound bg (0.386 g, 96%).

ESI-MS: m/z 245, 247 [M+H]$^+$. $^1$H-NMR (CDCl$_3$) δ (ppm): 3.60 (s, 3H), 7.23 (s, 1H), 8.04 (s, 1H).

Example 1

(S)-2-Ethylamino-6-(4-oxo-4H-pyrido[1,2-a]pyrimidin-9-yl)-6,7,7a,8,9,10-hexahydro-5H-pyrimido[5,4-f]pyrrolo[1,2-a][1,4]diazepin-5-one (Compound 1)

Step 1

(S)-2-Methylthio-6,7,7a,8,9,10-hexahydro-5H-pyrimido [5,4-f]pyrrolo[1,2-a][1,4]diazepin-5-one (250 mg, 0.999 mmol) obtained in Reference Example 3 of WO2008/149834 was dissolved in toluene (15 mL). After adding Compound a (350 mg, 1.56 mmol) obtained in Reference Example 1, potassium carbonate (414 mg, 3.00 mmol), copper(I) iodide (192 mg, 0.999 mmol), and N,N'-dimethylethylenediamine (0.213 mL, 2.00 mmol), the mixture was stirred at 100° C. for 4.5 hours. The reaction mixture was cooled to room temperature, and filtered through Celite. The filtrate was collected, and concentrated. The obtained residue was purified by silica gel column chromatography (chloroform/methanol=40/1) to give (S)-2-methylthio-6-(4-oxo-4H-pyrido[1,2-a]pyrimidin-9-yl)-6,7,7a,8,9,10-hexahydro-5H-pyrimido[5,4-f]pyrrolo[1,2-a][1,4]diazepin-5-one (248 mg, 63%).

ESI-MS: m/z 395 [M+H]$^+$. $^1$H-NMR (CDCl$_3$) δ (ppm): 1.66 (m, 1H), 1.95 (m, 1H), 2.06 (m, 1H), 2.24 (m, 1H), 2.55 (s, 3H), 3.77-3.97 (m, 4H), 4.46 (m, 1H), 6.46 (d, J=6.3 Hz, 1H), 7.18 (dd, J=7.3, 7.3 Hz, 1H), 7.77 (dd, J=1.6, 7.3 Hz, 1H), 8.23 (d, J=6.3 Hz, 1H), 8.85 (s, 1H), 9.06 (dd, J=1.6, 7.3 Hz, 1H).

Step 2

(S)-2-Methylthio-6-(4-oxo-4H-pyrido[1,2-a]pyrimidin-9-yl)-6,7,7a,8,9,10-hexahydro-5H-pyrimido[5,4-f]pyrrolo[1,2-a][1,4]diazepin-5-one (124 mg, 0.314 mmol) obtained in step 1 was dissolved in dichloromethane (5 mL), and m-CPBA (125 mg, 0.472 mmol) was added. The mixture was stirred at room temperature for 1 hour. The reaction mixture was diluted by adding chloroform, and washed with a saturated sodium bicarbonate aqueous solution and saturated brine. The organic layer was dried over anhydrous magnesium sulfate, and concentrated under reduced pressure. The obtained residue was dissolved in THF (2 mL), and a 2.0 mol/L ethylamine/THF solution (1.57 mL, 3.14 mmol) was added. The reaction mixture was stirred at room temperature for 2 hours. The reaction mixture was concentrated under reduced pressure, and the obtained residue was purified by preparative TLC to give Compound 1 (85.3 mg, 69%).

ESI-MS: m/z 392 [M+H]$^+$. $^1$H-NMR (CDCl$_3$) δ (ppm): 1.25 (t, J=7.3 Hz, 3H), 1.65 (m, 1H), 1.92 (m, 1H), 2.03 (m, 1H), 2.20 (m, 1H), 3.43-3.53 (m, 2H), 3.76-3.93 (m, 4H), 4.36 (m, 1H), 5.25 (br s, 1H), 6.46 (d, J=6.3 Hz, 1H), 7.19 (dd, J=7.3, 7.3 Hz, 1H), 7.76 (dd, J=1.3, 7.3 Hz, 1H), 8.25 (d, J=6.3 Hz, 1H), 8.82 (s, 1H), 9.06 (dd, J=1.3, 7.3 Hz, 1H).

Example 2

(S)-2-Methylamino-6-(4-oxo-4H-pyrido[1,2-a]pyrimidin-9-yl)-6,7,7a,8,9,10-hexahydro-5H-pyrimido [5,4-f]pyrrolo[1,2-a][1,4]diazepin-5-one (Compound 2)

(S)-2-Methylthio-6-(4-oxo-4H-pyrido[1,2-a]pyrimidin-9-yl)-6,7,7a,8,9,10-hexahydro-5H-pyrimido[5,4-f]pyrrolo[1,2-a][1,4]diazepin-5-one (124 mg, 0.314 mmol) obtained in step 1 of Example 1 was dissolved in dichloromethane (5 mL), and m-CPBA was added (125 mg, 0.472 mmol). The mixture was stirred at room temperature for 1 hour. The reaction mixture was diluted by adding chloroform, and washed with a saturated sodium bicarbonate aqueous solution and saturated brine. The organic layer was dried over anhydrous magnesium sulfate, and concentrated under reduced pressure. The obtained residue was dissolved in THF (2 mL), and a 2.0 mol/L methylamine/THF solution (1.57 mL, 3.14 mmol) was added. The mixture was stirred at room temperature for 2 hour. The reaction mixture was concentrated under reduced pressure, and the obtained residue was purified by preparative TLC to give Compound 2 (96.8 mg, 82%).

ESI-MS: m/z 378 [M+H]$^+$. $^1$H-NMR (CDCl$_3$) δ (ppm): 1.66 (m, 1H), 1.94 (m, 1H), 2.03 (m, 1H), 2.20 (m, 1H), 3.01 (d, J=5.3 Hz, 3H), 3.77-3.92 (m, 4H), 4.36 (m, 1H), 5.33 (br s, 1H), 6.46 (d, J=6.3 Hz, 1H), 7.18 (dd, J=7.3, 7.3 Hz, 1H), 7.76 (dd, J=1.3, 7.3 Hz, 1H), 8.25 (d, J=6.3 Hz, 1H), 8.81 (s, 1H), 9.05 (dd, J=1.3, 7.3 Hz, 1H).

Example 3

(S)-2-Ethylamino-6-(2-methyl-4-oxo-4H-pyrido[1,2-a]pyrimidin-9-yl)-6,7,7a,8,9,10-hexahydro-5H-pyrimido[5,4-f]pyrrolo[1,2-a][1,4]diazepin-5-one (Compound 3)

Step 1
(S)-6-(2-Methyl-4-oxo-4H-pyrido[1,2-a]pyrimidin-9-yl)-2-methylthio-6,7,7a,8,9,10-hexahydro-5H-pyrimido[5,4-f] pyrrolo[1,2-a][1,4]diazepin-5-one (348 mg, 85%) was obtained in the same manner as in step 1 of Example 1 using (S)-2-methylthio-6,7,7a,8,9,10-hexahydro-5H-pyrimido[5, 4-f]pyrrolo[1,2-a][1,4]diazepin-5-one (250 mg, 0.999 mmol) obtained in Reference Example 3 of WO2008/149834, and Compound b (358 mg, 1.50 mmol) obtained in Reference Example 2, instead of Compound a.

ESI-MS: m/z 409 [M+H]$^+$. $^1$H-NMR (CDCl$_3$) δ (ppm): 1.68 (m, 1H), 1.94 (m, 1H), 2.08 (m, 1H), 2.25 (m, 1H), 2.38 (s, 3H), 2.54 (s, 3H), 3.65-3.95 (m, 4H), 4.61 (m, 1H), 6.32 (s, 1H), 7.11 (dd, J=7.3, 7.3 Hz, 1H), 7.74 (dd, J=1.3, 7.3 Hz, 1H), 8.84 (s, 1H), 8.98 (dd, J=1.3, 7.3 Hz, 1H).

Step 2
Compound 3 (122 mg, 71%) was obtained in the same manner as in step 2 of Example 1, using (S)-6-(2-methyl-4-oxo-4H-pyrido[1,2-a]pyrimidin-9-yl)-2-methylthio-6,7, 7a,8,9,10-hexahydro-5H-pyrimido[5,4-f]pyrrolo[1,2-a][1,4] diazepin-5-one (174 mg, 0.426 mmol) obtained in step 1.

ESI-MS: m/z 406 [M+H]$^+$. $^1$H-NMR (CDCl$_3$) δ (ppm): 1.25 (t, J=7.3 Hz, 3H), 1.67 (m, 1H), 1.92 (m, 1H), 2.04 (m, 1H), 2.22 (m, 1H), 2.40 (s, 3H), 3.43-3.53 (m, 2H), 3.76-3.94 (m, 4H), 4.51 (m, 1H), 5.33 (br s, 1H), 6.34 (s, 1H), 7.12 (dd, J=7.3, 7.3 Hz, 1H), 7.74 (dd, J=1.6, 7.3 Hz, 1H), 8.83 (s, 1H), 8.99 (dd, J=1.6, 7.3 Hz, 1H).

Example 4

(S)-6-(2-Methyl-4-oxo-4H-pyrido[1,2-a]pyrimidin-9-yl)-2-methylamino-6,7,7a,8,9,10-hexahydro-5H-pyrimido[5,4-f]pyrrolo[1,2-a][1,4]diazepin-5-one (Compound 4)

Compound 4 (107 mg, 64%) was obtained in the same manner as in Example 2, using (S)-6-(2-methyl-4-oxo-4H-pyrido[1,2-a]pyrimidin-9-yl)-2-methylthio-6,7,7a,8,9,10-hexahydro-5H-pyrimido[5,4-f]pyrrolo[1,2-a][1,4]diazepin-5-one (174 mg, 0.426 mmol) obtained in step 1 of Example 3.

ESI-MS: m/z 392 [M+H]$^+$. $^1$H-NMR (CDCl$_3$) δ (ppm): 1.67 (m, 1H), 1.92 (m, 1H), 2.05 (m, 1H), 2.23 (m, 1H), 2.41 (s, 3H), 3.02 (d, J=5.0 Hz, 3H), 3.75-3.96 (m, 4H), 4.51 (m, 1H), 5.32 (br s, 1H), 6.34 (s, 1H), 7.12 (dd, J=7.3, 7.3 Hz, 1H), 7.74 (dd, J=1.6, 7.3 Hz, 1H), 8.84 (s, 1H), 8.99 (dd, J=1.6, 7.3 Hz, 1H).

Example 5

(S)-6-(2-Ethyl-4-oxo-4H-pyrido[1,2-a]pyrimidin-9-yl)-2-ethylamino-6,7,7a,8,9,10-hexahydro-5H-pyrimido[5,4-f]pyrrolo[1,2-a][1,4]diazepin-5-one (Compound 5)

Step 1
(S)-6-(2-Ethyl-4-oxo-4H-pyrido[1,2-a]pyrimidin-9-yl)-2-methylthio-6,7,7a,8,9,10-hexahydro-5H-pyrimido[5,4-f] pyrrolo[1,2-a][1,4]diazepin-5-one (174 mg, 41%) was obtained in the same manner as in step 1 of Example 1 using (S)-2-methylthio-6,7,7a,8,9,10-hexahydro-5H-pyrimido[5, 4-f]pyrrolo[1,2-a][1,4]diazepin-5-one (250 mg, 0.999 mmol) obtained in Reference Example 3 of WO2008/149834, and Compound c (505 mg, 2.00 mmol) obtained in Reference Example 3, instead of Compound a.

ESI-MS: m/z 423 [M+H]$^+$. $^1$H-NMR (CDCl$_3$) δ (ppm): 1.24 (t, J=7.3 Hz, 3H), 1.67 (m, 1H), 1.93 (m, 1H), 2.07 (m, 1H), 2.23 (m, 1H), 2.55 (s, 3H), 2.65 (q, J=7.3 Hz, 2H), 3.68-3.97 (m, 4H), 4.57 (m, 1H), 6.35 (s, 1H), 7.10 (dd, J=7.3, 7.3 Hz, 1H), 7.73 (dd, J=1.3, 7.3 Hz, 1H), 8.84 (s, 1H), 8.99 (dd, J=1.3, 7.3 Hz, 1H).

Step 2
Compound 5 (68.5 mg, 79%) was obtained in the same manner as in step 2 of Example 1, using (S)-6-(2-ethyl-4-oxo-4H-pyrido[1,2-a]pyrimidin-9-yl)-2-methylthio-6,7,7a, 8,9,10-hexahydro-5H-pyrimido[5,4-f]pyrrolo[1,2-a][1,4]diazepin-5-one (87.0 mg, 0.206 mmol) obtained in step 1.

ESI-MS: m/z 420 [M+H]$^+$. $^1$H-NMR (CDCl$_3$) δ (ppm): 1.25 (t, J=7.3 Hz, 3H), 1.26 (t, J=7.3 Hz, 3H), 1.66 (m, 1H), 1.91 (m, 1H), 2.04 (m, 1H), 2.20 (m, 1H), 2.67 (q, J=7.3 Hz, 2H), 3.44-3.54 (m, 2H), 3.65-3.93 (m, 4H), 4.48 (m, 1H), 5.22 (br s, 1H), 6.36 (s, 1H), 7.11 (dd, J=7.3, 7.3 Hz, 1H), 7.72 (dd, J=1.6, 7.3 Hz, 1H), 8.83 (s, 1H), 8.99 (dd, J=1.6, 7.3 Hz, 1H).

Example 6

(S)-6-(2-Ethyl-4-oxo-4H-pyrido[1,2-a]pyrimidin-9-yl)-2-methylamino-6,7,7a,8,9,10-hexahydro-5H-pyrimido[5,4-f]pyrrolo[1,2-a][1,4]diazepin-5-one (Compound 6)

Compound 6 (70.4 mg, 84%) was obtained in the same manner as in Example 2, using (S)-6-(2-ethyl-4-oxo-4H-pyrido[1,2-a]pyrimidin-9-yl)-2-methylthio-6,7,7a,8,9,10-hexahydro-5H-pyrimido[5,4-f]pyrrolo[1,2-a][1,4]diazepin-5-one (87.0 mg, 0.206 mmol) obtained in step 1 of Example 5.

ESI-MS: m/z 406 [M+H]$^+$. $^1$H-NMR (CDCl$_3$) δ (ppm): 1.26 (t, J=7.3 Hz, 3H), 1.65 (m, 1H), 1.90 (m, 1H), 2.05 (m, 1H), 2.21 (m, 1H), 2.67 (q, J=7.3 Hz, 2H), 3.02 (d, J=5.0 Hz, 3H), 3.65-3.96 (m, 4H), 4.51 (m, 1H), 5.22 (br s, 1H), 6.36 (s, 1H), 7.11 (dd, J=7.3, 7.3 Hz, 1H), 7.72 (dd, J=1.6, 7.3 Hz, 1H), 8.84 (s, 1H), 9.00 (dd, J=1.6, 7.3 Hz, 1H).

Example 7

(S)-6-(2,3-Dimethyl-4-oxo-4H-pyrido[1,2-a]pyrimidin-9-yl)-2-ethylamino-6,7,7a,8,9,10-hexahydro-5H-pyrimido[5,4-f]pyrrolo[1,2-a][1,4]diazepin-5-one (Compound 7)

Step 1

(S)-2-Methylthio-6,7,7a,8,9,10-hexahydro-5H-pyrimido[5,4-f]pyrrolo[1,2-a][1,4]diazepin-5-one (16.0 g, 63.9 mmol) obtained in Reference Example 3 of WO2008/149834 was suspended in toluene (160 mL). After adding Compound d (24.3 g, 95.9 mmol) obtained in Reference Example 4, potassium carbonate (26.5 mg, 192 mmol), copper(I) iodide (12.2 g, 63.9 mmol), and N,N'-dimethylethylenediamine (13.6 mL, 128 mmol), the mixture was stirred at 100° C. for 1.5 hours. Then, copper(I) iodide (12.2 g, 63.9 mmol), and N,N'-dimethylethylenediamine (13.6 mL, 128 mmol) were added, and the mixture was stirred at 100° C. for 2.5 hours. After cooling the reaction mixture to room temperature, 10% ammonia water was added, and the reaction mixture was extracted with chloroform. The organic layer was washed twice with 10% ammonia water, and then with saturated brine, dried over anhydrous magnesium sulfate, and concentrated under reduced pressure. The obtained residue was reslurried in methanol to give (S)-6-(2,3-dimethyl-4-oxo-4H-pyrido[1,2-a]pyrimidin-9-yl)-2-methylthio-6,7,7a,8,9,10-hexahydro-5H-pyrimido[5,4-f]pyrrolo[1,2-a][1,4]diazepin-5-one (16.2 g, 60%).

ESI-MS: m/z 423 [M+H]$^+$. $^1$H-NMR (CDCl$_3$) δ: 1.69 (m, 1H), 1.95 (m, 1H), 2.10 (m, 1H), 2.20 (s, 3H), 2.27 (m, 1H), 2.43 (s, 3H), 2.57 (s, 3H), 3.69-3.99 (m, 4H), 4.68 (m, 1H), 7.08 (dd, J=7.1, 7.3 Hz, 1H), 7.64 (dd, J=1.5, 7.3 Hz, 1H), 8.89 (s, 1H), 8.96 (dd, J=1.5, 7.3 Hz, 1H).

Step 2

(S)-6-(2,3-Dimethyl-4-oxo-4H-pyrido[1,2-a]pyrimidin-9-yl)-2-methylthio-6,7,7a,8,9,10-hexahydro-5H-pyrimido[5,4-f]pyrrolo[1,2-a][1,4]diazepin-5-one (2.00 g, 4.73 mmol) obtained in step 1 was dissolved in dichloromethane (24 mL), and m-CPBA (1.51 g, 5.68 mmol) was added. The mixture was stirred at room temperature for 1 hour. The reaction mixture was diluted by adding chloroform, and washed with a saturated sodium bicarbonate aqueous solution and saturated brine. The organic layer was dried over anhydrous magnesium sulfate, and concentrated under reduced pressure. The obtained residue was dissolved in THF (24 mL), and a 2.0 mol/L ethylamine/THF solution (4.73 mL, 9.46 mmol) was added. The mixture was stirred at room temperature for 3 hours. The reaction mixture was concentrated under reduced pressure, and the obtained residue was reslurried in an ethanol-water mixed solvent to give Compound 7 (1.18 g, 60%).

ESI-MS: m/z 420 [M+H]$^+$. $^1$H-NMR (CDCl$_3$) δ (ppm): 1.25 (t, J=7.3 Hz, 3H), 1.67 (m, 1H), 1.92 (m, 1H), 2.04 (m, 1H), 2.20 (m, 1H), 2.24 (s, 3H), 2.43 (s, 3H), 3.43-3.53 (m, 2H), 3.81 (m, 1H), 4.47-4.61 (m, 4H), 5.17 (br s, 1H), 7.07 (dd, J=7.3, 7.3 Hz, 1H), 7.63 (dd, J=1.6, 7.3 Hz, 1H), 8.83 (s, 1H), 8.95 (dd, J=1.6, 7.3 Hz, 1H).

Example 8

(S)-6-(2,3-Dimethyl-4-oxo-4H-pyrido[1,2-a]pyrimidin-9-yl)-2-methylamino-6,7,7a,8,9,10-hexahydro-5H-pyrimido[5,4-f]pyrrolo[1,2-a][1,4]diazepin-5-one (Compound 8)

(S)-6-(2,3-Dimethyl-4-oxo-4H-pyrido[1,2-a]pyrimidin-9-yl)-2-methylthio-6,7,7a,8,9,10-hexahydro-5H-pyrimido[5,4-f]pyrrolo[1,2-a][1,4]diazepin-5-one (16.0 g, 37.8 mmol) obtained in step 1 of Example 7 was dissolved in dichloromethane (189 mL), and m-CPBA (12.0 g, 45.3 mmol) was added. The mixture was stirred at room temperature for 0.5 hours. The reaction mixture was diluted by adding chloroform, and washed with a sodium thiosulfate aqueous solution, a saturated sodium bicarbonate aqueous solution, and saturated brine. The organic layer was dried over anhydrous magnesium sulfate, and concentrated under reduced pressure. The obtained residue was suspended in THF (160 mL), and a 2.0 mol/L methylamine/THF solution (37.8 mL, 75.6 mmol) was added. The mixture was stirred at 60° C. for 2.5 hours. After concentrating the reaction mixture under reduced pressure, the obtained residue was dissolved in chloroform, dried over anhydrous magnesium sulfate, and concentrated under reduced pressure. The obtained residue was reslurried in ethanol, and the resulting solid was further reslurried in ethyl acetate to give Compound 8 (12.2 g, 80%).

ESI-MS: m/z 406 [M+H]$^+$. $^1$H-NMR (CDCl$_3$) δ: 1.68 (m, 1H), 1.91 (m, 1H), 2.06 (m, 1H), 2.23 (m, 1H), 2.24 (s, 3H), 2.43 (s, 3H), 3.03 (d, J=5.1 Hz, 3H), 3.63-3.95 (m, 4H), 4.54 (m, 1H), 5.13 (br s, 1H), 7.07 (dd, J=7.0, 7.3 Hz, 1H), 7.63 (dd, J=1.3, 7.0 Hz, 1H), 8.84 (s, 1H), 8.95 (dd, J=1.3, 7.3 Hz, 1H).

Example 9

(S)-2-Ethylamino-6-(3-methyl-4-oxo-3,4-dihydroquinazolin-8-yl)-6,7,7a,8,9,10-hexahydro-5H-pyrimido[5,4-f]pyrrolo[1,2-a][1,4]diazepin-5-one (Compound 9)

Step 1

(S)-6-(3-Methyl-4-oxo-3,4-dihydroquinazolin-8-yl)-2-methylthio-6,7,7a,8,9,10-hexahydro-5H-pyrimido[5,4-f]pyrrolo[1,2-a][1,4]diazepin-5-one (16.9 g, 74%) was obtained in the same manner as in step 1 of Example 7 using (S)-2-methylthio-6,7,7a,8,9,10-hexahydro-5H-pyrimido[5,4-f]pyrrolo[1,2-a][1,4]diazepin-5-one (14.1 g, 56.1 mmol) obtained in Reference Example 3 of WO2008/149834, and Compound e (20.1 g, 84.2 mmol) obtained in Reference Example 5, instead of Compound d.

ESI-MS: m/z 409 [M+H]$^+$. $^1$H-NMR (CDCl$_3$) δ: 1.66 (m, 1H), 1.93 (m, 1H), 2.06 (m, 1H), 2.17 (m, 1H), 2.56 (s, 3H), 3.57 (s, 3H), 3.69-3.99 (m, 4H), 4.37 (m, 1H), 7.54 (dd,

J=7.7, 7.9 Hz, 1H), 7.67 (dd, J=1.5, 7.7 Hz, 1H), 8.01 (s, 1H), 8.31 (dd, J=1.5, 7.9 Hz, 1H), 8.89 (s, 1H).

Step 2

(S)-6-(3-Methyl-4-oxo-3,4-dihydroquinazolin-8-yl)-2-methylthio-6,7,7a,8,9,10-hexahydro-5H-pyrimido[5,4-f]pyrrolo[1,2-a][1,4]diazepin-5-one (2.50 g, 6.12 mmol) obtained in step 1 was dissolved in dichloromethane (31 mL), and m-CPBA (1.95 g, 7.34 mmol) was added. The mixture was stirred at room temperature for 0.5 hours. The reaction mixture was diluted by adding chloroform, and washed with a sodium thiosulfate aqueous solution and a saturated sodium bicarbonate aqueous solution. The organic layer was dried over anhydrous magnesium sulfate, and concentrated under reduced pressure. The obtained residue was suspended in THF (31 mL), and a 2.0 mol/L ethylamine/THF solution (6.12 mL, 12.2 mmol) was added. The mixture was stirred at room temperature for 3.5 hours. After concentrating the reaction mixture under reduced pressure, the obtained residue was reslurried in ethanol to give Compound 9 (2.16 g, 87%).

ESI-MS: m/z 406 [M+H]$^+$. $^1$H-NMR (CDCl$_3$) δ (ppm): 1.24 (t, J=7.6 Hz, 3H), 1.62 (m, 1H), 1.88 (m, 1H), 2.00 (m, 1H), 2.12 (m, 1H), 3.42-3.52 (m, 2H), 3.56 (s, 3H), 3.77-3.98 (m, 4H), 4.29 (m, 1H), 5.20 (br s, 1H), 7.52 (dd, J=7.6, 7.9 Hz, 1H), 7.67 (dd, J=1.6, 7.6 Hz, 1H), 8.01 (s, 1H), 8.28 (dd, J=1.6, 7.9 Hz, 1H), 8.83 (s, 1H).

Example 10

(S)-6-(3-Methyl-4-oxo-3,4-dihydroquinazolin-8-yl)-2-methylamino-6,7,7a,8,9,10-hexahydro-5H-pyrimido[5,4-f]pyrrolo[1,2-a][1,4]diazepin-5-one (Compound 10)

(S)-6-(3-Methyl-4-oxo-3,4-dihydroquinazolin-8-yl)-2-methylthio-6,7,7a,8,9,10-hexahydro-5H-pyrimido[5,4-f]pyrrolo[1,2-a][1,4]diazepin-5-one (17.2 g, 42.0 mmol) obtained in step 1 of Example 9 was dissolved in dichloromethane (210 mL), and m-CPBA (13.4 g, 50.4 mmol) was added. The mixture was stirred at room temperature for 0.5 hours. The reaction mixture was diluted by adding chloroform, and washed with sodium thiosulfate aqueous solution and saturated sodium bicarbonate aqueous solution. The organic layer was dried over anhydrous magnesium sulfate, and concentrated under reduced pressure. The obtained residue was suspended in THF (170 mL), and a 2.0 mol/L methylamine/THF solution (42.0 mL, 84.0 mmol) was added. The mixture was stirred at room temperature for 3.5 hours. After concentrating the reaction mixture under reduced pressure, the obtained residue was reslurried in ethanol to give Compound 10 (13.9 g, 85%).

ESI-MS: m/z 392 [M+H]$^+$. $^1$H-NMR (CDCl$_3$) δ: 1.62 (m, 1H), 1.88 (m, 1H), 2.02 (m, 1H), 2.14 (m, 1H), 3.02 (d, J=5.1 Hz, 3H), 3.57 (s, 3H), 3.65-3.97 (m, 4H), 4.29 (m, 1H), 5.08 (br s, 1H), 7.52 (dd, J=7.7, 8.1 Hz, 1H), 7.67 (dd, J=1.5, 7.7 Hz, 1H), 8.01 (s, 1H), 8.29 (dd, J=1.5, 8.1 Hz, 1H), 8.84 (s, 1H).

Example 11

(S)-2-Ethylamino-6-(2,3-dimethyl-4-oxo-3,4-dihydroquinazolin-8-yl)-6,7,7a,8,9,10-hexahydro-5H-pyrimido[5,4-f]pyrrolo[1,2-a][1,4]diazepin-5-one (Compound 11)

Step 1

(S)-6-(2,3-Dimethyl-4-oxo-3,4-dihydroquinazolin-8-yl)-2-methylthio-6,7,7a,8,9,10-hexahydro-5H-pyrimido[5,4-f]pyrrolo[1,2-a][1,4]diazepin-5-one (256 mg, 61%) was obtained in the same manner as in step 1 of Example 1 using (S)-2-methylthio-6,7,7a,8,9,10-hexahydro-5H-pyrimido[5,4-f]pyrrolo[1,2-a][1,4]diazepin-5-one (250 mg, 0.999 mmol) obtained in Reference Example 3 of WO2008/149834, and Compound f (379 mg, 1.50 mmol) obtained in Reference Example 6, instead of Compound a.

ESI-MS: m/z 423 [M+H]$^+$. $^1$H-NMR (CDCl$_3$) δ (ppm): 1.63 (m, 1H), 1.92 (m, 1H), 2.05 (m, 1H), 2.18 (m, 1H), 2.51 (s, 3H), 2.54 (s, 3H), 3.56 (s, 3H), 3.77-3.92 (m, 4H), 4.39 (m, 1H), 7.42 (dd, J=7.6, 7.9 Hz, 1H), 7.62 (dd, J=1.3, 7.6 Hz, 1H), 8.21 (dd, J=1.3, 7.9 Hz, 1H), 8.83 (s, 1H).

Step 2

Compound 11 (79.5 mg, 63%) was obtained in the same manner as in step 2 of Example 1, using (S)-6-(2,3-dimethyl-4-oxo-3,4-dihydroquinazolin-8-yl)-2-methylthio-6,7,7a,8,9,10-hexahydro-5H-pyrimido[5,4-f]pyrrolo[1,2-a][1,4]diazepin-5-one (128 mg, 0.302 mmol) obtained in step 1.

ESI-MS: m/z 420 [M+H]$^+$. $^1$H-NMR (CDCl$_3$) δ (ppm): 1.25 (t, J=7.3 Hz, 3H), 1.64 (m, 1H), 1.90 (m, 1H), 2.02 (m, 1H), 2.15 (m, 1H), 2.56 (s, 3H), 3.43-3.53 (m, 2H), 3.59 (s, 3H), 3.75-3.96 (m, 4H), 4.41 (m, 1H), 5.30 (br s, 1H), 7.44 (dd, J=7.6, 7.9 Hz, 1H), 7.64 (dd, J=1.3, 7.6 Hz, 1H), 8.22 (dd, J=1.3, 7.9 Hz, 1H), 8.83 (s, 1H).

Example 12

(S)-6-(2,3-Dimethyl-4-oxo-3,4-dihydroquinazolin-8-yl)-2-methylamino-6,7,7a,8,9,10-hexahydro-5H-pyrimido[5,4-f]pyrrolo[1,2-a][1,4]diazepin-5-one (Compound 12)

Compound 12 (82.5 mg, 68%) was obtained in the same manner as in Example 2, using (S)-6-(2,3-dimethyl-4-oxo-3,4-dihydroquinazolin-8-yl)-2-methylthio-6,7,7a,8,9,10-hexahydro-5H-pyrimido[5,4-f]pyrrolo[1,2-a][1,4]diazepin-5-one (128 mg, 0.302 mmol) obtained in step 1 of Example 11.

ESI-MS: m/z 406 [M+H]$^+$. $^1$H-NMR (CDCl$_3$) δ (ppm): 1.64 (m, 1H), 1.91 (m, 1H), 2.03 (m, 1H), 2.15 (m, 1H), 2.56 (s, 3H), 3.02 (d, J=5.0 Hz, 3H), 3.59 (s, 3H), 3.73-3.95 (m, 4H), 4.40 (m, 1H), 5.17 (br s, 1H), 7.44 (dd, J=7.9, 7.9 Hz, 1H), 7.64 (dd, J=1.6, 7.9 Hz, 1H), 8.22 (dd, J=1.6, 7.9 Hz, 1H), 8.85 (s, 1H).

Example 13

(S)-6-(3-Ethyl-4-oxo-3,4-dihydroquinazolin-8-yl)-2-ethylamino-6,7,7a,8,9,10-hexahydro-5H-pyrimido[5,4-f]pyrrolo[1,2-a][1,4]diazepin-5-one (Compound 13)

Step 1

(S)-6-(3-Ethyl-4-oxo-3,4-dihydroquinazolin-8-yl)-2-methylthio-6,7,7a,8,9,10-hexahydro-5H-pyrimido[5,4-f]pyrrolo[1,2-a][1,4]diazepin-5-one (186 mg, 44%) was obtained in the same manner as in step 1 of Example 1 using (S)-2-methylthio-6,7,7a,8,9,10-hexahydro-5H-pyrimido[5,4-f]pyrrolo[1,2-a][1,4]diazepin-5-one (250 mg, 0.999 mmol) obtained in Reference Example 3 of WO2008/149834, and Compound g (379 mg, 1.50 mmol) obtained in Reference Example 7, instead of Compound a.

ESI-MS: m/z 423 [M+H]$^+$. $^1$H-NMR (CDCl$_3$) δ (ppm): 1.40 (t, J=7.3 Hz, 3H), 1.64 (m, 1H), 1.92 (m, 1H), 2.04 (m, 1H), 2.15 (m, 1H), 2.54 (s, 3H), 3.73-4.15 (m, 6H), 4.38 (m, 1H), 7.51 (dd, J=7.6, 7.9 Hz, 1H), 7.66 (dd, J=1.6, 7.6 Hz, 1H), 8.01 (s, 1H), 8.30 (dd, J=1.6, 7.9 Hz, 1H), 8.87 (s, 1H).

Step 2

Compound 13 (87.9 mg, 95%) was obtained in the same manner as in step 2 of Example 1, using (S)-6-(3-ethyl-4-oxo-3,4-dihydroquinazolin-8-yl)-2-methylthio-6,7,7a,8,9,10-hexahydro-5H-pyrimido[5,4-f]pyrrolo[1,2-a][1,4]diazepin-5-one (93.0 mg, 0.220 mmol) obtained in step 1.

ESI-MS: m/z 420 [M+H]$^+$. $^1$H-NMR (CDCl$_3$) δ (ppm): 1.24 (t, J=7.3 Hz, 3H), 1.41 (t, J=7.3 Hz, 3H), 1.63 (m, 1H), 1.88 (m, 1H), 2.02 (m, 1H), 2.14 (m, 1H), 3.43-3.52 (m, 2H), 3.77-4.08 (m, 6H), 4.28 (m, 1H), 5.20 (br s, 1H), 7.52 (dd, J=7.6, 7.9 Hz, 1H), 7.66 (dd, J=1.6, 7.6 Hz, 1H), 8.02 (s, 1H), 8.29 (dd, J=1.6, 7.9 Hz, 1H), 8.83 (s, 1H).

Example 14

(S)-6-(3-Ethyl-4-oxo-3,4-dihydroquinazolin-8-yl)-2-methylamino-6,7,7a,8,9,10-hexahydro-5H-pyrimido[5,4-f]pyrrolo[1,2-a][1,4]diazepin-5-one (Compound 14)

Compound 14 (81.9 mg, 92%) was obtained in the same manner as in Example 2, using (S)-6-(3-ethyl-4-oxo-3,4-dihydroquinazolin-8-yl)-2-methylthio-6,7,7a,8,9,10-hexahydro-5H-pyrimido[5,4-f]pyrrolo[1,2-a][1,4]diazepin-5-one (93.0 mg, 0.220 mmol) obtained in step 1 of Example 13.

ESI-MS: m/z 406 [M+H]$^+$. $^1$H-NMR (CDCl$_3$) δ (ppm): 1.41 (t, J=7.3 Hz, 3H), 1.63 (m, 1H), 1.89 (m, 1H), 2.02 (m, 1H), 2.14 (m, 1H), 3.02 (d, J=5.0 Hz, 3H), 3.78-4.11 (m, 6H), 4.29 (m, 1H), 5.21 (br s, 1H), 7.52 (dd, J=7.6, 7.9 Hz, 1H), 7.67 (dd, J=1.6, 7.6 Hz, 1H), 8.02 (s, 1H), 8.29 (dd, J=1.6, 7.9 Hz, 1H), 8.84 (s, 1H).

Example 15

(S)-2-Ethylamino-6-(3-methyl-4-oxo-3,4-dihydroquinazolin-5-yl)-6,7,7a,8,9,10-hexahydro-5H-pyrimido[5,4-f]pyrrolo[1,2-a][1,4]diazepin-5-one (Compound 15)

Step 1

(S)-6-(3-Methyl-4-oxo-3,4-dihydroquinazolin-5-yl)-2-methylthio-6,7,7a,8,9,10-hexahydro-5H-pyrimido[5,4-f]pyrrolo[1,2-a][1,4]diazepin-5-one (244 mg, 44%) was obtained in the same manner as in step 1 of Example 1 using (S)-2-methylthio-6,7,7a,8,9,10-hexahydro-5H-pyrimido[5,4-f]pyrrolo[1,2-a][1,4]diazepin-5-one (342 mg, 1.37 mmol) obtained in Reference Example 3 of WO2008/149834, and Compound h (490 mg, 2.05 mmol) obtained in Reference Example 8, instead of Compound a.

ESI-MS: m/z 409 [M+H]$^+$. $^1$H-NMR (CDCl$_3$) δ (ppm): 1.64 (m, 1H), 1.93 (m, 1H), 2.03 (m, 1H), 2.17 (m, 1H), 2.54 (s, 3H), 3.48 (s, 1.5H), 3.50 (s, 1.5H), 3.78-3.98 (m, 4H), 4.12 (m, 1H), 7.21 (dd, J=2.6, 6.3 Hz, 0.5H), 7.22 (dd, J=2.6, 6.3 Hz, 0.5H), 7.30 (dd, J=1.3, 7.3 Hz, 0.5H), 7.66-7.79 (m, 1.5H), 8.02 (s, 0.5H), 8.03 (s, 0.5H), 8.87 (s, 0.5H), 8.90 (s, 0.5H).

Step 2

Compound 15 (79.8 mg, 66%) was obtained in the same manner as in step 2 of Example 1, using (S)-6-(3-methyl-4-oxo-3,4-dihydroquinazolin-5-yl)-2-methylthio-6,7,7a,8,9,10-hexahydro-5H-pyrimido[5,4-f]pyrrolo[1,2-a][1,4]diazepin-5-one (122 mg, 0.298 mmol) obtained in step 1.

ESI-MS: m/z 406 [M+H]$^+$. $^1$H-NMR (CDCl$_3$) δ (ppm): 1.24 (t, J=7.3 Hz, 3H), 1.63 (m, 1H), 1.90 (m, 1H), 2.00 (m, 1H), 2.14 (m, 1H), 3.42-3.54 (m, 2H), 3.50 (s, 1.5H), 3.52 (s, 1.5H), 3.73-3.97 (m, 4H), 4.11 (m, 1H), 5.21 (br s, 1H), 7.22 (dd, J=1.3, 7.3 Hz, 0.5H), 7.30 (dd, J=1.3, 7.3 Hz, 0.5H), 7.65-7.80 (m, 2H), 8.03 (s, 1H), 8.84 (s, 0.5H), 8.86 (s, 0.5H).

Example 16

(S)-6-(3-Methyl-4-oxo-3,4-dihydroquinazolin-5-yl)-2-methylamino-6,7,7a,8,9,10-hexahydro-5H-pyrimido[5,4-f]pyrrolo[1,2-a][1,4]diazepin-5-one (Compound 16)

Compound 16 (78.6 mg, 67%) was obtained in the same manner as in Example 2, using (S)-6-(3-methyl-4-oxo-3,4-dihydroquinazolin-5-yl)-2-methylthio-6,7,7a,8,9,10-hexahydro-5H-pyrimido[5,4-f]pyrrolo[1,2-a][1,4]diazepin-5-one (122 mg, 0.298 mmol) obtained in step 1 of Example 15.

ESI-MS: m/z 392 [M+H]$^+$. $^1$H-NMR (CDCl$_3$) δ (ppm): 1.62 (m, 1H), 1.89 (m, 1H), 2.00 (m, 1H), 2.13 (m, 1H), 3.00 (d, J=5.3 Hz, 3H), 3.49 (s, 1.5H), 3.51 (s, 1.5H), 3.75-4.14 (m, 4.5H), 4.56 (m, 0.5H), 5.18 (br s, 1H), 7.21 (dd, J=1.3, 7.6 Hz, 0.5H), 7.30 (dd, J=1.3, 7.6 Hz, 0.5H), 7.64-7.79 (m, 2H), 8.02 (s, 1H), 8.83 (s, 0.5H), 8.86 (s, 0.5H).

Example 17

(S)-2-Ethylamino-6-(2-methyl-1-oxo-1,2-dihydroisoquinolin-5-yl)-6,7,7a,8,9,10-hexahydro-5H-pyrimido[5,4-f]pyrrolo[1,2-a][1,4]diazepin-5-one (Compound 17)

Step 1

(S)-6-(2-Methyl-1-oxo-1,2-dihydroisoquinolin-5-yl)-2-methylthio-6,7,7a,8,9,10-hexahydro-5H-pyrimido[5,4-f]pyrrolo[1,2-a][1,4]diazepin-5-one (179 mg, 29%) was obtained in the same manner as in step 1 of Example 1 using (S)-2-methylthio-6,7,7a,8,9,10-hexahydro-5H-pyrimido[5,4-f]pyrrolo[1,2-a][1,4]diazepin-5-one (132 mg, 0.530 mmol) obtained in Reference Example 3 of WO2008/149834, and Compound j (188 mg, 0.790 mmol) obtained in Reference Example 9, instead of Compound a.

ESI-MS: m/z 408 [M+H]$^+$. $^1$H-NMR (CDCl$_3$) δ (ppm): 1.63 (m, 1H), 1.95 (m, 1H), 2.08 (m, 1H), 2.20 (m, 1H), 2.57 (s, 3H), 3.48 (s, 3H), 3.56 (m, 1H), 3.71-4.21 (m, 4H), 6.29 (d, J=8.0 Hz, 0.6H), 6.42 (d, J=7.7 Hz, 0.4H), 7.05 (d, J=7.7 Hz, 0.4H), 7.10 (d, J=8.0 Hz, 0.6H), 7.44 (d, J=9.0 Hz, 0.4H), 7.45 (d, J=9.0 Hz, 0.6H), 7.47-7.57 (m, 1H), 8.43 (d, J=7.3 Hz, 0.4H), 8.44 (d, J=7.3 Hz, 0.6H), 8.85 (s, 0.6H), 8.92 (s, 0.4H).

Step 2

Compound 17 (62.2 mg, 61%) was obtained in the same manner as in step 2 of Example 1, using (S)-6-(2-methyl-1-oxo-1,2-dihydroisoquinolin-5-yl)-2-methylthio-6,7,7a,8,9,10-hexahydro-5H-pyrimido[5,4-f]pyrrolo[1,2-a][1,4]diazepin-5-one (103 mg, 0.252 mmol) obtained in step 1.

ESI-MS: m/z 405 [M+H]$^+$. $^1$H-NMR (CDCl$_3$) δ (ppm): 1.25 (t, J=7.3 Hz, 3H), 1.61 (m, 1H), 1.89 (m, 1H), 2.09 (m, 1H), 2.18 (m, 1H), 3.42-3.52 (m, 2H), 3.57 (m, 1H), 3.58 (s, 3H), 3.70-4.10 (m, 4H), 5.65 (br s, 1H), 6.32 (d, J=7.6 Hz, 0.6H), 6.44 (d, J=7.6 Hz, 0.4H), 7.06 (d, J=7.6 Hz, 0.4H), 7.08 (d, J=7.6 Hz, 0.6H), 7.41-7.53 (m, 2H), 8.42 (m, 1H), 8.80 (s, 0.6H), 8.85 (s, 0.4H).

Example 18

(S)-6-(2-Methyl-1-oxo-1,2-dihydroisoquinolin-5-yl)-2-methylamino-6,7,7a,8,9,10-hexahydro-5H-pyrimido[5,4-f]pyrrolo[1,2-a][1,4]diazepin-5-one (Compound 18)

Compound 18 (113 mg, 66%) was obtained in the same manner as in Example 2, using (S)-6-(2-methyl-1-oxo-1,2-dihydroisoquinolin-5-yl)-2-methylthio-6,7,7a,8,9,10-hexahydro-5H-pyrimido[5,4-f]pyrrolo[1,2-a][1,4]diazepin-5-one (179 mg, 0.440 mmol) obtained in step 1 of Example 17.

ESI-MS: m/z 391 [M+H]$^+$. $^1$H-NMR (CDCl$_3$) δ (ppm): 1.63 (m, 1H), 1.90 (m, 1H), 2.03 (m, 1H), 2.17 (m, 1H), 3.02 (s, 1.5H), 3.04 (s, 1.5H), 3.57-3.62 (m, 1H), 3.58 (s, 1.5H), 3.59 (s, 1.5H), 3.73-4.11 (m, 4H), 5.17 (br s, 1H), 6.33 (d, J=7.6 Hz, 0.5H), 6.45 (d, J=7.6 Hz, 0.5H), 7.06 (d, J=7.6 Hz, 0.5H), 7.09 (d, J=7.6 Hz, 0.5H), 7.42-7.54 (m, 2H), 8.41-8.45 (m, 1H), 8.82 (s, 0.5H), 8.87 (s, 0.5H).

Example 19

(S)-2-Ethylamino-6-(2-methyl-4-oxo-4H-pyrido[1,2-a]pyrimidin-6-yl)-6,7,7a,8,9,10-hexahydro-5H-pyrimido[5,4-f]pyrrolo[1,2-a][1,4]diazepin-5-one (Compound 19)

Step 1

(S)-6-(6-Aminopyridin-2-yl)-2-methylthio-6,7,7a,8,9,10-hexahydro-5H-pyrimido[5,4-f]pyrrolo[1,2-a][1,4]diazepin-5-one (0.584 g, 43%) was obtained in the same manner as in step 1 of Example 1, using (S)-2-methylthio-6,7,7a,8,9,10-hexahydro-5H-pyrimido[5,4-f]pyrrolo[1,2-a][1,4]diazepin-5-one obtained in Reference Example 3 of WO2008/149834, and 2-amino-6-bromopyridine (1.04 g, 5.99 mmol).

ESI-MS: m/z 343 [M+H]$^+$. $^1$H-NMR (CDCl$_3$) δ (ppm): 1.70 (m, 1H), 1.90 (m, 1H), 2.08 (m, 1H), 2.30 (m, 1H), 2.55 (s, 3H), 3.44 (dd, J=7.6, 14.9 Hz, 1H), 3.74-3.97 (m, 3H), 4.39 (s, 2H), 4.77 (d, J=14.9 Hz, 1H), 6.33 (d, J=7.9 Hz, 1H), 7.22 (d, J=7.6 Hz, 1H), 7.47 (dd, J=7.6, 7.9 Hz, 1H), 8.82 (s, 1H).

Step 2

Polyphosphoric acid (10.0 g) and ethyl acetoacetate (0.324 mL, 2.56 mmol) were added to (S)-6-(6-aminopyridin-2-yl)-2-methylthio-6,7,7a,8,9,10-hexahydro-5H-pyrimido[5,4-f]pyrrolo[1,2-a][1,4]diazepin-5-one (0.584 g, 1.71 mmol) obtained in step 1, and the mixture was stirred at 100° C. for 6.5 hours. The reaction mixture was poured into ice water, and neutralized with a 4.0 mol/L sodium hydroxide aqueous solution. The precipitated crystals were collected by filtration, and purified by silica gel column chromatography (ethyl acetate/methanol=3/1) to give (S)-6-(2-methyl-4-oxo-4H-pyrido[1,2-a]pyrimidin-6-yl)-2-methylthio-6,7,7a,8,9,10-hexahydro-5H-pyrimido[5,4-f]pyrrolo[1,2-a][1,4]diazepin-5-one (0.253 g, 36%).

ESI-MS: m/z 409 [M+H]$^+$. $^1$H-NMR (CDCl$_3$) δ (ppm): 1.64 (m, 1H), 1.91 (m, 1H), 2.03 (m, 1H), 2.21 (m, 1H), 2.35 (s, 1.5H), 2.37 (s, 1.5H), 2.50 (s, 3H), 3.62-4.16 (m, 4.5H), 4.85 (m, 0.5H), 6.11 (s, 0.5H), 6.16 (s, 0.5H), 6.70 (dd, J=1.7, 6.9 Hz, 0.5H), 6.76 (dd, J=2.3, 6.3 Hz, 0.5H), 7.36-7.59 (m, 2H), 8.76 (s, 0.5H), 8.79 (s, 0.5H).

Step 3

Compound 19 (96.4 mg, 77%) was obtained in the same manner as in step 2 of Example 1, using (S)-6-(2-methyl-4-oxo-4H-pyrido[1,2-a]pyrimidin-6-yl)-2-methylthio-6,7,7a,8,9,10-hexahydro-5H-pyrimido[5,4-f]pyrrolo[1,2-a][1,4]diazepin-5-one (126 mg, 0.310 mmol) obtained in step 2.

ESI-MS: m/z 406 [M+H]$^+$. $^1$H-NMR (CDCl$_3$) δ (ppm): 1.22 (t, J=7.3 Hz, 3H), 1.66 (m, 1H), 1.90 (m, 1H), 2.01 (m, 1H), 2.21 (m, 1H), 2.37 (s, 1.5H), 2.39 (s, 1.5H), 3.40-3.51 (m, 2H), 3.64-4.08 (m, 4.5H), 4.81 (m, 0.5H), 5.31 (br s, 1H), 6.15 (s, 0.5H), 6.18 (s, 0.5H), 6.69 (dd, J=1.5, 7.0 Hz, 0.5H), 6.74 (dd, J=1.8, 7.0 Hz, 0.5H), 7.43-7.59 (m, 2H), 8.77 (s, 0.5H), 8.80 (s, 0.5H).

Example 20

(S)-6-(2-Methyl-4-oxo-4H-pyrido[1,2-a]pyrimidin-6-yl)-2-methylamino-6,7,7a,8,9,10-hexahydro-5H-pyrimido[5,4-f]pyrrolo[1,2-a][1,4]diazepin-5-one (Compound 20)

Compound 20 (78.9 mg, 65%) was obtained in the same manner as in Example 2, using (S)-6-(2-methyl-4-oxo-4H-pyrido[1,2-a]pyrimidin-6-yl)-2-methylthio-6,7,7a,8,9,10-hexahydro-5H-pyrimido[5,4-f]pyrrolo[1,2-a][1,4]diazepin-5-one (126 mg, 0.310 mmol) obtained in step 2 of Example 19.

ESI-MS: m/z 392 [M+H]$^+$. $^1$H-NMR (CDCl$_3$) δ (ppm): 1.66 (m, 1H), 1.91 (m, 1H), 2.02 (m, 1H), 2.22 (m, 1H), 2.37 (s, 1.5H), 2.39 (s, 1.5H), 2.99 (d, J=5.5 Hz, 3H), 3.65-4.07 (m, 4.5H), 4.81 (m, 0.5H), 5.19 (br s, 1H), 6.15 (s, 0.5H), 6.19 (s, 0.5H), 6.69 (dd, J=1.5, 7.0 Hz, 0.5H), 6.74 (dd, J=1.8, 7.0 Hz, 0.5H), 7.43-7.60 (m, 2H), 8.79 (s, 0.5H), 8.80 (s, 0.5H).

Example 21

(S)-2-Ethylamino-6-(quinolin-8-yl)-6,7,7a,8,9,10-hexahydro-5H-pyrimido[5,4-f]pyrrolo[1,2-a][1,4]diazepin-5-one (Compound 21)

Step 1

(S)-2-Methylthio-6-(quinolin-8-yl)-6,7,7a,8,9,10-hexahydro-5H-pyrimido[5,4-f]pyrrolo[1,2-a][1,4]diazepin-5-one (741 mg, 97%) was obtained in the same manner as in step 1 of Example 1 using (S)-2-methylthio-6,7,7a,8,9,10-hexahydro-5H-pyrimido[5,4-f]pyrrolo[1,2-a][1,4]diazepin-5-one (509 mg, 2.03 mmol) obtained in Reference Example 3 of WO2008/149834, and commercially available 8-bromoquinoline (0.400 mL, 3.06 mmol), instead of Compound a.

ESI-MS: m/z 378 [M+H]$^+$. $^1$H-NMR (CDCl$_3$) δ (ppm): 1.54-1.72 (m, 1H), 1.84-2.23 (m, 3H), 2.57 (s, 3H), 3.75-4.17 (m, 5H), 7.40-7.46 (m, 1H), 7.54-7.62 (m, 1H), 7.65-7.70 (m, 1H), 7.80-7.85 (m, 1H), 8.17-8.23 (m, 1H), 8.88-8.93 (m, 2H).

Step 2

(S)-2-Methylthio-6-(quinolin-8-yl)-6,7,7a,8,9,10-hexahydro-5H-pyrimido[5,4-f]pyrrolo[1,2-a][1,4]diazepin-5-one (343 mg, 0.909 mmol) obtained in step 1 was dissolved in dichloromethane (3 mL), and m-CPBA (266 mg, 1.00 mmol) was added. The mixture was stirred under ice-cooled condition for 10 minutes. The reaction mixture was diluted by adding chloroform, and washed with a saturated sodium bicarbonate aqueous solution and saturated brine. The organic layer was dried over anhydrous magnesium sulfate, and concentrated under reduced pressure. The obtained residue was dissolved in THF (3 mL), and a 2.0 mol/L ethylamine/THF solution (2.00 mL, 4.00 mmol) was added. The mixture was stirred at room temperature for 2 hours. After concentrating the reaction mixture under reduced pressure, the obtained residue was purified by silica gel column chromatography (chloroform/methanol) to give Compound 21 (258 mg, 76%).

ESI-MS: m/z 375 [M+H]$^+$. $^1$H-NMR (CDCl$_3$) δ (ppm): 1.21-1.28 (m, 3H), 1.45-1.70 (m, 1H), 1.77-2.25 (m, 3H), 3.42-3.54 (m, 2H), 3.65-4.10 (m, 5H), 5.11 (br s, 1H), 7.38-7.44 (m, 1H), 7.53-7.61 (m, 1H), 7.64-7.69 (m, 1H), 7.77-7.83 (m, 1H), 8.15-8.21 (m, 1H), 8.85 (s, 1H), 8.88-8.92 (m, 1H).

Example 22

(S)-2-Methylamino-6-(quinolin-8-yl)-6,7,7a,8,9,10-hexahydro-5H-pyrimido[5,4-f]pyrrolo[1,2-a][1,4]diazepin-5-one (Compound 22)

(S)-2-Methylthio-6-(quinolin-8-yl)-6,7,7a,8,9,10-hexahydro-5H-pyrimido[5,4-f]pyrrolo[1,2-a][1,4]diazepin-5-one (343 mg, 0.909 mmol) obtained in step 1 of Example 21 was dissolved in dichloromethane (3 mL), and m-CPBA (266 mg, 1.00 mmol) was added. The mixture was stirred under ice-cooled condition for 10 minutes. The reaction mixture was diluted by adding chloroform, and washed with a saturated sodium bicarbonate aqueous solution and saturated brine. The organic layer was dried over anhydrous magnesium sulfate, and concentrated under reduced pressure. The obtained residue was dissolved in THF (3 mL), and a 2.0 mol/L methylamine/THF solution (2.00 mL, 4.00 mmol) was added. The mixture was stirred at room temperature for 2 hours. After concentrating the reaction mixture under reduced pressure, the obtained residue was purified by silica gel column chromatography (chloroform/methanol) to give Compound 22 (289 mg, 88%).

ESI-MS: m/z 361 [M+H]$^+$. $^1$H-NMR (CDCl$_3$) δ (ppm): 1.51-1.71 (m, 1H), 1.79-2.20 (m, 3H), 3.02 (s, 1.5H), 3.04 (s, 1.5H), 3.68-4.10 (m, 5H), 5.12 (br s, 1H), 7.38-7.45 (m, 1H), 7.53-7.61 (m, 1H), 7.63-7.70 (m, 1H), 7.77-7.83 (m, 1H), 8.16-8.22 (m, 1H), 8.86 (s, 1H), 8.88-8.92 (m, 1H).

Example 23

(S)-2-Ethylamino-6-(isoquinolin-8-yl)-6,7,7a,8,9,10-hexahydro-5H-pyrimido[5,4-f]pyrrolo[1,2-a][1,4]diazepin-5-one (Compound 23)

Step 1

(S)-6-(Isoquinolin-8-yl)-2-methylthio-6,7,7a,8,9,10-hexahydro-5H-pyrimido[5,4-f]pyrrolo[1,2-a][1,4]diazepin-5-one (193 mg, 30%) was obtained in the same manner as in step 1 of Example 21 using (S)-2-methylthio-6,7,7a,8,9,10-hexahydro-5H-pyrimido[5,4-f]pyrrolo[1,2-a][1,4]diazepin-5-one (427 mg, 1.71 mmol) obtained in Reference Example 3 of WO2008/149834, and commercially available 8-bromoisoquinoline (390 mg, 2.44 mmol), instead of 8-bromoquinoline.

ESI-MS: m/z 378 [M+H]$^+$. $^1$H-NMR (CDCl$_3$) δ (ppm): 1.54-1.77 (m, 1H), 1.83-2.26 (m, 3H), 2.58 (s, 3H), 3.69-4.31 (m, 5H), 7.41 (dd, J=7.2, 1.0 Hz, 0.4H), 7.49 (dd, J=7.2, 1.0 Hz, 0.6H), 7.67-7.78 (m, 2H), 7.80-7.88 (m, 1H), 8.56-8.63 (m, 1H), 8.89 (s, 0.6H), 8.94 (s, 0.4H), 9.20 (s, 0.6H), 9.29 (s, 0.4H).

Step 2

Compound 23 (70.2 mg, 78%) was obtained in the same manner as in step 2 of Example 21, using (S)-6-(isoquinolin-8-yl)-2-methylthio-6,7,7a,8,9,10-hexahydro-5H-pyrimido[5,4-f]pyrrolo[1,2-a][1,4]diazepin-5-one (91.0 mg, 0.241 mmol) obtained in step 1.

ESI-MS: m/z 375 [M+H]$^+$. $^1$H-NMR (CDCl$_3$) δ (ppm): 1.19-1.31 (m, 3H), 1.54-1.74 (m, 1H), 1.79-2.21 (m, 3H), 3.43-3.55 (m, 2H), 3.65-4.24 (m, 5H), 5.57 (br s, 1H), 7.40 (dd, J=7.1, 1.0 Hz, 0.4H), 7.48 (dd, J=7.1, 1.0 Hz, 0.6H), 7.67-7.85 (m, 3H), 8.54-8.60 (m, 1H), 8.79-8.90 (m, 1H), 9.21 (s, 0.6H), 9.32 (s, 0.4H).

Example 24

(S)-(Isoquinolin-8-yl)-2-methylamino-6,7,7a,8,9,10-hexahydro-5H-pyrimido[5,4-f]pyrrolo[1,2-a][1,4]diazepin-5-one (Compound 24)

Compound 24 (86.5 mg, 99%) was obtained in the same manner as in Example 22, using (S)-6-(isoquinolin-8-yl)-2-methylthio-6,7,7a,8,9,10-hexahydro-5H-pyrimido[5,4-f]pyrrolo[1,2-a][1,4]diazepin-5-one (91.0 mg, 0.241 mmol) obtained in step 1 of Example 23.

ESI-MS: m/z 361 [M+H]$^+$. $^1$H-NMR (CDCl$_3$) δ (ppm): 1.55-2.22 (m, 4H), 3.02-3.06 (m, 3H), 3.64-4.25 (m, 5H), 5.29 (br s, 1H), 7.40 (dd, J=7.1, 1.0 Hz, 0.4H), 7.48 (dd, J=7.1, 1.0 Hz, 0.6H), 7.67-7.85 (m, 3H), 8.54-8.61 (m, 1H), 8.79-8.91 (m, 1H), 9.21 (s, 0.6H), 9.32 (s, 0.4H).

Example 25

(S)-2-Ethylamino-6-(isoquinolin-5-yl)-6,7,7a,8,9,10-hexahydro-5H-pyrimido[5,4-f]pyrrolo[1,2-a][1,4]diazepin-5-one (Compound 25)

Step 1

(S)-6-(Isoquinolin-5-yl)-2-methylthio-6,7,7a,8,9,10-hexahydro-5H-pyrimido[5,4-f]pyrrolo[1,2-a][1,4]diazepin-5-one (802 mg, quantitative yield) was obtained in the same manner as in step 1 of Example 21 using (S)-2-methylthio-6,7,7a,8,9,10-hexahydro-5H-pyrimido[5,4-f]pyrrolo[1,2-a][1,4]diazepin-5-one (530 mg, 2.12 mmol) obtained in Reference Example 3 of WO2008/149834, and commercially available 5-bromoisoquinoline (674 mg, 2.44 mmol), instead of 8-bromoquinoline.

ESI-MS: m/z 378 [M+H]$^+$.

Step 2

Compound 25 (56.3 mg, 47%) was obtained in the same manner as in step 2 of Example 21, using (S)-6-(isoquinolin-5-yl)-2-methylthio-6,7,7a,8,9,10-hexahydro-5H-pyrimido[5,4-f]pyrrolo[1,2-a][1,4]diazepin-5-one (121 mg, 0.320 mmol) obtained in step 1.

ESI-MS: m/z 375 [M+H]$^+$. $^1$H-NMR (CDCl$_3$) δ (ppm): 1.26 (t, J=7.1 Hz, 3H), 1.54-1.75 (m, 1H), 1.76-2.21 (m, 3H), 3.43-3.55 (m, 2H), 3.57-4.15 (m, 5H), 5.42 (br s, 1H), 7.51-7.56 (m, 1H), 7.58-7.69 (m, 2H), 7.91-8.02 (m, 1H), 8.53-8.58 (m, 1H), 8.81-8.89 (m, 1H), 9.31 (s, 1H).

Example 26

(S)-6-(Isoquinolin-5-yl)-2-methylamino-6,7,7a,8,9,10-hexahydro-5H-pyrimido[5,4-f]pyrrolo[1,2-a][1,4]diazepin-5-one (Compound 26)

Compound 26 (85.3 mg, 74%) was obtained in the same manner as in Example 22, using (S)-6-(isoquinolin-5-yl)-2- methylthio-6,7,7a,8,9,10-hexahydro-5H-pyrimido[5,4-f] pyrrolo[1,2-a][1,4]diazepin-5-one (121 mg, 0.320 mmol) obtained in step 1 of Example 25.

ESI-MS: m/z 361 [M+H]$^+$. $^1$H-NMR (CDCl$_3$) δ (ppm): 1.53-1.74 (m, 1H), 1.80-2.21 (m, 3H), 3.02 (s, 1.5H), 3.04 (s, 1.5H), 3.57-4.16 (m, 5H), 5.61 (br s, 1H), 7.50-7.56 (m, 1H), 7.59-7.68 (m, 2H), 7.92-8.00 (m, 1H), 8.53-8.58 (m, 1H), 8.78-8.91 (m, 1H), 9.30 (s, 1H).

Example 27

(S)-2-Ethylamino-6-(quinolin-5-yl)-6,7,7a,8,9,10-hexahydro-5H-pyrimido[5,4-f]pyrrolo[1,2-a][1,4]diazepin-5-one (Compound 27)

Step 1

(S)-2-Methylthio-6-(quinolin-5-yl)-6,7,7a,8,9,10-hexahydro-5H-pyrimido[5,4-f]pyrrolo[1,2-a][1,4]diazepin-5-one (765 mg, quantitative yield) was obtained in the same manner as in step 1 of Example 21 using (S)-2-methylthio-6,7,7a,8,9,10-hexahydro-5H-pyrimido[5,4-f]pyrrolo[1,2-a][1,4]diazepin-5-one (509 mg, 2.03 mmol) obtained in Reference Example 3 of WO2008/149834, and commercially available 5-bromoquinoline (617 mg, 3.00 mmol), instead of 8-bromoquinoline.

ESI-MS: m/z 378 [M+H]$^+$. $^1$H-NMR (CDCl$_3$) δ (ppm): 1.52-1.78 (m, 1H), 1.83-2.29 (m, 3H), 2.58 (s, 3H), 3.65-4.25 (m, 5H), 7.36-7.50 (m, 2H), 7.71-7.81 (m, 1H), 8.01-8.19 (m, 2H), 8.87-9.00 (m, 2H).

Step 2

Compound 27 (373 mg, 99%) was obtained in the same manner as in step 2 of Example 21, using (S)-2-methylthio-6-(quinolin-5-yl)-6,7,7a,8,9,10-hexahydro-5H-pyrimido[5,4-f]pyrrolo[1,2-a][1,4]diazepin-5-one (383 mg, 1.01 mmol) obtained in step 1.

ESI-MS: m/z 375 [M+H]$^+$. $^1$H-NMR (CDCl$_3$) δ (ppm): 1.22-1.30 (m, 3H), 1.53-1.76 (m, 1H), 1.81-2.25 (m, 3H), 3.43-3.56 (m, 2H), 3.57-4.18 (m, 5H), 5.34 (br s, 1H), 7.35-7.49 (m, 2H), 7.70-7.80 (m, 1H), 8.03-8.20 (m, 2H), 8.79-8.90 (m, 1H), 8.90-8.97 (m, 1H).

Example 28

(S)-2-Methylamino-6-(quinolin-5-yl)-6,7,7a,8,9,10-hexahydro-5H-pyrimido[5,4-f]pyrrolo[1,2-a][1,4]diazepin-5-one (Compound 28)

Compound 28 (79.3 mg, 22%) was obtained in the same manner as in Example 22, using (S)-2-methylthio-6-(quinolin-5-yl)-6,7,7a,8,9,10-hexahydro-5H-pyrimido[5,4-f]pyrrolo[1,2-a][1,4]diazepin-5-one (383 mg, 1.01 mmol) obtained in step 1 of Example 27.

ESI-MS: m/z 361 [M+H]$^+$. $^1$H-NMR (CDCl$_3$) δ (ppm): 1.53-1.75 (m, 1H), 1.79-2.25 (m, 3H), 3.03 (s, 1.5H), 3.05 (s, 1.5H), 3.58-4.21 (m, 5H), 5.47 (br s, 1H), 7.36-7.49 (m, 2H), 7.70-7.79 (m, 1H), 8.04-8.20 (m, 2H), 8.79-8.90 (m, 1H), 8.92-8.97 (m, 1H).

Example 29

(S)-2-Ethylamino-6-(2-methyl-1-oxo-1,2-dihydroisoquinolin-8-yl)-6,7,7a,8,9,10-hexahydro-5H-pyrimido[5,4-f]pyrrolo[1,2-a][1,4]diazepin-5-one (Compound 29)

Step 1

(S)-6-(2-Methyl-1-oxo-1,2-dihydroisoquinolin-8-yl)-2-methylthio-6,7,7a,8,9,10-hexahydro-5H-pyrimido[5,4-f]pyrrolo[1,2-a][1,4]diazepin-5-one (117 mg, 28%) was obtained in the same manner as in step 1 of Example 21 using (S)-2-methylthio-6,7,7a,8,9,10-hexahydro-5H-pyrimido[5,4-f]pyrrolo[1,2-a][1,4]diazepin-5-one (260 mg, 1.04 mmol) obtained in Reference Example 3 of WO2008/149834, and Compound k (295 mg, 1.24 mmol) obtained in Reference Example 10, instead of 8-bromoisoquinoline.

ESI-MS: m/z 408 [M+H]$^+$. $^1$H-NMR (CDCl$_3$) δ (ppm): 1.53-1.74 (m, 1H), 1.81-2.24 (m, 3H), 2.55 (s, 3H), 3.46-4.24 (m, 8H), 6.48 (d, J=7.2 Hz, 1H), 7.09 (d, J=7.2 Hz, 1H), 7.17 (d, J=7.6 Hz, 0.4H), 7.25 (d, J=7.6 Hz, 0.6H), 7.44-7.68 (m, 2H), 8.92 (s, 0.6H), 8.95 (s, 0.4H).

Step 2

Compound 29 (27.4 mg, 52%) was obtained in the same manner as in step 2 of Example 21, using (S)-6-(2-methyl-1-oxo-1,2-dihydroisoquinolin-8-yl)-2-methylthio-6,7,7a,8,9,10-hexahydro-5H-pyrimido[5,4-f]pyrrolo[1,2-a][1,4]diazepin-5-one (52.5 mg, 0.129 mmol) obtained in step 1.

ESI-MS: m/z 405 [M+H]$^+$. $^1$H-NMR (CDCl$_3$) δ (ppm): 1.18-1.33 (m, 3H), 1.51-1.74 (m, 1H), 1.76-2.27 (m, 3H), 3.37-4.24 (m, 10H), 5.49 (br s, 1H), 6.46 (d, J=7.2 Hz, 1H), 7.07 (d, J=7.2 Hz, 1H), 7.16 (dd, J=7.6, 1.3 Hz, 0.4H), 7.22-7.30 (m, 0.6H), 7.41-7.69 (m, 2H), 8.79-8.91 (m, 1H).

Example 30

(S)-6-(2-Methyl-1-oxo-1,2-dihydroisoquinolin-8-yl)-2-methylamino-6,7,7a,8,9,10-hexahydro-5H-pyrimido[5,4-f]pyrrolo[1,2-a][1,4]diazepin-5-one (Compound 30)

Compound 30 (50.2 mg, quantitative yield) was obtained in the same manner as in Example 22, using (S)-6-(2-methyl-1-oxo-1,2-dihydroisoquinolin-8-yl)-2-methylthio-6,7,7a,8,9,10-hexahydro-5H-pyrimido[5,4-f]pyrrolo[1,2-a][1,4]diazepin-5-one (52.5 mg, 0.129 mmol) obtained in step 1 of Example 29.

ESI-MS: m/z 391 [M+H]$^+$. $^1$H-NMR (CDCl$_3$) δ (ppm): 1.50-1.72 (m, 1H), 1.76-2.18 (m, 3H), 2.92-3.03 (m, 3H), 3.42-4.21 (m, 8H), 5.50 (br s, 1H), 6.39-6.51 (m, 1H), 7.00-7.10 (m, 1H), 7.17 (dd, J=7.6, 1.3 Hz, 0.4H), 7.22-7.28 (m, 0.6H), 7.41-7.68 (m, 2H), 8.75-8.91 (m, 1H).

Example 31

(S)-2-Ethylamino-6-(1-methyl-2-oxo-1,2-dihydroquinolin-5-yl)-6,7,7a,8,9,10-hexahydro-5H-pyrimido[5,4-f]pyrrolo[1,2-a][1,4]diazepin-5-one (Compound 31)

Step 1

(S)-6-(1-Methyl-2-oxo-1,2-dihydroquinolin-5-yl)-2-methylthio-6,7,7a,8,9,10-hexahydro-5H-pyrimido[5,4-f]pyrrolo[1,2-a][1,4]diazepin-5-one (119 mg, 30%) was obtained in the same manner as in step 1 of Example 21 using (S)-2-methylthio-6,7,7a,8,9,10-hexahydro-5H-pyrimido[5,4-f]pyrrolo[1,2-a][1,4]diazepin-5-one (240 mg, 0.959 mmol) obtained in Reference Example 3 of WO2008/149834, and Compound m (240 mg, 1.01 mmol) obtained in Reference Example 11, instead of 8-bromoisoquinoline.

ESI-MS: m/z 408 [M+H]$^+$. $^1$H-NMR (CDCl$_3$) δ (ppm): 1.57-1.77 (m, 1H), 1.82-2.31 (m, 3H), 2.56 (s, 3H), 3.68-3.75 (m, 3H), 3.83-4.16 (m, 5H), 6.65-6.75 (m, 1H), 6.99 (d, J=7.6 Hz, 0.4H), 7.07 (d, J=7.6 Hz, 0.6H), 7.28-7.37 (m, 1H), 7.46-7.67 (m, 2H), 8.87 (s, 0.6H), 8.92 (s, 0.4H).

Step 2

Compound 31 (47.2 mg, 70%) was obtained in the same manner as in step 2 of Example 21, using (S)-6-(1-methyl-2-oxo-1,2-dihydroquinolin-5-yl)-2-methylthio-6,7,7a,8,9,10-hexahydro-5H-pyrimido[5,4-f]pyrrolo[1,2-a][1,4]diazepin-5-one (67.5 mg, 0.166 mmol) obtained in step 1.

ESI-MS: m/z 405 [M+H]$^+$. $^1$H-NMR (CDCl$_3$) δ (ppm): 1.21-1.29 (m, 3H), 1.55-1.79 (m, 1H), 1.81-2.26 (m, 3H), 3.43-3.54 (m, 2H), 3.72-4.12 (m, 8H), 5.32 (br s, 1H), 6.70-6.77 (m, 1H), 7.01-7.14 (m, 1H), 7.32-7.39 (m, 1H), 7.55-7.73 (m, 2H), 8.76-8.89 (m, 1H).

Example 32

(S)-6-(1-Methyl-2-oxo-1,2-dihydroquinolin-5-yl)-2-methylamino-6,7,7a,8,9,10-hexahydro-5H-pyrimido[5,4-f]pyrrolo[1,2-a][1,4]diazepin-5-one (Compound 32)

Compound 32 (45.5 mg, 70%) was obtained in the same manner as in Example 22, using (S)-6-(1-methyl-2-oxo-1,2-dihydroquinolin-5-yl)-2-methylthio-6,7,7a,8,9,10-hexahydro-5H-pyrimido[5,4-f]pyrrolo[1,2-a][1,4]diazepin-5-one (67.5 mg, 0.166 mmol) obtained in step 1 of Example 31.

ESI-MS: m/z 391 [M+H]$^+$. $^1$H-NMR (CDCl$_3$) δ (ppm): 1.58-1.77 (m, 1H), 1.80-2.44 (m, 3H), 3.00-3.06 (m, 3H), 3.72-4.14 (m, 8H), 6.71-6.77 (m, 1H), 7.02-7.14 (m, 1H), 7.33-7.39 (m, 1H), 7.55-7.72 (m, 2H), 8.74-8.89 (m, 1H).

Example 33

(S)-2-Amino-6-(3-ethyl-4-oxo-3,4-dihydroquinazolin-8-yl)-6,7,7a,8,9,10-hexahydro-5H-pyrimido[5,4-f]pyrrolo[1,2-a][1,4]diazepin-5-one (Compound 33)

(S)-6-(3-Ethyl-4-oxo-3,4-dihydroquinazolin-8-yl)-2-methylthio-6,7,7a,8,9,10-hexahydro-5H-pyrimido[5,4-f]pyrrolo[1,2-a][1,4]diazepin-5-one (295 mg, 0.698 mmol) obtained in step 1 of Example 13 was dissolved in dichloromethane (3 mL), and m-CPBA (222 mg, 0.838 mmol) was added. The mixture was stirred for 0.25 hours. The reaction mixture was diluted by adding chloroform, and washed with a saturated sodium bicarbonate aqueous solution and saturated brine. The organic layer was dried over anhydrous magnesium sulfate, and concentrated under reduced pressure. The obtained residue was dissolved in THF (1 mL), and 25% ammonia water (1.00 mL, 14.6 mmol) was added. The mixture was stirred overnight at room temperature. After concentrating the reaction mixture under reduced pressure, the obtained residue was purified by silica gel column chromatography (chloroform/methanol=97/3) to give Compound 33 (210 mg, 0.536 mmol, 77%).

ESI-MS: m/z 392 [M+H]$^+$. $^1$H-NMR (CDCl$_3$) δ (ppm): 1.41 (t, J=7.3 Hz, 3H), 1.55-1.68 (m, 1H), 1.80-2.24 (m, 4H), 3.58-4.51 (m, 7H), 5.17 (br s, 2H), 7.53 (dd, J=7.8, 7.8 Hz, 1H), 7.66 (d, J=7.8 Hz, 1H), 8.03 (s, 1H), 8.30 (d, J=7.8 Hz, 1H), 8.83 (s, 1H).

Example 34

(S)-6-(3-(2-Methoxyethyl)-4-oxo-3,4-dihydroquinazolin-8-yl)-2-(methylamino)-6,7,7a,8,9,10-hexahydro-5H-pyrimido[5,4-f]pyrrolo[1,2-a][1,4]diazepin-5-one (Compound 34)

Step 1

Toluene (4 mL), N,N'-dimethylethylenediamine (0.179 mL, 1.68 mmol), and copper(I) iodide (152 mg, 0.799 mmol) were successively added to a mixture of (S)-2-methylthio-6,7,7a,8,9,10-hexahydro-5H-pyrimido[5,4-f]pyrrolo[1,2-a][1,4]diazepin-5-one (200 mg, 0.799 mmol) obtained in Reference Example 3 of WO2008/149834, Compound aa (339 mg, 1.20 mmol) obtained in Reference Example 13, and potassium carbonate (331 mg, 2.40 mmol). The mixture was stirred under a nitrogen atmosphere at 110° C. for 3 hours. The mixture was further stirred under a nitrogen atmosphere at 110° C. for 2 hours after adding Compound aa (226 mg, 0.799 mmol), N,N'-dimethylethylenediamine (0.179 mL, 1.68 mmol), and copper(I) iodide (152 mg, 0.799 mmol). The reaction mixture was cooled to room temperature, and filtered through Celite. The filtrate was concentrated under reduced pressure. The obtained residue was purified by silica gel column chromatography (chloroform/methanol) to give (S)-6-(3-(2-methoxyethyl)-4-oxo-3,4-dihydroquinazolin-8-yl)-2-(methylthio)-6,7,7a,8,9,10-hexahydro-5H-pyrimido[5,4-f]pyrrolo[1,2-a][1,4]diazepin-5-one (365 mg, >99%).

ESI-MS: m/z 453 [M+H]$^+$. $^1$H-NMR (CDCl$_3$) δ (ppm): 8.89 (s, 1H), 8.30 (d, J=7.8 Hz, 1H), 8.06 (s, 1H), 7.68 (d, J=7.8 Hz, 1H), 7.53 (dd, J=7.8, 7.8 Hz, 1H), 4.41 (br s, 1H), 4.16 (t, J=4.9 Hz, 2H), 4.01-3.79 (m, 3H), 3.79-3.62 (m, 3H), 3.33 (s, 3H), 2.56 (s, 3H), 2.27-2.14 (m, 1H), 2.13-2.02 (m, 1H), 2.02-1.86 (m, 1H), 1.74-1.60 (m, 1H).

Step 2

(S)-6-(3-(2-Methoxyethyl)-4-oxo-3,4-dihydroquinazolin-8-yl)-2-(methylthio)-6,7,7a,8,9,10-hexahydro-5H-pyrimido[5,4-f]pyrrolo[1,2-a][1,4]diazepin-5-one (360 mg, 0.796 mmol) obtained in step 1 was dissolved in dichloromethane (8 mL), and m-CPBA (232 mg, 0.875 mmol) was added at 0° C. The mixture was stirred at 0° C. for 15 minutes. After adding a saturated sodium bicarbonate aqueous solution and saturated brine, the reaction mixture was extracted with chloroform. The organic layer was dried over anhydrous sodium sulfate, and concentrated under reduced pressure to give a residue.

Step 3

A 2 mol/L methylamine/THF solution (1.99 mL, 3.98 mmol) was added to a half amount of the residue obtained in step 2, and the mixture was stirred overnight at room temperature. The reaction mixture was concentrated under reduced pressure, and the obtained residue was purified by silica gel column chromatography (chloroform/methanol). The obtained crude product was dissolved in chloroform, and dropped into diisopropyl ether. The precipitated solid was collected by filtration, and dried under reduced pressure to give Compound 34 (128 mg, 2 steps 74%).

ESI-MS: m/z 436 [M+H]$^+$. $^1$H-NMR (CDCl$_3$) δ (ppm): 8.83 (s, 1H), 8.27 (dd, J=8.1, 1.5 Hz, 1H), 8.06 (s, 1H), 7.68 (dd, J=7.5, 1.3 Hz, 1H), 7.50 (dd, J=7.9, 7.9 Hz, 1H), 5.42 (br s, 1H), 4.30 (br s, 1H), 4.15 (t, J=4.8 Hz, 2H), 4.02-3.75 (m, 3H), 3.73-3.63 (m, 3H), 3.32 (s, 3H), 3.01 (d, J=5.1 Hz, 3H), 2.24-1.78 (m, 3H), 1.71-1.51 (m, 1H).

Example 35

(S)-2-(Ethylamino)-6-(3-(2-methoxyethyl)-4-oxo-3,4-dihydroquinazolin-8-yl)-6,7,7a,8,9,10-hexahydro-5H-pyrimido[5,4-f]pyrrolo[1,2-a][1,4]diazepin-5-one (Compound 35)

A 2 mol/L ethylamine/THF solution (1.99 mL, 3.98 mmol) was added to a half amount of the residue obtained in step 2 of Example 34, and the mixture was stirred overnight at room temperature. The reaction mixture was concentrated under reduced pressure, and the obtained residue was purified by silica gel column chromatography (chloroform/methanol). The obtained crude product was dissolved in chloroform, and dropped into diisopropyl ether. The precipitated solid was collected by filtration, and dried under reduced pressure to give Compound 35 (152 mg, 2 steps 85%).

ESI-MS: m/z 450 [M+H]$^+$. $^1$H-NMR (CDCl$_3$) δ (ppm): 8.82 (s, 1H), 8.27 (dd, J=7.9, 1.6 Hz, 1H), 8.06 (s, 1H), 7.67 (dd, J=7.7, 1.5 Hz, 1H), 7.50 (dd, J=7.9, 7.9 Hz, 1H), 5.50 (br s, 1H), 4.29 (br s, 1H), 4.15 (t, J=4.8 Hz, 2H), 4.00-3.74 (m, 3H), 3.74-3.62 (m, 3H), 3.47 (dt, J=13.8, 6.6 Hz, 2H), 3.32 (s, 3H), 2.21-1.78 (m, 3H), 1.71-1.53 (m, 1H), 1.24 (t, J=7.1 Hz, 3H).

Example 36

(S)-6-(3-(3-Methoxypropyl)-4-oxo-3,4-dihydroquinazolin-8-yl)-2-(methylamino)-6,7,7a,8,9,10-hexahydro-5H-pyrimido[5,4-f]pyrrolo[1,2-a][1,4]diazepin-5-one (Compound 36)

Compound 36 was obtained in the same manner as in Example 34, using Compound ab obtained in Reference Example 14.

ESI-MS: m/z 450 [M+H]$^+$. $^1$H-NMR (CDCl$_3$) δ (ppm): 8.83 (br s, 1H), 8.27 (d, J=7.8 Hz, 1H), 8.02 (s, 1H), 7.67 (d, J=7.8 Hz, 1H), 7.51 (dd, J=7.8, 7.8 Hz, 1H), 5.45 (br s, 1H), 4.43-4.20 (m, 1H), 4.08 (t, J=6.8 Hz, 2H), 4.02-3.74 (m, 3H), 3.68 (d, J=14.6 Hz, 1H), 3.42 (t, J=5.9 Hz, 2H), 3.34 (s, 3H), 3.01 (d, J=5.9 Hz, 3H), 2.19-2.10 (m, 1H), 2.10-1.97 (m, 1H), 1.97-1.81 (m, 3H), 1.70-1.55 (m, 1H).

Example 37

(S)-6-(3-(3-Methoxypropyl)-4-oxo-3,4-dihydroquinazolin-8-yl)-2-(ethylamino)-6,7,7a,8,9,10-hexahydro-5H-pyrimido[5,4-f]pyrrolo[1,2-a][1,4]diazepin-5-one (Compound 37)

Compound 37 was obtained in the same manner as in steps 1 and 2 of Example 34, and Example 35, using Compound ab obtained in Reference Example 14.

ESI-MS: m/z 464 [M+H]$^+$. $^1$H-NMR (CDCl$_3$) δ (ppm): 8.82 (br s, 1H), 8.27 (d, J=8.8 Hz, 1H), 8.01 (s, 1H), 7.67 (d, J=7.8 Hz, 1H), 7.51 (dd, J=7.8, 7.8 Hz, 1H), 5.40 (br s, 1H), 4.47-4.15 (m, 1H), 4.08 (t, J=6.8 Hz, 2H), 4.01-3.72 (m, 3H), 3.67 (d, J=14.6 Hz, 1H), 3.52-3.38 (m, 4H), 3.34 (s, 3H), 2.20-1.97 (m, 4H), 1.96-1.81 (m, 1H), 1.68-1.55 (m, 1H), 1.24 (t, J=6.8 Hz, 3H).

Example 38

(S)-6-(3-(3-(Dimethylamino)propyl)-4-oxo-3,4-dihydroquinazolin-8-yl)-2-(methylamino)-6,7,7a,8,9,10-hexahydro-5H-pyrimido[5,4-f]pyrrolo[1,2-a][1,4]diazepin-5-one (Compound 38)

Step 1

Toluene (4 mL), N,N'-dimethylethylenediamine (0.180 mL, 1.68 mmol), and copper(I) iodide (152 mg, 0.799 mmol) were successively added to a mixture of (S)-2-methylthio-6,7,7a,8,9,10-hexahydro-5H-pyrimido[5,4-f]pyrrolo[1,2-a][1,4]diazepin-5-one (200 mg, 0.799 mmol) obtained in Reference Example 3 of WO2008/149834, and potassium carbonate (331 mg, 2.40 mmol). The mixture was stirred under a nitrogen atmosphere at room temperature for 5 minutes, and Compound ac (267 mg, 8.99 mmol) obtained in Reference Example 15 was added. The mixture was stirred under a nitrogen atmosphere at 110° C. for 2 hours. Then, N,N'-dimethylethylenediamine (0.180 mL, 1.68 mmol), and copper(I) iodide (152 mg, 0.799 mmol) were added, and the reaction mixture was stirred under a nitrogen atmosphere at 110° C. for 2 hours. The reaction mixture was cooled to room temperature, and filtered through Celite. The filtrate was concentrated under reduced pressure. The obtained residue was purified by silica gel column chromatography (chloroform/methanol) to give (S)-6-(3-(3-(dimethylamino)propyl)-4-oxo-3,4-dihydroquinazolin-8-yl)-2-(methylthio)-6,7,7a,8,9,10-hexahydro-5H-pyrimido[5,4-f]pyrrolo[1,2-a][1,4]diazepin-5-one (457 mg).

Step 2

(S)-6-(3-(3-(Dimethylamino)propyl)-4-oxo-3,4-dihydroquinazolin-8-yl)-2-(methylthio)-6,7,7a,8,9,10-hexahydro-5H-pyrimido[5,4-f]pyrrolo[1,2-a][1,4]diazepin-5-one (100 mg) obtained in step 1 was dissolved in dichloromethane (1.9 mL), and 4-toluenesulfonic acid monohydrate (48 mg, 0.250 mmol) was added. The mixture was sonicated until all the solid dissolved. After cooling the reaction mixture to 0° C., m-CPBA (61 mg, 0.229 mmol) was added, and the mixture was stirred at 0° C. for 15 minutes. The reaction mixture was extracted with chloroform after adding saturated sodium bicarbonate aqueous solution and saturated brine. The organic layer was dried over anhydrous sodium sulfate, and concentrated under reduced pressure to give a residue.

Step 3

A 2 mol/L methylamine/THF solution (1.05 mL, 2.09 mmol) was added to the residue obtained in step 2, and the mixture was stirred at room temperature for 2 hours. After concentrating the reaction mixture under reduced pressure, the obtained residue was purified by silica gel column chromatography (ethyl acetate/methanol), and suspended in diethyl ether. The insoluble matter was collected by filtration, and dried under reduced pressure to give Compound 38 (23.8 mg, 3 steps 25%).

ESI-MS: m/z 463 [M+H]$^+$. $^1$H-NMR (CDCl$_3$) δ (ppm): 8.84 (s, 1H), 8.30-8.25 (m, 1H), 8.07 (s, 1H), 7.67 (d, J=7.8 Hz, 1H), 7.51 (dd, J=7.8, 7.8 Hz, 1H), 5.11 (br s, 1H), 4.31 (br s, 1H), 4.04 (t, J=7.3 Hz, 2H), 4.01-3.73 (m, 3H), 3.68 (d, J=14.6 Hz, 1H), 3.02 (d, J=4.9 Hz, 3H), 2.32 (t, J=6.3 Hz, 2H), 2.22 (s, 6H), 2.19-2.09 (m, 1H), 2.07-1.82 (m, 4H), 1.68-1.56 (m, 1H).

Example 39

(S)-6-(3-(3-(Dimethylamino)propyl)-4-oxo-3,4-dihydroquinazolin-8-yl)-2-(ethylamino)-6,7,7a,8,9,10-hexahydro-5H-pyrimido[5,4-f]pyrrolo[1,2-a][1,4]diazepin-5-one (Compound 39)

Step 1

(S)-6-(3-(3-(Dimethylamino)propyl)-4-oxo-3,4-dihydroquinazolin-8-yl)-2-(methylthio)-6,7,7a,8,9,10-hexahydro-5H-pyrimido[5,4-f]pyrrolo[1,2-a][1,4]diazepin-5-one (100 mg) obtained in step 1 of Example 38 was dissolved in dichloromethane (1.9 mL), and 4-toluenesulfonic acid monohydrate (48 mg, 0.250 mmol) was added. The mixture was sonicated until all the solid dissolved. After cooling the reaction mixture to 0° C., m-CPBA (61 mg, 0.229 mmol) was added, and the mixture was stirred at 0° C. for 15 minutes. The reaction mixture was extracted with chloroform after adding saturated sodium bicarbonate aqueous solution and saturated brine. The organic layer was dried over anhydrous sodium sulfate, and concentrated under reduced pressure to give a residue.
Step 2

A 2 mol/L ethylamine/THF solution (1.05 mL, 2.09 mmol) was added to the residue obtained in step 1, and the mixture was stirred at room temperature for 2 hours. After concentrating the reaction mixture under reduced pressure, the obtained residue was purified by silica gel column chromatography (ethyl acetate/methanol), and suspended in diethyl ether. The insoluble matter was collected by filtration, and dried under reduced pressure to give Compound 39 (28.8 mg, 3 steps 29%).

ESI-MS: m/z 477 [M+H]$^+$. $^1$H-NMR (CDCl$_3$) δ (ppm): 8.83 (s, 1H), 8.27 (t, J=4.9 Hz, 1H), 8.07 (s, 1H), 7.67 (d, J=7.8 Hz, 1H), 7.51 (dd, J=7.8, 7.8 Hz, 1H), 5.13 (br s, 1H), 4.31 (br s, 1H), 4.04 (t, J=6.8 Hz, 2H), 4.00-3.72 (m, 3H), 3.67 (d, J=14.6 Hz, 1H), 3.53-3.42 (m, 2H), 2.32 (t, J=6.8 Hz, 2H), 2.22 (s, 6H), 2.19-2.09 (m, 1H), 2.07-1.81 (m, 4H), 1.67-1.55 (m, 1H), 1.24 (t, J=7.3 Hz, 3H).

Example 40

(S)-6-(3-(2-(Dimethylamino)ethyl)-4-oxo-3,4-dihydroquinazolin-8-yl)-2-(methylamino)-6,7,7a,8,9,10-hexahydro-5H-pyrimido[5,4-f]pyrrolo[1,2-a][1,4]diazepin-5-one (Compound 40)

Compound 40 was obtained in the same manner as in Example 34, using Compound ad obtained in Reference Example 16.

ESI-MS: m/z 449 [M+H]$^+$. $^1$H-NMR (CDCl$_3$) δ (ppm): 8.82 (s, 1H), 8.28 (dd, J=7.8, 2.0 Hz, 1H), 8.04 (s, 1H), 7.67 (d, J=7.8 Hz, 1H), 7.51 (dd, J=7.8, 3.9 Hz, 1H), 5.77 (br s, 1H), 4.29 (br s, 1H), 4.05 (t, J=5.9 Hz, 2H), 4.01-3.76 (m, 2H), 3.69 (d, J=14.6 Hz, 2H), 3.02 (d, J=4.9 Hz, 3H), 2.65 (t, J=6.3 Hz, 2H), 2.29 (s, 6H), 2.21-2.10 (m, 1H), 2.08-1.98 (m, 1H), 1.97-1.84 (m, 1H), 1.71-1.55 (m, 1H).

Example 41

(S)-6-(3-(2-(Dimethylamino)ethyl)-4-oxo-3,4-dihydroquinazolin-8-yl)-2-(ethylamino)-6,7,7a,8,9,10-hexahydro-5H-pyrimido[5,4-f]pyrrolo[1,2-a][1,4]diazepin-5-one (Compound 41)

Compound 41 was obtained in the same manner as in steps 1 and 2 of Example 34, and Example 35, using Compound ad obtained in Reference Example 16.

ESI-MS: m/z 463 [M+H]$^+$. $^1$H-NMR (CDCl$_3$) δ (ppm): 8.80 (s, 1H), 8.28 (d, J=6.8 Hz, 1H), 8.04 (s, 1H), 7.66 (d, J=7.8 Hz, 1H), 7.51 (dd, J=7.8, 7.8 Hz, 1H), 6.25 (br s, 1H), 4.31 (br s, 1H), 4.06 (t, J=6.3 Hz, 2H), 4.00-3.73 (m, 3H), 3.68 (d, J=14.6 Hz, 1H), 3.56-3.42 (m, 2H), 2.67 (t, J=6.3 Hz, 2H), 2.32-2.29 (m, 1H), 2.30 (s, 1H), 2.21-2.09 (m, 1H), 2.09-1.98 (m, 3H), 1.98-1.82 (m, 3H), 1.71-1.53 (m, 1H), 1.26 (t, J=6.8 Hz, 3H).

Example 42

(S)-6-(3-(2-Hydroxy-2-methylpropyl)-4-oxo-3,4-dihydroquinazolin-8-yl)-2-(methylamino)-6,7,7a,8,9,10-hexahydro-5H-pyrimido[5,4-f]pyrrolo[1,2-a][1,4]diazepin-5-one (Compound 42)

Compound 42 was obtained in the same manner as in Example 34, using Compound ae obtained in Reference Example 17.

ESI-MS: m/z 450 [M+H]$^+$. $^1$H-NMR (CDCl$_3$) δ (ppm): 8.82 (s, 1H), 8.28 (dd, J=7.8, 2.0 Hz, 1H), 8.12 (s, 1H), 7.69 (d, J=7.8 Hz, 1H), 7.53 (dd, J=7.8, 7.8 Hz, 1H), 5.12 (br s, 1H), 4.30 (br s, 1H), 4.03 (s, 2H), 4.00-3.75 (m, 3H), 3.70 (d, J=14.6 Hz, 1H), 3.02 (d, J=4.9 Hz, 3H), 2.63 (br s, 1H), 2.20-2.10 (m, 1H), 2.08-1.98 (m, 1H), 1.97-1.82 (m, 1H), 1.67-1.55 (m, 1H), 1.30 (s, 3H), 1.29 (s, 3H).

Example 43

(S)-2-(Ethylamino)-6-(3-(2-hydroxy-2-methylpropyl)-4-oxo-3,4-dihydroquinazolin-8-yl)-6,7,7a,8,9,10-hexahydro-5H-pyrimido[5,4-f]pyrrolo[1,2-a][1,4]diazepin-5-one (Compound 43)

Compound 43 was obtained in the same manner as in steps 1 and 2 of Example 34, and Example 35, using Compound ae obtained in Reference Example 17.

ESI-MS: m/z 464 [M+H]$^+$. $^1$H-NMR (CDCl$_3$) δ (ppm): 8.82 (s, 1H), 8.30-8.26 (m, 1H), 8.12 (s, 1H), 7.68 (d, J=7.8 Hz, 1H), 7.52 (dd, J=7.8, 7.8 Hz, 1H), 5.14 (br s, 1H), 4.30 (br s, 1H), 4.03 (s, 2H), 4.01-3.74 (m, 3H), 3.69 (d, J=14.6 Hz, 1H), 3.54-3.41 (m, 2H), 2.62 (s, 1H), 2.22-2.10 (m, 1H), 2.10-1.97 (m, 1H), 1.97-1.83 (m, 1H), 1.71-1.55 (m, 1H), 1.30 (s, 3H), 1.29 (s, 3H), 1.24 (t, J=6.8 Hz, 3H).

Example 44

(S)-2-Amino-6-(3-methyl-4-oxo-3,4-dihydroquinazolin-8-yl)-6,7,7a,8,9,10-hexahydro-5H-pyrimido[5,4-f]pyrrolo[1,2-a][1,4]diazepin-5-one (Compound 44)

(S)-6-(3-Methyl-4-oxo-3,4-dihydroquinazolin-8-yl)-2-methylthio-6,7,7a,8,9,10-hexahydro-5H-pyrimido[5,4-f]pyrrolo[1,2-a][1,4]diazepin-5-one (1.58 g, 3.87 mmol) obtained in step 1 of Example 9 was dissolved in dichloromethane (20 mL), and m-CPBA (1.00 g, 5.80 mmol) was added. The mixture was stirred at room temperature for 0.5 hours. The reaction mixture was diluted by adding chloroform, and washed with a sodium thiosulfate aqueous solution and a saturated sodium bicarbonate aqueous solution. The organic layer was dried over anhydrous magnesium sulfate, and concentrated under reduced pressure. The obtained residue was suspended in THF (19 mL), and 25% ammonia water (3.35 mL, 38.7 mmol) was added. The mixture was stirred at room temperature for 19 hours. After concentrating the reaction mixture under reduced pressure, the obtained residue was purified by silica gel column chromatography (chloroform/methanol=15/1), and reslurried in acetonitrile to give Compound 44 (0.680 g, 47%).

ESI-MS: m/z 378 [M+H]$^+$. $^1$H-NMR (CDCl$_3$) δ: 1.62 (m, 1H), 1.89 (m, 1H), 2.03 (m, 1H), 2.14 (m, 1H), 3.58 (s, 3H), 3.65-3.99 (m, 4H), 4.32 (m, 1H), 5.01 (br s, 2H), 7.53 (dd, J=7.7, 8.1 Hz, 1H), 7.67 (dd, J=1.5, 7.7 Hz, 1H), 8.02 (s, 1H), 8.30 (dd, J=1.5, 8.1 Hz, 1H), 8.84 (s, 1H).

Example 45

(S)-6-(3-Cyclopropyl-4-oxo-3,4-dihydroquinazolin-8-yl)-2-ethylamino-6,7,7a,8,9,10-hexahydro-5H-pyrimido[5,4-f]pyrrolo[1,2-a][1,4]diazepin-5-one (Compound 45)

Compound 45 was obtained in the same manner as in steps 1 and 2 of Example 34, and Example 35, using Compound of in Reference Example 18.

ESI-MS: m/z 432 [M+H]⁺. ¹H-NMR (CDCl₃) δ (ppm): 0.91 (m, 2H), 1.19 (m, 2H), 1.25 (t, J=7.3 Hz, 3H), 1.63 (m, 1H), 1.89 (m, 1H), 2.01 (m, 1H), 2.12 (m, 1H), 3.22 (m, 1H), 3.43-3.52 (m, 2H), 3.63-3.99 (m, 4H), 4.29 (m, 1H), 5.11 (br s, 1H), 7.52 (dd, J=7.7, 7.7 Hz, 1H), 7.65 (dd, J=1.5, 7.7 Hz, 1H), 8.08 (s, 1H), 8.28 (dd, J=1.5, 7.7 Hz, 1H), 8.82 (s, 1H).

Example 46

(S)-6-(3-Cyclopropyl-4-oxo-3,4-dihydroquinazolin-8-yl)-2-methylamino-6,7,7a,8,9,10-hexahydro-5H-pyrimido[5,4-f]pyrrolo[1,2-a][1,4]diazepin-5-one (Compound 46)

Compound 46 was obtained in the same manner as in Example 34, using Compound of in Reference Example 18.
ESI-MS: m/z 418 [M+H]⁺. ¹H-NMR (CDCl₃) δ (ppm): 0.91 (m, 2H), 1.19 (m, 2H), 1.61 (m, 1H), 1.89 (m, 1H), 2.01 (m, 1H), 2.13 (m, 1H), 3.02 (d, J=4.8 Hz, 2H), 3.22 (m, 1H), 3.63-3.97 (m, 4H), 4.28 (m, 1H), 5.14 (br s, 1H), 7.52 (dd, J=7.7, 7.7 Hz, 1H), 7.65 (dd, J=1.5, 7.7 Hz, 1H), 8.08 (s, 1H), 8.28 (dd, J=1.5, 7.7 Hz, 1H), 8.83 (s, 1H).

Example 47

(S)-2-Ethylamino-6-(3-(2-fluoroethyl)-4-oxo-3,4-dihydroquinazolin-8-yl)-6,7,7a,8,9,10-hexahydro-5H-pyrimido[5,4-f]pyrrolo[1,2-a][1,4]diazepin-5-one (Compound 47)

Compound 47 was obtained in the same manner as in steps 1 and 2 of Example 34, and Example 35, using Compound ag in Reference Example 19.
ESI-MS: m/z 438 [M+H]⁺. ¹H-NMR (CDCl₃) δ (ppm): 1.25 (t, J=7.8 Hz, 3H), 1.64 (m, 1H), 1.89 (m, 1H), 2.02 (m, 1H), 2.14 (m, 1H), 3.44-3.51 (m, 2H), 3.67-3.98 (m, 4H), 4.22-4.37 (m, 3H), 4.74 (dt, J=3.9, 46.8 Hz, 2H), 5.13 (br s, 1H), 7.54 (dd, J=7.8, 7.8 Hz, 1H), 7.70 (dd, J=1.9, 7.8 Hz, 1H), 8.03 (s, 1H), 8.28 (dd, J=1.9, 7.8 Hz, 1H), 8.83 (s, 1H).

Example 48

(S)-6-(3-(2-Fluoroethyl)-4-oxo-3,4-dihydroquinazolin-8-yl)-2-methylamino-6,7,7a,8,9,10-hexahydro-5H-pyrimido[5,4-f]pyrrolo[1,2-a][1,4]diazepin-5-one (Compound 48)

Compound 48 was obtained in the same manner as in Example 34, using Compound ag in Reference Example 19.
ESI-MS: m/z 424 [M+H]⁺.

Example 49

(S)-2-Amino-6-(3-(2-fluoroethyl)-4-oxo-3,4-dihydroquinazolin-8-yl)-6,7,7a,8,9,10-hexahydro-5H-pyrimido[5,4-f]pyrrolo[1,2-a][1,4]diazepin-5-one (Compound 49)

Compound 49 was obtained in the same manner as in step of Example 34, and Example 44, using Compound ag in Reference Example 19.
ESI-MS: m/z 410 [M+H]⁺. ¹H-NMR (CDCl₃) δ (ppm): 1.64 (m, 1H), 1.90 (m, 1H), 2.03 (m, 1H), 2.16 (m, 1H), 3.67-3.98 (m, 4H), 4.22-4.38 (m, 3H), 4.74 (dq, J=4.8, 46.8 Hz, 2H), 4.99 (br s, 1H), 7.54 (dd, J=7.8, 7.8 Hz, 1H), 7.70 (dd, J=1.9, 7.8 Hz, 1H), 8.03 (s, 1H), 8.29 (dd, J=1.9, 7.8 Hz, 1H), 8.84 (s, 1H).

Example 50

(S)-6-(3-(2,2-Difluoroethyl)-4-oxo-3,4-dihydroquinazolin-8-yl)-2-ethylamino-6,7,7a,8,9,10-hexahydro-5H-pyrimido[5,4-f]pyrrolo[1,2-a][1,4]diazepin-5-one (Compound 50)

Compound 50 was obtained in the same manner as in steps 1 and 2 of Example 34, and Example 35, using Compound ah in Reference Example 20.
ESI-MS: m/z 456 [M+H]⁺. ¹H-NMR (CDCl₃) δ (ppm): 1.25 (t, J=6.8 Hz, 3H), 1.63 (m, 1H), 1.89 (m, 1H), 2.03 (m, 1H), 2.14 (m, 1H), 3.44-3.52 (m, 2H), 3.66-3.99 (m, 4H), 4.23-4.38 (m, 3H), 5.13 (br s, 1H), 6.14 (dt, J=4.9, 56.6 Hz, 1H), 7.57 (dd, J=7.8, 7.8 Hz, 1H), 7.72 (dd, J=1.9, 7.8 Hz, 1H), 7.99 (s, 1H), 8.28 (dd, J=1.9, 7.8 Hz, 1H), 8.82 (s, 1H).

Example 51

(S)-6-(3-(2,2-Difluoroethyl)-4-oxo-3,4-dihydroquinazolin-8-yl)-2-methylamino-6,7,7a,8,9,10-hexahydro-5H-pyrimido[5,4-f]pyrrolo[1,2-a][1,4]diazepin-5-one (Compound 51)

Compound 51 was obtained in the same manner as in Example 34, using Compound ah in Reference Example 20.
ESI-MS: m/z 442 [M+H]⁺. ¹H-NMR (CDCl₃) δ (ppm): 1.64 (m, 1H), 1.91 (m, 1H), 2.03 (m, 1H), 2.15 (m, 1H), 3.02 (d, J=4.9 Hz, 3H), 3.66-3.98 (m, 4H), 4.21-4.38 (m, 3H), 5.15 (br s, 1H), 6.14 (dt, J=3.9, 55.6 Hz, 1H), 7.57 (dd, J=7.8, 7.8 Hz, 1H), 7.72 (dd, J=1.3, 7.8 Hz, 1H), 7.98 (s, 1H), 8.28 (dd, J=1.3, 7.8 Hz, 1H), 8.83 (s, 1H).

Example 52

(S)-2-Ethylamino-6-(4-oxo-3-(2,2,2-difluoroethyl)-3,4-dihydroquinazolin-8-yl)-6,7,7a,8,9,10-hexahydro-5H-pyrimido[5,4-f]pyrrolo[1,2-a][1,4]diazepin-5-one (Compound 52)

Compound 52 was obtained in the same manner as in steps 1 and 2 of Example 34, and Example 35, using Compound ai in Reference Example 21.
ESI-MS: m/z 474 [M+H]⁺. ¹H-NMR (CDCl₃) δ (ppm): 1.25 (t, J=6.8 Hz, 3H), 1.62 (m, 1H), 1.91 (m, 1H), 2.03 (m, 1H), 2.16 (m, 1H), 3.44-3.51 (m, 2H), 3.66-3.99 (m, 4H), 4.26 (m, 1H), 4.52-4.76 (m, 2H), 5.12 (br s, 1H), 7.58 (dd, J=7.8, 7.8 Hz, 1H), 7.72 (dd, J=1.9, 7.8 Hz, 1H), 8.00 (s, 1H), 8.28 (dd, J=1.9, 7.8 Hz, 1H), 8.82 (s, 1H).

Example 53

(S)-2-Methylamino-6-(4-oxo-3-(2,2,2-trifluoroethyl)-3,4-dihydroquinazolin-8-yl)-6,7,7a,8,9,10-hexahydro-5H-pyrimido[5,4-f]pyrrolo[1,2-a][1,4]diazepin-5-one (Compound 53)

Compound 53 was obtained in the same manner as in steps 1 and 2 of Example 34, and Example 35, using Compound ai in Reference Example 21.
ESI-MS: m/z 460 [M+H]⁺. ¹H-NMR (CDCl₃) δ (ppm): 1.66 (m, 1H), 1.92 (m, 1H), 2.04 (m, 1H), 2.16 (m, 1H), 3.02 (d, J=4.9 Hz, 3H), 3.67-4.00 (m, 4H), 4.28 (m, 1H), 4.52-4.77 (m, 2H), 5.14 (br s, 1H), 7.58 (dd, J=7.8, 7.8 Hz, 1H), 7.72 (dd, J=1.5, 7.8 Hz, 1H), 8.00 (s, 1H), 8.30 (dd, J=1.5, 7.8 Hz, 1H), 8.83 (s, 1H).

Example 54

(S)-6-(3-Ethyl-4-oxo-2-trifluoromethyl-3,4-dihydroquinazolin-8-yl)-2-ethylamino-6,7,7a,8,9,10-hexahydro-5H-pyrimido[5,4-f]pyrrolo[1,2-a][1,4]diazepin-5-one (Compound 54)

Compound 54 was obtained in the same manner as in steps 1 and 2 of Example 34, and Example 35, using Compound aj in Reference Example 22.
ESI-MS: m/z 488 [M+H]$^+$. $^1$H-NMR (CDCl$_3$) δ (ppm): 1.25 (t, J=7.3 Hz, 3H), 1.40 (t, J=7.0 Hz, 3H), 1.64 (m, 1H), 1.90 (m, 1H), 2.02 (m, 1H), 2.17 (m, 1H), 3.43-3.54 (m, 2H), 3.65-3.94 (m, 4H), 4.19-4.53 (m, 3H), 5.13 (br s, 1H), 7.63 (dd, J=7.7, 7.7 Hz, 1H), 7.78 (dd, J=1.5, 7.7 Hz, 1H), 8.29 (dd, J=1.5, 7.7 Hz, 1H), 8.83 (s, 1H).

Example 55

(S)-6-(3-Ethyl-4-oxo-2-trifluoromethyl-3,4-dihydroquinazolin-8-yl)-2-methylamino-6,7,7a,8,9,10-hexahydro-5H-pyrimido[5,4-f]pyrrolo[1,2-a][1,4]diazepin-5-one (Compound 55)

Compound 55 was obtained in the same manner as in Example 34, using Compound aj in Reference Example 22.
ESI-MS: m/z 474 [M+H]$^+$. $^1$H-NMR (CDCl$_3$) δ (ppm): 1.40 (t, J=7.0 Hz, 3H), 1.65 (m, 1H), 1.90 (m, 1H), 2.02 (m, 1H), 2.17 (m, 1H), 3.03 (d, J=4.8 Hz, 3H), 3.65-3.94 (m, 4H), 4.23 (q, J=7.0 Hz, 2H), 4.48 (m, 1H), 5.11 (br s, 1H), 7.63 (dd, J=7.7, 8.1 Hz, 1H), 7.79 (dd, J=1.5, 7.7 Hz, 1H), 8.29 (dd, J=1.5, 8.17 Hz, 1H), 8.84 (s, 1H).

Example 56

(S)-2-Ethylamino-6-(3-methyl-4-oxo-2-trifluoromethyl-3,4-dihydroquinazolin-8-yl)-6,7,7a,8,9,10-hexahydro-5H-pyrimido[5,4-f]pyrrolo[1,2-a][1,4]diazepin-5-one (Compound 56)

Compound 56 was obtained in the same manner as in steps 1 and 2 of Example 34, and Example 35, using Compound ak in Reference Example 23.
ESI-MS: m/z 474 [M+H]$^+$. $^1$H-NMR (CDCl$_3$) δ (ppm): 1.25 (t, J=6.8 Hz, 3H), 1.62 (m, 1H), 1.91 (m, 1H), 2.03 (m, 1H), 2.17 (m, 1H), 3.45-3.52 (m, 2H), 3.66-3.94 (m, 4H), 3.73 (s, 3H), 4.52 (m, 1H), 5.16 (br s, 1H), 7.64 (dd, J=7.8, 7.8 Hz, 1H), 7.79 (dd, J=1.9, 7.8 Hz, 1H), 8.29 (dd, J=1.5, 7.8 Hz, 1H), 8.83 (s, 1H).

Example 57

(S)-6-(3-Methyl-4-oxo-2-trifluoromethyl-3,4-dihydroquinazolin-8-yl)-2-methylamino-6,7,7a,8,9,10-hexahydro-5H-pyrimido[5,4-f]pyrrolo[1,2-a][1,4]diazepin-5-one (Compound 57)

Compound 57 was obtained in the same manner as in Example 34, using Compound ak in Reference Example 23.
ESI-MS: m/z 460 [M+H]$^+$. $^1$H-NMR (CDCl$_3$) δ (ppm): 1.65 (m, 1H), 1.91 (m, 1H), 2.03 (m, 1H), 2.18 (m, 1H), 3.03 (d, J=4.9 Hz, 3H), 3.65-3.95 (m, 4H), 3.73 (s, 3H), 4.50 (m, 1H), 5.15 (br s, 1H), 7.64 (dd, J=7.8, 7.8 Hz, 1H), 7.79 (dd, J=1.9, 7.8 Hz, 1H), 8.29 (dd, J=1.9, 7.8 Hz, 1H), 8.82 (s, 1H).

Example 58

(S)-2-Amino-6-(3-methyl-4-oxo-2-trifluoromethyl-3,4-dihydroquinazolin-8-yl)-6,7,7a,8,9,10-hexahydro-5H-pyrimido[5,4-f]pyrrolo[1,2-a][1,4]diazepin-5-one (Compound 58)

Compound 58 was obtained in the same manner as in step of Example 34, and Example 44, using Compound ak in Reference Example 23.
ESI-MS: m/z 446 [M+H]$^+$. $^1$H-NMR (CDCl$_3$) δ (ppm): 1.64 (m, 1H), 1.90 (m, 1H), 2.03 (m, 1H), 2.18 (m, 1H), 3.66-3.91 (m, 4H), 3.73 (s, 3H), 4.50 (m, 1H), 5.00 (br s, 2H), 7.64 (dd, J=7.8, 7.8 Hz, 1H), 7.79 (dd, J=1.9, 7.8 Hz, 1H), 8.30 (dd, J=1.9, 7.8 Hz, 1H), 8.84 (s, 1H).

Example 59

(S)-2-Ethylamino-6-(3-(2-fluoroethyl)-2-methyl-4-oxo-3,4-dihydroquinazolin-8-yl)-6,7,7a,8,9,10-hexahydro-5H-pyrimido[5,4-f]pyrrolo[1,2-a][1,4]diazepin-5-one (Compound 59)

Compound 59 was obtained in the same manner as in steps 1 and 2 of Example 34, and Example 35, using Compound al in Reference Example 24.
ESI-MS: m/z 452 [M+H]$^+$. $^1$H-NMR (CDCl$_3$) δ (ppm): 1.25 (t, J=7.8 Hz, 3H), 1.63 (m, 1H), 1.91 (m, 1H), 2.04 (m, 1H), 2.16 (m, 1H), 2.62 (s, 3H), 3.45-3.52 (m, 2H), 3.66-3.96 (m, 4H), 4.31-4.48 (m, 3H), 4.77 (dq, J=4.9, 47.8 Hz, 2H), 5.10 (br s, 1H), 7.46 (dd, J=7.8, 7.8 Hz, 1H), 7.67 (dd, J=1.9, 7.8 Hz, 1H), 8.20 (dd, J=1.9, 7.8 Hz, 1H), 8.84 (s, 1H).

Example 60

(S)-6-(3-(2-Fluoroethyl-2-methyl-4-oxo-3,4-dihydroquinazolin-8-yl)-2-methylamino-6,7,7a,8,9,10-hexahydro-5H-pyrimido[5,4-f]pyrrolo[1,2-a][1,4]diazepin-5-one (Compound 60)

Compound 60 was obtained in the same manner as in Example 34, using Compound al in Reference Example 24.
ESI-MS: m/z 438 [M+H]$^+$. $^1$H-NMR (CDCl$_3$) δ (ppm): 1.65 (m, 1H), 1.90 (m, 1H), 2.05 (m, 1H), 2.17 (m, 1H), 2.62 (s, 3H), 3.03 (d, J=4.9 Hz, 3H), 3.65-3.95 (m, 4H), 4.35-4.46 (m, 3H), 4.78 (dq, J=4.9, 47.8 Hz, 2H), 5.10 (br s, 1H), 7.46 (dd, J=7.8, 7.8 Hz, 1H), 7.67 (dd, J=1.9, 7.8 Hz, 1H), 8.21 (dd, J=1.9, 7.8 Hz, 1H), 8.85 (s, 1H).

Example 61

(S)-6-(3-(2,2-Difluoroethyl)-2-methyl-4-oxo-3,4-dihydroquinazolin-8-yl)-2-methylamino-6,7,7a,8,9,10-hexahydro-5H-pyrimido[5,4-f]pyrrolo[1,2-a][1,4]diazepin-5-one (Compound 61)

Compound 61 was obtained in the same manner as in Example 34, using Compound am in Reference Example 25.
ESI-MS: m/z 456 [M+H]$^+$. $^1$H-NMR (CDCl$_3$) δ (ppm): 1.65 (m, 1H), 1.91 (m, 1H), 2.05 (m, 1H), 2.16 (m, 1H), 2.62 (s, 3H), 3.02 (d, J=4.9 Hz, 3H), 3.64-3.98 (m, 4H), 4.35-4.46 (m, 3H), 5.11 (br s, 1H), 6.18 (dq, J=4.8, 56.6 Hz, 1H), 7.49 (dd, J=7.8, 7.8 Hz, 1H), 7.69 (dd, J=1.9, 7.8 Hz, 1H), 8.20 (dd, J=1.9, 7.8 Hz, 1H), 8.84 (s, 1H).

Example 62

(S)-2-Ethylamino-6-(3-(2-hydroxyethyl)-4-oxo-3,4-dihydroquinazolin-8-yl)-6,7,7a,8,9,10-hexahydro-5H-pyrimido[5,4-f]pyrrolo[1,2-a][1,4]diazepin-5-one (Compound 62)

Step 1

(S)-6-(3-(2-tert-Butyldimethylsiloxyethyl)-4-oxo-3,4-dihydroquinazolin-8-yl)-2-methylthio-6,7,7a,8,9,10-hexahydro-5H-pyrimido[5,4-f]pyrrolo[1,2-a][1,4]diazepin-5-one (0.423 g, 53%) was obtained in the same manner as in step 1 of Example 34, using Compound an in Reference Example 26.

ESI-MS: m/z 553 [M+H]$^+$. $^1$H-NMR (CDCl$_3$) δ: 0.06 (s, 6H), 0.90 (s, 9H), 1.69 (m, 1H), 1.99 (m, 1H), 2.14 (m, 1H), 2.22 (m, 1H), 2.63 (s, 3H), 3.74-4.10 (m, 8H), 4.29 (m, 1H), 7.59 (dd, J=7.8, 7.8 Hz, 1H), 7.76 (dd, J=1.0, 7.8 Hz, 1H), 8.11 (s, 1H), 8.37 (dd, J=1.0, 7.8 Hz, 1H), 8.95 (s, 1H).

Step 2

(S)-6-(3-(2-tert-Butyldimethylsiloxyethyl)-4-oxo-3,4-dihydroquinazolin-8-yl)-2-methylthio-6,7,7a,8,9,10-hexahydro-5H-pyrimido[5,4-f]pyrrolo[1,2-a][1,4]diazepin-5-one (0.423 g, 0.765 mmol) obtained in step 1 was dissolved in THF (3.8 mL), and a 1.0 mol/L tetrabutylammonium fluoride/THF solution (1.53 mL, 1.53 mmol) was added. The mixture was stirred at room temperature for 2 hours. After concentrating the reaction mixture under reduced pressure, the obtained residue was purified by silica gel column chromatography (chloroform/methanol=20/1) to give (S)-6-(3-(2-hydroxyethyl)-4-oxo-3,4-dihydroquinazolin-8-yl)-2-methylthio-6,7,7a,8,9,10-hexahydro-5H-pyrimido[5,4-f]pyrrolo[1,2-a][1,4]diazepin-5-one (0.336 g, quantitative).

ESI-MS: m/z 439 [M+H]$^+$. $^1$H-NMR (CDCl$_3$) δ: 1.63 (m, 1H), 1.93 (m, 1H), 2.05 (m, 1H), 2.18 (m, 1H), 2.44 (br s, 1H), 2.54 (s, 3H), 3.69-4.12 (m, 8H), 4.36 (m, 1H), 7.50 (dd, J=7.8, 7.8 Hz, 1H), 7.63 (dd, J=1.9, 7.8 Hz, 1H), 8.04 (s, 1H), 8.26 (dd, J=1.9, 7.8 Hz, 1H), 8.79 (s, 1H).

Step 3

Compound 62 was obtained in the same manner as in step of Example 34, and Example 35, using (S)-6-(3-(2-hydroxyethyl)-4-oxo-3,4-dihydroquinazolin-8-yl)-2-methylthio-6,7,7a,8,9,10-hexahydro-5H-pyrimido[5,4-f]pyrrolo[1,2-a][1,4]diazepin-5-one obtained in step 2.

Example 63

(S)-6-(3-(2-Hydroxyethyl)-4-oxo-3,4-dihydroquinazolin-8-yl)-2-methylamino-6,7,7a,8,9,10-hexahydro-5H-pyrimido[5,4-f]pyrrolo[1,2-a][1,4]diazepin-5-one (Compound 63)

Compound 63 was obtained in the same manner as in steps 2 and 3 of Example 34, using (S)-6-(3-(2-hydroxyethyl)-4-oxo-3,4-dihydroquinazolin-8-yl)-2-methylthio-6,7,7a,8,9,10-hexahydro-5H-pyrimido[5,4-f]pyrrolo[1,2-a][1,4]diazepin-5-one (0.110 g, 0.250 mmol) obtained in step 2 of Example 62.

ESI-MS: m/z 422 [M+H]$^+$. $^1$H-NMR (CDCl$_3$) δ (ppm): 1.64 (m, 1H), 1.90 (m, 1H), 2.03 (m, 1H), 2.14 (m, 1H), 3.02 (d, J=4.9 Hz, 3H), 3.66-3.99 (m, 6H), 4.10-4.17 (m, 2H), 4.30 (m, 1H), 5.10 (br s, 1H), 7.53 (dd, J=7.8, 7.8 Hz, 1H), 7.67 (dd, J=1.0, 7.8 Hz, 1H), 8.06 (s, 1H), 8.28 (dd, J=1.0, 7.8 Hz, 1H), 8.82 (s, 1H).

Example 64

(S)-2-Amino-6-(3-(2-hydroxyethyl)-4-oxo-3,4-dihydroquinazolin-8-yl)-6,7,7a,8,9,10-hexahydro-5H-pyrimido[5,4-f]pyrrolo[1,2-a][1,4]diazepin-5-one (Compound 64)

Compound 64 was obtained in the same manner as in Example 44, using (S)-6-(3-(2-hydroxyethyl)-4-oxo-3,4-dihydroquinazolin-8-yl)-2-methylthio-6,7,7a,8,9,10-hexahydro-5H-pyrimido[5,4-f]pyrrolo[1,2-a][1,4]diazepin-5-one (0.110 g, 0.250 mmol) obtained in step 2 of Example 62.

ESI-MS: m/z 408 [M+H]$^+$. $^1$H-NMR (CDCl$_3$) δ (ppm): 1.64 (m, 1H), 1.91 (m, 1H), 2.05 (m, 1H), 2.17 (m, 1H), 3.24-3.42 (m, 5H), 3.68-3.99 (m, 7H), 7.55 (dd, J=7.8, 7.8 Hz, 1H), 7.66 (dd, J=1.0, 7.8 Hz, 1H), 8.11 (s, 1H), 8.31 (dd, J=1.0, 7.8 Hz, 1H), 8.71 (s, 1H).

Example 65

(S)-2-Ethylamino-6-(2-(methoxymethyl)-3-methyl-4-oxo-3,4-dihydroquinazolin-8-yl)-6,7,7a,8,9,10-hexahydro-5H-pyrimido[5,4-f]pyrrolo[1,2-a][1,4]diazepin-5-one (Compound 65)

Compound 65 was obtained in the same manner as in steps 1 and 2 of Example 34, and Example 35, using Compound ao in Reference Example 27.

ESI-MS: m/z 450 [M+H]$^+$. $^1$H-NMR (CDCl$_3$) δ (ppm): 1.25 (t, J=7.8 Hz, 3H), 1.64 (m, 1H), 1.88 (m, 1H), 2.02 (m, 1H), 2.15 (m, 1H), 3.42 (s, 3H), 3.44-3.51 (m, 2H), 3.66 (s, 3H), 3.66-3.98 (m, 4H), 4.43-4.56 (m, 3H), 5.38 (br s, 1H), 7.50 (dd, J=7.8, 7.8 Hz, 1H), 7.67 (dd, J=1.0, 7.8 Hz, 1H), 8.24 (dd, J=1.0, 7.8 Hz, 1H), 8.81 (s, 1H).

Example 66

(S)-6-(2-(Methoxymethyl)-3-methyl-4-oxo-3,4-dihydroquinazolin-8-yl)-2-methylamino-6,7,7a,8,9,10-hexahydro-5H-pyrimido[5,4-f]pyrrolo[1,2-a][1,4]diazepin-5-one (Compound 66)

Compound 66 was obtained in the same manner as in Example 34, using Compound ao in Reference Example 27.

ESI-MS: m/z 436 [M+H]$^+$. $^1$H-NMR (CDCl$_3$) δ (ppm): 1.63 (m, 1H), 1.89 (m, 1H), 2.05 (m, 1H), 2.15 (m, 1H), 3.02 (d, J=4.8 Hz, 3H), 3.42 (s, 3H), 3.66-3.96 (m, 4H), 3.67 (s, 3H), 4.42-4.56 (m, 3H), 5.29 (br s, 1H), 7.51 (dd, J=7.8, 7.8 Hz, 1H), 7.68 (dd, J=1.0, 7.8 Hz, 1H), 8.25 (dd, J=1.0, 7.8 Hz, 1H), 8.82 (s, 1H).

Example 67

(S)-2-Ethylamino-6-(3-methyl-4-oxo-3,4-dihydropyrido[4,3-d]pyrimidin-8-yl)-6,7,7a,8,9,10-hexahydro-5H-pyrimido[5,4-f]pyrrolo[1,2-a][1,4]diazepin-5-one (Compound 67)

Compound 67 was obtained in the same manner as in steps 1 and 2 of Example 34, and Example 35, using Compound ap in Reference Example 28.

ESI-MS: m/z 407 [M+H]$^+$. $^1$H-NMR (DMSO-d$_6$) δ (ppm): 1.15 (t, J=6.6 Hz, 3H), 1.60 (m, 1H), 1.78 (m, 1H), 1.94 (m, 1H), 2.09 (m, 1H), 3.31-3.36 (m, 2H), 3.52 (s, 3H), 3.65-3.77 (m, 3H), 3.85 (dd, J=7.3, 14.7 Hz, 1H), 4.11-4.22 (m, 1H), 7.25 (br s, 1H), 8.49 (s, 1H), 8.58 (s, 1H), 8.77 (s, 1H), 9.26 (s, 1H).

Example 68

(S)-6-(3-Methyl-4-oxo-3,4-dihydropyrido[4,3-d]
pyrimidin-8-yl)-2-methylthio-6,7,7a,8,9,10-hexa-
hydro-5H-pyrimido[5,4-f]pyrrolo[1,2-a][1,4]diaz-
epin-5-one (Compound 68)

Compound 68 was obtained in the same manner as in
Example 34, using Compound ap in Reference Example 28.
ESI-MS: m/z 393 [M+H]$^+$. $^1$H-NMR (DMSO-d$_6$) δ
(ppm): 1.59 (m, 1H), 1.79 (m, 1H), 1.94 (m, 1H), 2.09 (m,
1H), 2.84 (d, J=4.4 Hz, 3H), 3.52 (s, 3H), 3.68-3.78 (m, 3H),
3.85 (dd, J=7.3, 15.0 Hz, 1H), 4.12-4.22 (m, 1H), 7.15 (brs,
1H), 8.48 (s, 1H), 8.58 (s, 1H), 8.77 (s, 1H), 9.26 (s, 1H).

Example 69

(S)-2-(2-Fluoroethylamino)-6-(3-methyl-4-oxo-3,4-
dihydroquinazolin-8-yl)-6,7,7a,8,9,10-hexahydro-
5H-pyrimido[5,4-f]pyrrolo[1,2-a][1,4]diazepin-5-
one (Compound 69)

Compound 69 was obtained in the same manner as in
steps 2 and 3 of Example 34, using (S)-6-(2,3-dimethyl-4-
oxo-4H-pyrido[1,2-a]pyrimidin-9-yl)-2-methylthio-6,7,7a,
8,9,10-hexahydro-5H-pyrimido[5,4-f]pyrrolo[1,2-a][1,4]di-
azepin-5-one obtained in step 1 of Example 9, and
2-fluoroethylamine monohydrochloride.
ESI-MS: m/z 424 [M+H]$^+$. $^1$H-NMR (CDCl$_3$) δ (ppm):
1.45-2.26 (m, 4H), 3.57 (s, 3H), 3.60-4.00 (m, 6H), 4.21-
4.42 (m, 1H), 4.50-4.71 (m, 2H), 5.46 (br s, 1H), 7.53 (dd,
J=8.1, 7.7 Hz, 1H), 7.67 (dd, J=7.7, 1.5 Hz, 1H), 8.02 (s,
1H), 8.29 (dd, J=8.1, 1.5 Hz, 1H), 8.83 (s, 1H).

Example 70

(S)-2-(2,2-Difluoroethylamino)-6-(3-methyl-4-oxo-
3,4-dihydroquinazolin-8-yl)-6,7,7a,8,9,10-hexa-
hydro-5H-pyrimido[5,4-f]pyrrolo[1,2-a][1,4]diaz-
epin-5-one (Compound 70)

Compound 70 was obtained in the same manner as in
steps 2 and 3 of Example 34, using (S)-6-(2,3-dimethyl-4-
oxo-4H-pyrido[1,2-a]pyrimidin-9-yl)-2-methylthio-6,7,7a,
8,9,10-hexahydro-5H-pyrimido[5,4-f]pyrrolo[1,2-a][1,4]di-
azepin-5-one obtained in step 1 of Example 9, and 2,2-
difluoroethylamine.
ESI-MS: m/z 442 [M+H]$^+$. $^1$H-NMR (CDCl$_3$) δ (ppm):
1.51-2.27 (m, 4H), 3.51-4.00 (m, 9H), 4.16-4.50 (m, 1H),
5.43 (br s, 1H), 5.77-6.22 (m, 1H), 7.54 (dd, J=8.1, 7.7 Hz,
1H), 7.67 (dd, J=7.7, 1.5 Hz, 1H), 8.02 (s, 1H), 8.30 (dd,
J=8.1, 1.5 Hz, 1H), 8.83 (s, 1H).

Example 71

(S)-6-(3-Methyl-4-oxo-3,4-dihydroquinazolin-8-yl)-
2-propylamino-6,7,7a,8,9,10-hexahydro-5H-py-
rimido[5,4-f]pyrrolo[1,2-a][1,4]diazepin-5-one
(Compound 71)

Compound 71 was obtained in the same manner as in
steps 2 and 3 of Example 34, using (S)-6-(3-methyl-4-oxo-
3,4-dihydroquinazolin-8-yl)-2-methylthio-6,7,7a,8,9,10-
hexahydro-5H-pyrimido[5,4-f]pyrrolo[1,2-a][1,4]diazepin-
5-one obtained in step 1 of Example 9, and 1-propylamine.
ESI-MS: m/z 420 [M+H]$^+$. $^1$H-NMR (CDCl$_3$) δ (ppm):
0.98 (t, J=7.3 Hz, 3H), 1.55-1.75 (m, 3H), 1.81-1.96 (m,
1H), 1.97-2.08 (m, 1H), 2.08-2.18 (m, 1H), 3.35-3.47 (m,
2H), 3.52-4.03 (m, 8H), 4.17-4.45 (m, 1H), 5.35 (br s, 1H),
7.53 (dd, J=7.3, 7.3 Hz, 1H), 7.67 (d, J=7.3 Hz, 1H), 8.02 (s,
1H), 8.29 (d, J=7.3 Hz, 1H), 8.82 (s, 1H).

Example 72

(S)-6-(2,3-Dimethyl-4-oxo-4H-pyrido[1,2-a]pyrimi-
din-9-yl)-2-(2-fluoroethylamino)-6,7,7a,8,9,10-hexa-
hydro-5H-pyrimido[5,4-f]pyrrolo[1,2-a][1,4]diaz-
epin-5-one (Compound 72)

Compound 72 was obtained in the same manner as in
steps 2 and 3 of Example 34, using (S)-6-(2,3-dimethyl-4-
oxo-4H-pyrido[1,2-a]pyrimidin-9-yl)-2-methylthio-6,7,7a,
8,9,10-hexahydro-5H-pyrimido[5,4-f]pyrrolo[1,2-a][1,4]di-
azepin-5-one obtained in step 1 of Example 7, and
2-fluoroethylamine monohydrochloride.
ESI-MS: m/z 438 [M+H]$^+$. $^1$H-NMR (CDCl$_3$) δ (ppm):
1.52-1.74 (m, 1H), 1.83-2.12 (m, 2H), 2.17-2.31 (m, 4H),
2.43 (s, 3H), 3.62-3.92 (m, 6H), 4.49-4.73 (m, 3H), 5.46 (br
s, 1H), 7.07 (dd, J=7.0, 7.0 Hz, 1H), 7.63 (dd, J=7.0, 1.5 Hz,
1H), 8.84 (s, 1H), 8.95 (dd, J=7.0, 1.5 Hz, 1H).

Example 73

(S)-2-(2,2-Difluoroethylamino)-6-(2,3-dimethyl-4-
oxo-4H-pyrido[1,2-a]pyrimidin-9-yl)-6,7,7a,8,9,10-
hexahydro-5H-pyrimido[5,4-f]pyrrolo[1,2-a][1,4]
diazepin-5-one (Compound 73)

Compound 73 was obtained in the same manner as in
steps 2 and 3 of Example 34, using (S)-6-(2,3-dimethyl-4-
oxo-4H-pyrido[1,2-a]pyrimidin-9-yl)-2-methylthio-6,7,7a,
8,9,10-hexahydro-5H-pyrimido[5,4-f]pyrrolo[1,2-a][1,4]di-
azepin-5-one obtained in step 1 of Example 7, and 2,2-
difluoroethylamine.
ESI-MS: m/z 456 [M+H]$^+$. $^1$H-NMR (CDCl$_3$) δ (ppm):
1.60-1.80 (m, 1H), 1.85-2.15 (m, 2H), 2.16-2.36 (m, 4H),
2.43 (s, 3H), 3.59-4.01 (m, 6H), 4.23-4.90 (m, 1H), 5.47-
6.20 (m, 2H), 7.08 (dd, J=7.8, 6.8 Hz, 1H), 7.63 (d, J=6.8
Hz, 1H), 8.84 (s, 1H), 8.96 (d, J=7.8 Hz, 1H).

Example 74

(S)-6-(2,3-Dimethyl-4-oxo-4H-pyrido[1,2-a]pyrimi-
din-9-yl)-2-propylamino-6,7,7a,8,9,10-hexahydro-
5H-pyrimido[5,4-f]pyrrolo[1,2-a][1,4]diazepin-5-
one (Compound 74)

Compound 74 was obtained in the same manner as in
steps 2 and 3 of Example 34, using (S)-6-(2,3-dimethyl-4-
oxo-4H-pyrido[1,2-a]pyrimidin-9-yl)-2-methylthio-6,7,7a,
8,9,10-hexahydro-5H-pyrimido[5,4-f]pyrrolo[1,2-a][1,4]di-
azepin-5-one obtained in step 1 of Example 7, and
1-propylamine.
ESI-MS: m/z 434 [M+H]$^+$. $^1$H-NMR (CDCl$_3$) δ (ppm):
0.99 (t, J=7.0 Hz, 3H), 1.55-1.72 (m, 3H), 1.84-2.11 (m, 2H),
2.16-2.28 (m, 4H), 2.43 (s, 3H), 3.33-3.48 (m, 2H), 3.61-
3.96 (m, 4H), 4.31-4.79 (m, 1H), 5.23 (br s, 1H), 7.07 (dd,
J=7.3, 7.3 Hz, 1H), 7.63 (d, J=7.3 Hz, 1H), 8.83 (s, 1H), 8.95
(d, J=7.3 Hz, 1H).

Example 75

(S)-2-Ethylamino-6-(4-oxo-2-trifluoromethyl-4H-pyrido[1,2-a]pyrimidin-9-yl)-6,7,7a,8,9,10-hexahydro-5H-pyrimido[5,4-f]pyrrolo[1,2-a][1,4]diazepin-5-one (Compound 75)

Compound 75 was obtained in the same manner as in steps 1 and 2 of Example 34, and Example 35, using Compound aq obtained in Reference Example 29.

ESI-MS: m/z 460 [M+H]$^+$. $^1$H-NMR (CDCl$_3$) δ (ppm): 1.22-1.31 (m, 3H), 1.55-1.73 (m, 1H), 1.83-2.17 (m, 2H), 2.21-2.34 (m, 1H), 3.42-3.58 (m, 2H), 3.63-4.03 (m, 4H), 4.52-4.72 (m, 1H), 6.17 (br s, 1H), 6.80 (s, 1H), 7.33 (dd, J=7.3, 7.0 Hz, 1H), 7.95 (dd, J=7.3, 1.5 Hz, 1H), 8.84 (s, 1H), 9.06 (dd, J=7.0, 1.5 Hz, 1H).

Example 76

(S)-2-Methylamino-6-(4-oxo-2-trifluoromethyl-4H-pyrido[1,2-a]pyrimidin-9-yl)-6,7,7a,8,9,10-hexahydro-5H-pyrimido[5,4-f]pyrrolo[1,2-a][1,4]diazepin-5-one (Compound 76)

Compound 76 was obtained in the same manner as in Example 34, using Compound aq obtained in Reference Example 29.

ESI-MS: m/z 446 [M+H]$^+$. $^1$H-NMR (CDCl$_3$) δ (ppm): 1.56-1.74 (m, 1H), 1.85-2.14 (m, 2H), 2.23-2.36 (m, 1H), 3.04 (d, J=3.7 Hz, 3H), 3.55-4.07 (m, 4H), 4.49-4.80 (m, 1H), 6.81 (br s, 1H), 7.34 (dd, J=7.1, 3.6 Hz, 1H), 7.95 (dd, J=7.3, 1.5 Hz, 1H), 8.81 (s, 1H), 9.07 (dd, J=7.1, 1.5 Hz, 1H).

Example 77

(S)-6-(2-Ethyl-1-oxo-1,2-dihydroisoquinolin-5-yl)-2-ethylamino-6,7,7a,8,9,10-hexahydro-5H-pyrimido[5,4-f]pyrrolo[1,2-a][1,4]diazepin-5-one (Compound 77)

Compound 77 was obtained in the same manner as in steps 1 and 2 of Example 34, and Example 35, using Compound ar obtained in Reference Example 30.

ESI-MS: m/z 419 [M+H]$^+$. $^1$H-NMR (CDCl$_3$) δ (ppm): 1.25 (t, J=7.1 Hz, 3H), 1.36 (t, J=7.3 Hz, 3H), 1.53-2.23 (m, 4H), 3.40-4.17 (m, 9H), 5.31 (br s, 1H), 6.35 (d, J=7.7 Hz, 0.5H), 6.47 (d, J=7.7 Hz, 0.5H), 7.05-7.12 (m, 1H), 7.38-7.57 (m, 2H), 8.38-8.47 (m, 1H), 8.76-8.91 (m, 1H).

Example 78

(S)-6-(2-Ethyl-1-oxo-1,2-dihydroisoquinolin-5-yl)-2-methylamino-6,7,7a,8,9,10-hexahydro-5H-pyrimido[5,4-f]pyrrolo[1,2-a][1,4]diazepin-5-one (Compound 78)

Compound 78 was obtained in the same manner as in Example 34, using Compound ar obtained in Reference Example 30.

ESI-MS: m/z 405 [M+H]$^+$. $^1$H-NMR (CDCl$_3$) δ (ppm): 1.36 (t, J=7.3 Hz, 3H), 1.56-1.73 (m, 1H), 1.81-2.27 (m, 3H), 3.00-3.05 (m, 3H), 3.53-4.14 (m, 7H), 5.39 (br s, 1H), 6.35 (d, J=7.8 Hz, 0.6H), 6.47 (d, J=7.8 Hz, 0.4H), 7.05-7.12 (m, 1H), 7.42-7.54 (m, 2H), 8.40-8.49 (m, 1H), 8.76-8.92 (m, 1H).

Example 79

(S)-2-Amino-6-(2-ethyl-1-oxo-1,2-dihydroisoquinolin-5-yl)-6,7,7a,8,9,10-hexahydro-5H-pyrimido[5,4-f]pyrrolo[1,2-a][1,4]diazepin-5-one (Compound 79)

Compound 79 was obtained in the same manner as in step 1 of Example 34, and Example 44, using Compound ar obtained in Reference Example 30.

ESI-MS: m/z 391 [M+H]$^+$. $^1$H-NMR (CDCl$_3$) δ (ppm): 1.36 (t, J=7.3 Hz, 3H), 1.53-1.71 (m, 1H), 1.80-2.36 (m, 3H), 3.42-4.14 (m, 8H), 5.33 (br s, 2H), 6.34 (d, J=7.8 Hz, 0.6H), 6.46 (d, J=7.8 Hz, 0.4H), 7.04-7.12 (m, 1H), 7.41-7.54 (m, 2H), 8.40-8.45 (m, 1H), 8.80 (s, 0.6H), 8.86 (s, 0.4H).

Example 80

(S)-2-Amino-6-(2-methyl-1-oxo-1,2-dihydroisoquinolin-5-yl)-6,7,7a,8,9,10-hexahydro-5H-pyrimido[5,4-f]pyrrolo[1,2-a][1,4]diazepin-5-one (Compound 80)

Compound 80 was obtained in the same manner as in Example 44, using (S)-6-(2-methyl-1-oxo-1,2-dihydroisoquinolin-5-yl)-2-methylthio-6,7,7a,8,9,10-hexahydro-5H-pyrimido[5,4-f]pyrrolo[1,2-a][1,4]diazepin-5-one (270 mg, 0.663 mmol) obtained in step 1 of Example 17.

ESI-MS: m/z 377 [M+H]$^+$. $^1$H-NMR (CDCl$_3$) δ (ppm): 1.55-1.71 (m, 1H), 1.81-2.23 (m, 3H), 3.56-4.17 (m, 8H), 5.15 (br s, 2H), 6.32 (d, J=7.8 Hz, 0.6H), 6.44 (d, J=7.8 Hz, 0.4H), 7.04-7.12 (m, 1H), 7.42-7.55 (m, 2H), 8.40-8.45 (m, 1H), 8.82 (s, 0.6H), 8.87 (s, 0.4H).

Example 81

(S)-2-Ethylamino-6-(2-methyl-1-oxo-1,2,3,4-tetrahydroisoquinolin-5-yl)-6,7,7a,8,9,10-hexahydro-5H-pyrimido[5,4-f]pyrrolo[1,2-a][1,4]diazepin-5-one (Compound 81)

Compound 81 was obtained in the same manner as in steps 1 and 2 of Example 34, and Example 35, using Compound as obtained in Reference Example 31.

ESI-MS: m/z 407 [M+H]$^+$. $^1$H-NMR (CDCl$_3$) δ (ppm): 1.19-1.30 (m, 3H), 1.53-1.74 (m, 1H), 1.78-2.27 (m, 3H), 2.70-3.20 (m, 5H), 3.40-4.10 (m, 9H), 5.52 (br s, 1H), 7.20-7.32 (m, 1H), 7.34-7.44 (m, 1H), 8.04-8.11 (m, 1H), 8.72-8.87 (m, 1H).

Example 82

(S)-6-(2-Methyl-1-oxo-1,2,3,4-tetrahydroisoquinolin-5-yl)-2-methylamino-6,7,7a,8,9,10-hexahydro-5H-pyrimido[5,4-f]pyrrolo[1,2-a][1,4]diazepin-5-one (Compound 82)

Compound 82 was obtained in the same manner as in Example 34, using Compound as obtained in Reference Example 31.

ESI-MS: m/z 393 [M+H]$^+$. $^1$H-NMR (CDCl$_3$) δ (ppm): 1.54-1.77 (m, 1H), 1.80-2.27 (m, 3H), 2.70-3.11 (m, 5H), 3.15 (s, 3H), 3.40-4.09 (m, 7H), 5.20 (br s, 1H), 7.21-7.33 (m, 1H), 7.34-7.45 (m, 1H), 8.04-8.11 (m, 1H), 8.75-8.88 (m, 1H).

Example 83

(S)-2-Ethylamino-6-(1-methyl-2-oxo-1,2,3,4-tetra-hydroquinolin-5-yl)-6,7,7a,8,9,10-hexahydro-5H-pyrimido[5,4-f]pyrrolo[1,2-a][1,4]diazepin-5-one (Compound 83)

Compound 83 was obtained in the same manner as in steps 1 and 2 of Example 34, and Example 35, using Compound at obtained in Reference Example 32.
ESI-MS: m/z 407 [M+H]$^+$. $^1$H-NMR (CDCl$_3$) δ (ppm): 1.26 (t, J=7.0 Hz, 3H), 1.54-2.27 (m, 4H), 2.47-2.97 (m, 4H), 3.30-3.61 (m, 5H), 3.70-4.12 (m, 5H), 5.35 (br s, 1H), 6.84-7.00 (m, 2H), 7.24-7.37 (m, 1H), 8.73-8.83 (m, 1H).

Example 84

(S)-6-(1-Methyl-2-oxo-1,2,3,4-tetrahydroquinolin-5-yl)-2-methylamino-6,7,7a,8,9,10-hexahydro-5H-pyrimido[5,4-f]pyrrolo[1,2-a][1,4]diazepin-5-one (Compound 84)

Compound 84 was obtained in the same manner as in Example 34, using Compound at obtained in Reference Example 32.
ESI-MS: m/z 393 [M+H]$^+$. $^1$H-NMR (CDCl$_3$) δ (ppm): 1.57-1.98 (m, 2H), 1.99-2.10 (m, 1H), 2.12-2.25 (m, 1H), 2.47-3.05 (m, 7H), 3.35-3.39 (m, 3H), 3.49-4.09 (m, 5H), 5.34 (br s, 1H), 6.84-7.00 (m, 2H), 7.25-7.34 (m, 1H), 8.75-8.86 (m, 1H).

Example 85

(S)-2-Amino-6-(3-methyl-4-oxo-3,4-dihydroquinazolin-5-yl)-6,7,7a,8,9,10-hexahydro-5H-pyrimido[5,4-f]pyrrolo[1,2-a][1,4]diazepin-5-one (Compound 85)

Compound 85 was obtained in the same manner as in Example 44, using (S)-6-(3-methyl-4-oxo-3,4-dihydroquinazolin-5-yl)-2-methylthio-6,7,7a,8,9,10-hexahydro-5H-pyrimido[5,4-f]pyrrolo[1,2-a][1,4]diazepin-5-one (0.100 g, 0.245 mmol) obtained in step 1 of Example 15.
ESI-MS: m/z 378 [M+H]$^+$. $^1$H-NMR (CDCl$_3$) δ (ppm): 1.62 (m, 1H), 1.89 (m, 1H), 2.00 (m, 1H), 2.14 (m, 1H), 3.50 (m, 3H), 3.66-4.15 (m, 4.5H), 4.59 (m, 0.5H), 4.96 (br s, 2H), 7.21 (dd, J=1.5, 7.3 Hz, 0.5H), 7.30 (dd, J=1.5, 7.3 Hz, 0.5H), 7.65-7.79 (m, 2H), 8.02 (s, 1H), 8.84 (s, 0.5H), 8.88 (s, 0.5H).

Example 86

(S)-6-(3-Ethyl-4-oxo-3,4-dihydroquinazolin-5-yl)-2-ethylamino-6,7,7a,8,9,10-hexahydro-5H-pyrimido[5,4-f]pyrrolo[1,2-a][1,4]diazepin-5-one (Compound 86)

Compound 86 was obtained in the same manner as in steps 1 and 2 of Example 34, and Example 35, using Compound au in Reference Example 33.
ESI-MS: m/z 420 [M+H]$^+$. $^1$H-NMR (CDCl$_3$) δ (ppm): 1.24 (t, J=7.8 Hz, 3H), 1.37 (t, J=6.8 Hz, 3H), 1.62 (m, 1H), 1.89 (m, 1H), 2.01 (m, 1H), 2.14 (m, 1H), 3.42-3.54 (m, 2H), 3.72-4.15 (m, 6.5H), 4.58 (m, 0.5H), 5.07 (br s, 1H), 7.21 (d, J=6.8 Hz, 0.5H), 7.30 (d, J=6.8 Hz, 0.5H), 7.64-7.77 (m, 2H), 8.02 (s, 1H), 8.83 (s, 0.5H), 8.86 (s, 0.5H).

Example 87

(S)-6-(3-Ethyl-4-oxo-3,4-dihydroquinazolin-5-yl)-2-methylamino-6,7,7a,8,9,10-hexahydro-5H-pyrimido[5,4-f]pyrrolo[1,2-a][1,4]diazepin-5-one (Compound 87)

Compound 87 was obtained in the same manner as in Example 34, using Compound aq in Reference Example 29.
ESI-MS: m/z 406 [M+H]$^+$. $^1$H-NMR (CDCl$_3$) δ (ppm): 1.36 (t, J=6.8 Hz, 3H), 1.63 (m, 1H), 1.89 (m, 1H), 2.01 (m, 1H), 2.14 (m, 1H), 3.01 (d, J=4.8 Hz, 3H), 3.74-4.15 (m, 6.5H), 4.58 (m, 0.5H), 5.05 (br s, 1H), 7.21 (d, J=6.8 Hz, 0.5H), 7.30 (d, J=6.8 Hz, 0.5H), 7.64-7.77 (m, 2H), 8.02 (s, 1H), 8.84 (s, 0.5H), 8.87 (s, 0.5H).

Example 88

(S)-6-(2,3-Dimethyl-4-oxo-3,4-dihydroquinazolin-5-yl)-2-ethylamino-6,7,7a,8,9,10-hexahydro-5H-pyrimido[5,4-f]pyrrolo[1,2-a][1,4]diazepin-5-one (Compound 88)

Compound 88 was obtained in the same manner as in steps 1 and 2 of Example 34, and Example 35, using Compound av in Reference Example 34.
ESI-MS: m/z 420 [M+H]$^+$.
$^1$H-NMR (CDCl$_3$) δ (ppm): 1.24 (t, J=7.3 Hz, 3H), 1.64 (m, 1H), 1.91 (m, 1H), 2.00 (m, 1H), 2.14 (m, 1H), 2.58 (s, 3H), 3.41-3.56 (m, 2H), 3.51 (s, 3H), 3.70-4.13 (m, 4.5H), 4.58 (m, 0.5H), 5.12 (br s, 1H), 7.14 (dd, J=1.1, 7.3 Hz, 0.5H), 7.23 (dd, J=1.1, 7.3 Hz, 0.5H), 7.54-7.75 (m, 2H), 8.83 (s, 0.5H), 8.86 (s, 0.5H).

Example 89

(S)-6-(2,3-Dimethyl-4-oxo-3,4-dihydroquinazolin-5-yl)-2-methylamino-6,7,7a,8,9,10-hexahydro-5H-pyrimido[5,4-f]pyrrolo[1,2-a][1,4]diazepin-5-one (Compound 89)

Compound 89 was obtained in the same manner as in Example 34, using Compound av in Reference Example 34.
ESI-MS: m/z 406 [M+H]$^+$. $^1$H-NMR (CDCl$_3$) δ (ppm): 1.64 (m, 1H), 1.90 (m, 1H), 2.02 (m, 1H), 2.14 (m, 1H), 2.58 (s, 3H), 3.01 (s, 3H), 3.52 (d, J=4.8 Hz, 3H), 3.73-4.13 (m, 4.5H), 4.60 (m, 0.5H), 5.05 (br s, 1H), 7.14 (dd, J=6.8 Hz, 0.5H), 7.23 (dd, J=6.8 Hz, 0.5H), 7.55-7.75 (m, 2H), 8.84 (s, 0.5H), 8.86 (s, 0.5H).

Example 90

(S)-3-(2-Ethylamino-5-oxo-7a,8,9,10-tetrahydro-5H-pyrimido[5,4-f]pyrrolo[1,2-a][1,4]diazepin-6(7H)-yl)-6-methylthieno[2,3-c]pyridin-7(6H)-one (Compound 90)

Compound 90 was obtained in the same manner as in steps 1 and 2 of Example 34, and Example 35, using Compound aw obtained in Reference Example 35.
ESI-MS: m/z 411 [M+H]$^+$. $^1$H-NMR (CDCl$_3$) δ (ppm): 1.25 (t, J=7.2 Hz, 3H), 1.56-1.76 (m, 1H), 1.78-2.13 (m, 2H), 2.14-2.26 (m, 1H), 3.41-3.54 (m, 2H), 3.63 (s, 3H), 3.71-4.02 (m, 5H), 6.05 (br s, 1H), 6.39 (d, J=7.2 Hz, 1H), 7.16 (d, J=7.2 Hz, 1H), 7.46 (s, 1H), 8.78 (s, 1H).

Example 91

(S)-6-Methyl-3-(2-methylamino-5-oxo-7a,8,9,10-tetrahydro-5H-pyrimido[5,4-f]pyrrolo[1,2-a][1,4]diazepin-6(7H)-yl)thieno[2,3-c]pyridin-7(6H)-one (Compound 91)

Compound 91 was obtained in the same manner as in Example 34, using Compound aw obtained in Reference Example 35.

ESI-MS: m/z 397 [M+H]$^+$. $^1$H-NMR (CDCl$_3$) δ (ppm): 1.48-1.97 (m, 2H), 1.99-2.12 (m, 1H), 2.14-2.26 (m, 1H), 3.02 (d, J=5.1 Hz, 3H), 3.64 (s, 3H), 3.71-4.01 (m, 5H), 5.23 (br s, 1H), 6.40 (d, J=7.3 Hz, 1H), 7.16 (d, J=7.3 Hz, 1H), 7.46 (d, J=0.7 Hz, 1H), 8.81 (s, 1H).

Example 92

(S)-3-(2-Amino-5-oxo-7a,8,9,10-tetrahydro-5H-pyrimido[5,4-f]pyrrolo[1,2-a][1,4]diazepin-6(7H)-yl)-6-methylthieno[2,3-c]pyridin-7(6H)-one (Compound 92)

Compound 92 was obtained in the same manner as in step 1 of Example 34, and Example 44, using Compound aw obtained in Reference Example 35.

ESI-MS: m/z 383 [M+H]$^+$. $^1$H-NMR (CDCl$_3$) δ (ppm): 1.55-1.74 (m, 1H), 1.77-2.12 (m, 2H), 2.14-2.26 (m, 1H), 3.64 (s, 3H), 3.70-4.01 (m, 5H), 5.11 (br s, 2H), 6.39 (d, J=7.2 Hz, 1H), 7.16 (d, J=7.2 Hz, 1H), 7.47 (s, 1H), 8.81 (s, 1H).

Example 93

(S)-6-(1,6-Dimethyl-7-oxo-6,7-dihydro-1H-pyrrolo[2,3-c]pyridin-3-yl)-2-ethylamino-6,7,7a,8,9,10-hexahydro-5H-pyrimido[5,4-f]pyrrolo[1,2-a][1,4]diazepin-5-one (Compound 93)

Compound 93 was obtained in the same manner as in steps 1 and 2 of Example 34, and Example 35, using Compound ax obtained in Reference Example 36.

ESI-MS: m/z 408 [M+H]$^+$. $^1$H-NMR (CDCl$_3$) δ (ppm): 1.26 (t, J=7.3 Hz, 3H), 1.55-1.74 (m, 1H), 1.79-2.12 (m, 2H), 2.14-2.25 (m, 1H), 3.42-3.53 (m, 2H), 3.57 (s, 3H), 3.67-4.00 (m, 5H), 4.16 (s, 3H), 6.26 (d, J=7.3 Hz, 1H), 6.56 (br s, 1H), 6.87 (d, J=7.3 Hz, 1H), 7.01 (s, 1H), 8.76 (s, 1H).

Example 94

(S)-6-(1,6-Dimethyl-7-oxo-6,7-dihydro-1H-pyrrolo[2,3-c]pyridin-3-yl)-2-methylamino-6,7,7a,8,9,10-hexahydro-5H-pyrimido[5,4-f]pyrrolo[1,2-a][1,4]diazepin-5-one (Compound 94)

Compound 94 was obtained in the same manner as in Example 34, using Compound ax obtained in Reference Example 36.

ESI-MS: m/z 394 [M+H]$^+$. $^1$H-NMR (DMSO-d$_6$) δ (ppm): 1.50-1.68 (m, 1H), 1.69-2.04 (m, 2H), 2.06-2.19 (m, 1H), 3.45 (s, 3H), 3.60-3.95 (m, 5H), 4.05 (s, 3H), 6.24 (d, J=7.0 Hz, 1H), 7.09 (br s, 1H), 7.13 (d, J=7.0 Hz, 1H), 7.32 (s, 1H), 8.46 (s, 1H).

Example 95

(S)-2-Amino-6-(1,6-dimethyl-7-oxo-6,7-dihydro-1H-pyrrolo[2,3-c]pyridin-3-yl)-6,7,7a,8,9,10-hexahydro-5H-pyrimido[5,4-f]pyrrolo[1,2-a][1,4]diazepin-5-one (Compound 95)

Compound 95 was obtained in the same manner as in step 1 of Example 34, and Example 44, using Compound ax obtained in Reference Example 36.

ESI-MS: m/z 380 [M+H]$^+$. $^1$H-NMR (CDCl$_3$) δ (ppm): 1.57-1.74 (m, 1H), 1.80-2.13 (m, 2H), 2.15-2.26 (m, 1H), 3.57 (s, 3H), 3.71-3.92 (m, 5H), 3.91-4.04 (m, 1H), 4.17 (s, 3H), 6.02-6.48 (m, 3H), 6.88 (d, J=7.3 Hz, 1H), 7.02 (s, 1H), 8.76 (s, 1H).

Example 96

(S)-3-Methyl-7-(2-(methylamino)-5-oxo-7a,8,9,10-tetrahydro-5H-pyrimido[5,4-f]pyrrolo[1,2-a][1,4]diazepin-6(7H)-yl)thieno[3,4-d]pyrimidin-4(3H)-one (Compound 96)

Compound 96 was obtained in the same manner as in Example 34, using Compound ay obtained in Reference Example 37.

ESI-MS: m/z 398 [M+H]$^+$. $^1$H-NMR (CDCl$_3$) δ (ppm): 8.83 (s, 1H), 8.00 (s, 1H), 7.66 (s, 1H), 5.26 (s, 1H), 4.75 (d, J=14.6 Hz, 1H), 4.27-4.17 (m, 1H), 3.95-3.66 (m, 3H), 3.49 (s, 3H), 3.01 (d, J=4.9 Hz, 3H), 2.43-2.30 (m, 1H), 2.12-2.01 (m, 1H), 1.99-1.84 (m, 1H), 1.75-1.60 (m, 1H).

Example 97

(S)-7-(2-(Ethylamino)-5-oxo-7a,8,9,10-tetrahydro-5H-pyrimido[5,4-f]pyrrolo[1,2-a][1,4]diazepin-6(7H)-yl)-3-methylthieno[3,4-d]pyrimidin-4(3H)-one (Compound 97)

Compound 97 was obtained in the same manner as in steps 1 and 2 of Example 34, and Example 35, using Compound ay obtained in Reference Example 37.

ESI-MS: m/z 412 [M+H]$^+$. $^1$H-NMR (CDCl$_3$) δ (ppm): 8.83 (s, 1H), 8.00 (s, 1H), 7.66 (s, 1H), 5.25 (s, 1H), 4.75 (d, J=15.6 Hz, 1H), 4.27-4.17 (m, 1H), 3.89-3.65 (m, 3H), 3.49 (s, 3H), 3.46 (q, J=6.8 Hz, 2H), 2.41-2.30 (m, 1H), 2.12-2.00 (m, 1H), 1.99-1.84 (m, 1H), 1.75-1.59 (m, 1H), 1.24 (t, J=7.3 Hz, 3H).

Example 98

(S)-3-Methyl-7-(2-(methylamino)-5-oxo-7a,8,9,10-tetrahydro-5H-pyrimido[5,4-f]pyrrolo[1,2-a][1,4]diazepin-6(7H)-yl)thieno[3,2-d]pyrimidin-4(3H)-one (Compound 98)

Compound 98 was obtained in the same manner as in Example 34, using Compound az obtained in Reference Example 38.

ESI-MS: m/z 398 [M+H]$^+$. $^1$H-NMR (CDCl$_3$) δ (ppm): 8.80 (s, 1H), 8.05 (s, 1H), 7.81 (s, 1H), 5.18 (s, 1H), 4.27-4.15 (m, 1H), 3.95 (d, J=13.9 Hz, 1H), 3.88-3.74 (m, 3H), 3.62 (s, 3H), 3.01 (d, J=5.1 Hz, 3H), 2.29-2.16 (m, 1H), 2.10-1.80 (m, 2H), 1.73-1.56 (m, 1H).

Example 99

(S)-7-(2-(Ethylamino)-5-oxo-7a,8,9,10-tetrahydro-5H-pyrimido[5,4-f]pyrrolo[1,2-a][1,4]diazepin-6(7H)-yl)-3-methylthieno[3,2-d]pyrimidin-4(3H)-one (Compound 99)

Compound 99 was obtained in the same manner as in steps 1 and 2 of Example 34, and Example 35, using Compound az obtained in Reference Example 38.
ESI-MS: m/z 412 [M+H]$^+$. $^1$H-NMR (CDCl$_3$) δ (ppm): 8.79 (s, 1H), 8.05 (s, 1H), 7.80 (s, 1H), 5.34 (s, 1H), 4.26-4.14 (m, 1H), 3.94 (d, J=13.9 Hz, 1H), 3.88-3.74 (m, 3H), 3.62 (s, 3H), 3.53-3.40 (m, 2H), 2.30-2.16 (m, 1H), 2.12-1.78 (m, 2H), 1.74-1.54 (m, 1H), 1.24 (t, J=7.3 Hz, 3H).

Example 100

(S)-3-(2-Fluoroethyl)-7-(2-(methylamino)-5-oxo-7a,8,9,10-tetrahydro-5H-pyrimido[5,4-f]pyrrolo[1,2-a][1,4]diazepin-6(7H)-yl)thieno[3,2-d]pyrimidin-4(3H)-one (Compound 100)

Compound 100 was obtained in the same manner as in Example 34, using Compound ba obtained in Reference Example 39.
ESI-MS: m/z 430 [M+H]$^+$. $^1$H-NMR (CDCl$_3$) δ (ppm): 8.81 (s, 1H), 8.06 (s, 1H), 7.85 (s, 1H), 5.16 (s, 1H), 4.75 (dt, J=46.8, 4.4 Hz, 2H), 4.41-4.19 (m, 3H), 3.97 (d, J=15.6 Hz, 1H), 3.91-3.70 (m, 3H), 3.01 (d, J=4.9 Hz, 3H), 2.31-2.21 (m, 1H), 2.10-1.99 (m, 1H), 1.98-1.82 (m, 1H), 1.72-1.62 (m, 1H).

Example 101

(S)-7-(2-(Ethylamino)-5-oxo-7a,8,9,10-tetrahydro-5H-pyrimido[5,4-f]pyrrolo[1,2-a][1,4]diazepin-6(7H)-yl)-3-(2-fluoroethyl)thieno[3,2-d]pyrimidin-4(3H)-one (Compound 101)

Compound 101 was obtained in the same manner as in steps 1 and 2 of Example 34, and Example 35, using Compound ba obtained in Reference Example 39.
ESI-MS: m/z 444 [M+H]$^+$. $^1$H-NMR (CDCl$_3$) δ (ppm): 8.80 (s, 1H), 8.06 (s, 1H), 7.85 (s, 1H), 5.19 (s, 1H), 4.75 (dt, J=46.8, 4.4 Hz, 2H), 4.42-4.18 (m, 3H), 3.97 (t, J=9.3 Hz, 1H), 3.88-3.71 (m, 3H), 3.52-3.42 (m, 2H), 2.30-2.20 (m, 1H), 2.09-1.98 (m, 1H), 1.98-1.83 (m, 1H), 1.72-1.62 (m, 1H), 1.24 (t, J=6.8 Hz, 3H).

Example 102

(S)-3-(2-Fluoroethyl)-2-methyl-7-(2-(methylamino)-5-oxo-7a,8,9,10-tetrahydro-5H-pyrimido[5,4-f]pyrrolo[1,2-a][1,4]diazepin-6(7H)-yl)thieno[3,2-d]pyrimidin-4(3H)-one (Compound 102)

Compound 102 was obtained in the same manner as in Example 34, using Compound bb obtained in Reference Example 40.
ESI-MS: m/z 444 [M+H]$^+$. $^1$H-NMR (CDCl$_3$) δ (ppm): 8.81 (s, 1H), 7.84 (s, 1H), 5.13 (s, 1H), 4.79 (dt, J=47.5, 4.6 Hz, 2H), 4.51-4.39 (m, 2H), 4.35-4.27 (m, 1H), 4.02 (d, J=14.6 Hz, 1H), 3.90-3.74 (m, 3H), 3.02 (d, J=4.9 Hz, 3H), 2.66 (s, 3H), 2.32-2.23 (m, 1H), 2.12-2.00 (m, 1H), 2.01-1.83 (m, 1H), 1.74-1.64 (m, 1H).

Example 103

(S)-7-(2-(Ethylamino)-5-oxo-7a,8,9,10-tetrahydro-5H-pyrimido[5,4-f]pyrrolo[1,2-a][1,4]diazepin-6(7H)-yl)-3-(2-fluoroethyl)-2-methylthieno[3,2-d]pyrimidin-4(3H)-one (Compound 103)

Compound 103 was obtained in the same manner as in steps 1 and 2 of Example 34, and Example 35, using Compound bb obtained in Reference Example 40.
ESI-MS: m/z 458 [M+H]$^+$. $^1$H-NMR (CDCl$_3$) δ (ppm): 8.80 (s, 1H), 7.84 (s, 1H), 5.17 (s, 1H), 4.79 (dt, J=47.2, 4.4 Hz, 2H), 4.53-4.38 (m, 2H), 4.35-4.26 (m, 1H), 4.01 (d, J=14.6 Hz, 1H), 3.88-3.72 (m, 3H), 3.52-3.42 (m, 2H), 2.66 (s, 3H), 2.32-2.22 (m, 1H), 2.11-1.99 (m, 1H), 1.98-1.83 (m, 1H), 1.75-1.62 (m, 1H), 1.24 (t, J=7.3 Hz, 3H).

Example 104

(S)-5-Methyl-3-(2-(methylamino)-5-oxo-7a,8,9,10-tetrahydro-5H-pyrimido[5,4-f]pyrrolo[1,2-a][1,4]diazepin-6(7H)-yl)thieno[3,2-c]pyridin-4(5H)-one (Compound 104)

Compound 104 was obtained in the same manner as in Example 34, using Compound bc obtained in Reference Example 41.
ESI-MS: m/z 397 [M+H]$^+$. $^1$H-NMR (CDCl$_3$) δ (ppm): 8.84 (s, 1H), 7.14 (d, J=7.8 Hz, 1H), 7.10 (s, 1H), 6.60 (d, J=6.8 Hz, 1H), 5.10 (s, 1H), 4.63-4.07 (m, 1H), 4.07-3.60 (m, 4H), 3.54 (s, 3H), 3.00 (d, J=4.9 Hz, 3H), 2.23-2.08 (m, 1H), 2.07-1.77 (m, 2H), 1.70-1.53 (m, 1H).

Example 105

(S)-3-(2-(Ethylamino)-5-oxo-7a,8,9,10-tetrahydro-5H-pyrimido[5,4-f]pyrrolo[1,2-a][1,4]diazepin-6(7H)-yl)-5-methylthieno[3,2-c]pyridin-4(5H)-one (Compound 105)

Compound 105 was obtained in the same manner as in steps 1 and 2 of Example 34, and Example 35, using Compound bc obtained in Reference Example 41.
ESI-MS: m/z 411 [M+H]$^+$. $^1$H-NMR (CDCl$_3$) δ (ppm): 8.84 (s, 1H), 7.14 (d, J=6.8 Hz, 1H), 7.10 (s, 1H), 6.60 (d, J=7.8 Hz, 1H), 5.12 (s, 1H), 4.65-4.09 (m, 1H), 4.09-3.59 (m, 4H), 3.54 (s, 3H), 3.51-3.40 (m, 2H), 2.20-2.07 (m, 1H), 2.05-1.79 (m, 2H), 1.68-1.53 (m, 1H), 1.23 (t, J=6.8 Hz, 3H).

Example 106

(S)-5-Methyl-3-(2-(methylamino)-5-oxo-7a,8,9,10-tetrahydro-5H-pyrimido[5,4-f]pyrrolo[1,2-a][1,4]diazepin-6(7H)-yl)furo[3,2-c]pyridin-4(5H)-one (Compound 106)

Compound 106 was obtained in the same manner as in Example 34, using Compound bd obtained in Reference Example 42.
ESI-MS: m/z 381 [M+H]$^+$. $^1$H-NMR (CDCl$_3$) δ (ppm): 8.81 (s, 1H), 7.72 (s, 1H), 7.20 (d, J=6.8 Hz, 1H), 6.49 (d, J=6.8 Hz, 1H), 5.11 (s, 1H), 4.31-4.20 (m, 1H), 3.95 (d, J=14.6 Hz, 1H), 3.89-3.70 (m, 3H), 3.57 (s, 3H), 3.00 (d, J=4.9 Hz, 3H), 2.35-2.25 (m, 1H), 2.06-1.84 (m, 2H), 1.66-1.57 (m, 1H).

Example 107

(S)-3-(2-(Ethylamino)-5-oxo-7a,8,9,10-tetrahydro-5H-pyrimido[5,4-f]pyrrolo[1,2-a][1,4]diazepin-6(7H)-yl)-5-methylfuro[3,2-c]pyridin-4(5H)-one (Compound 107)

Compound 107 was obtained in the same manner as in steps 1 and 2 of Example 34, and Example 35, using Compound bd obtained in Reference Example 42.
ESI-MS: m/z 395 [M+H]$^+$. $^1$H-NMR (CDCl$_3$) δ (ppm): 8.81 (s, 1H), 7.72 (s, 1H), 7.20 (d, J=7.8 Hz, 1H), 6.49 (d, J=6.8 Hz, 1H), 5.12 (s, 1H), 4.32-4.17 (m, 1H), 3.94 (d, J=14.6 Hz, 1H), 3.88-3.70 (m, 3H), 3.57 (s, 3H), 3.51-3.42 (m, 2H), 2.35-2.25 (m, 1H), 2.06-1.82 (m, 2H), 1.66-1.57 (m, 1H), 1.23 (t, J=7.3 Hz, 3H).

Example 108

(S)-(2-Amino-5-oxo-7a,8,9,10-tetrahydro-5H-pyrimido[5,4-f]pyrrolo[1,2-a][1,4]diazepin-6(7H)-yl)-5-methylfuro[3,2-c]pyridin-4(5H)-one (Compound 108)

Compound 108 was obtained in the same manner as in step 1 of Example 34, and Example 44, using Compound bd obtained in Reference Example 42.
ESI-MS: m/z 367 [M+H]$^+$. $^1$H-NMR (CDCl$_3$) δ (ppm): 8.82 (s, 1H), 7.72 (s, 1H), 7.20 (d, J=7.7 Hz, 1H), 6.49 (d, J=7.7 Hz, 1H), 4.99 (s, 2H), 4.32-4.20 (m, 1H), 3.95 (d, J=13.9 Hz, 1H), 3.81 (dd, J=15.0, 7.3 Hz, 1H), 3.78-3.63 (m, 2H), 3.57 (s, 3H), 2.37-2.26 (m, 1H), 2.07-1.83 (m, 2H), 1.68-1.51 (m, 1H).

Example 109

(S)-6-(3,7-Dimethyl-4-oxo-4,7-dihydro-3H-pyrrolo[2,3-d]pyrimidin-5-yl)-2-(methylamino)-6,7,7a,8,9,10-hexahydro-5H-pyrimido[5,4-f]pyrrolo[1,2-a][1,4]diazepin-5-one (Compound 109)

Compound 109 was obtained in the same manner as in Example 34, using Compound be obtained in Reference Example 43.
ESI-MS: m/z 395 [M+H]$^+$. $^1$H-NMR (CDCl$_3$) δ (ppm): 8.80 (s, 1H), 7.84 (s, 1H), 6.97 (s, 1H), 5.25 (s, 1H), 4.32-4.20 (m, 1H), 3.93 (d, J=14.6 Hz, 1H), 3.88-3.70 (m, 6H), 3.53 (s, 3H), 3.00 (d, J=4.9 Hz, 3H), 2.36-2.22 (m, 1H), 2.08-1.84 (m, 2H), 1.70-1.54 (m, 1H).

Example 110

(S)-6-(3,7-Dimethyl-4-oxo-4,7-dihydro-3H-pyrrolo[2,3-d]pyrimidin-5-yl)-2-(ethylamino)-6,7,7a,8,9,10-hexahydro-5H-pyrimido[5,4-f]pyrrolo[1,2-a][1,4]diazepin-5-one (Compound 110)

Compound 110 was obtained in the same manner as in steps 1 and 2 of Example 34, and Example 35, using Compound be obtained in Reference Example 43.
ESI-MS: m/z 409 [M+H]$^+$. $^1$H-NMR (CDCl$_3$) δ (ppm): 8.79 (s, 1H), 7.84 (s, 1H), 6.97 (s, 1H), 5.30 (s, 1H), 4.32-4.21 (m, 1H), 3.93 (d, J=14.6 Hz, 1H), 3.88-3.71 (m, 6H), 3.53 (s, 3H), 3.51-3.41 (m, 2H), 2.33-2.21 (m, 1H), 2.07-1.82 (m, 2H), 1.69-1.55 (m, 1H), 1.24 (t, J=7.3 Hz, 3H).

Example 111

(S)-2-Amino-6-(3,7-dimethyl-4-oxo-4,7-dihydro-3H-pyrrolo[2,3-d]pyrimidin-5-yl)-6,7,7a,8,9,10-hexahydro-5H-pyrimido[5,4-f]pyrrolo[1,2-a][1,4]diazepin-5-one (Compound 111)

Compound 111 was obtained in the same manner as in step 1 of Example 34, and Example 44, using Compound be obtained in Reference Example 43.
ESI-MS: m/z 381 [M+H]$^+$. $^1$H-NMR (CDCl$_3$) δ (ppm): 8.80 (s, 1H), 7.85 (s, 1H), 6.97 (s, 1H), 5.11 (s, 2H), 4.31-4.22 (m, 1H), 3.92 (d, J=14.6 Hz, 1H), 3.82 (dd, J=15.1, 7.3 Hz, 1H), 3.78-3.62 (m, 2H), 3.54 (s, 3H), 2.31-2.22 (m, 1H), 2.05-1.82 (m, 5H), 1.68-1.54 (m, 1H).

Example 112

(S)-6-(3-Methyl-4-oxo-4,7-dihydro-3H-pyrrolo[2,3-d]pyrimidin-5-yl)-2-(methylamino)-6,7,7a,8,9,10-hexahydro-5H-pyrimido[5,4-f]pyrrolo[1,2-a][1,4]diazepin-5-one (Compound 112)

Step 1
Toluene (4 mL), N,N'-dimethylethylenediamine (0.243 mL, 2.28 mmol), and copper(I) iodide (207 mg, 1.09 mmol) were successively added to a mixture of (S)-2-methylthio-6,7,7a,8,9,10-hexahydro-5H-pyrimido[5,4-f]pyrrolo[1,2-a][1,4]diazepin-5-one (408 mg, 1.63 mmol) obtained in Reference Example 3 of WO2008/149834, Compound bf (415 mg, 1.09 mmol) obtained in Reference Example 44, and potassium carbonate (450 mg, 3.26 mmol). The mixture was stirred under a nitrogen atmosphere at 10° C. for 2 hours. The reaction mixture was cooled to room temperature, and filtered through Celite. The filtrate was concentrated under reduced pressure, and the obtained residue was purified by silica gel column chromatography (chloroform/methanol) to give (S)-6-(3-methyl-4-oxo-7-tosyl-4,7-dihydro-3H-pyrrolo[2,3-d]pyrimidin-5-yl)-2-(methylthio)-6,7,7a,8,9,10-hexahydro-5H-pyrimido[5,4-f]pyrrolo[1,2-a][1,4]diazepin-5-one (197 mg, 33%).
ESI-MS: m/z 552 [M+H]$^+$. $^1$H-NMR (CDCl$_3$) δ (ppm): 8.83 (s, 1H), 8.10-8.03 (m, 2H), 7.95 (s, 1H), 7.51 (s, 1H), 7.33 (d, J=8.4 Hz, 2H), 4.30-4.19 (m, 1H), 3.92-3.73 (m, 4H), 3.50 (s, 3H), 2.54 (s, 3H), 2.42 (s, 3H), 2.32-2.21 (m, 1H), 2.12-1.83 (m, 2H), 1.72-1.56 (m, 1H).
Step 2
(S)-6-(3-Methyl-4-oxo-7-tosyl-4,7-dihydro-3H-pyrrolo[2,3-d]pyrimidin-5-yl)-2-(methylthio)-6,7,7a,8,9,10-hexahydro-5H-pyrimido[5,4-f]pyrrolo[1,2-a][1,4]diazepin-5-one (195 mg, 0.353 mmol) obtained in step 1 was suspended in THF (3 mL), and a 1 mol/L sodium hydroxide aqueous solution (3.53 mL, 3.53 mmol) and 2-propanol (1 mL) were added. The mixture was stirred at room temperature for 6 hours. After neutralizing the reaction mixture by addition of a saturated ammonium chloride aqueous solution, water was added to the residue obtained by concentrating the mixture under reduced pressure. The insoluble matter was collected by filtration, and washed with water and diethyl ether to give (S)-6-(3-methyl-4-oxo-4,7-dihydro-3H-pyrrolo[2,3-d]pyrimidin-5-yl)-2-(methylthio)-6,7,7a,8,9,10-hexahydro-5H-pyrimido[5,4-f]pyrrolo[1,2-a][1,4]diazepin-5-one (141 mg, 100%).

ESI-MS: m/z 398 [M+H]⁺. ¹H-NMR (DMSO-d₆) δ (ppm): 11.91 (s, 1H), 8.54 (s, 1H), 8.16 (s, 1H), 7.09 (s, 1H), 4.30-4.19 (m, 1H), 3.89-3.68 (m, 4H), 3.42 (s, 3H), 2.50 (s, 3H), 2.19-2.08 (m, 1H), 2.02-1.90 (m, 1H), 1.90-1.73 (m, 1H), 1.66-1.51 (m, 1H).

Step 3

(S)-6-(3-Methyl-4-oxo-4,7-dihydro-3H-pyrrolo[2,3-d]pyrimidin-5-yl)-2-(methylthio)-6,7,7a,8,9,10-hexahydro-5H-pyrimido[5,4-f]pyrrolo[1,2-a][1,4]diazepin-5-one (137 mg, 0.345 mmol) obtained in step 2 was dissolved in dichloromethane (3 mL), and m-CPBA (101 mg, 0.379 mmol) was added at 0° C. The mixture was stirred at 0° C. for 15 minutes. The reaction mixture was extracted with chloroform after adding a saturated sodium bicarbonate aqueous solution and saturated brine. The organic layer was dried over anhydrous sodium sulfate, and concentrated under reduced pressure to give a residue.

Step 4

A half amount of the residue obtained in step 3 was dissolved in THF (1 mL), and a 2 mol/L methylamine/THF solution (1 mL, 2.00 mmol) was added. The mixture was stirred at room temperature for 1 hour. The reaction mixture was extracted with chloroform after adding saturated brine. The organic layer was concentrated under reduced pressure, and the obtained residue was purified by HPLC (0.01 mol/L ammonium acetate aqueous solution/methanol) to give Compound 112 (11.4 mg, 2 steps 17%).

ESI-MS: m/z 381 [M+H]⁺. ¹H-NMR (DMSO-d₆) δ (ppm): 11.83 (s, 1H), 8.44 (s, 1H), 8.14 (s, 1H), 7.16-6.82 (m, 2H), 4.20-4.08 (m, 1H), 3.80-3.54 (m, 4H), 3.41 (s, 3H), 2.82 (d, J=4.9 Hz, 3H), 2.16-2.06 (m, 1H), 1.98-1.86 (m, 1H), 1.86-1.70 (m, 1H), 1.63-1.47 (m, 1H).

Example 113

(S)-2-(Ethylamino)-6-(3-methyl-4-oxo-4,7-dihydro-3H-pyrrolo[2,3-d]pyrimidin-5-yl)-6,7,7a,8,9,10-hexahydro-5H-pyrimido[5,4-f]pyrrolo[1,2-a][1,4]diazepin-5-one (Compound 113)

A half amount of the residue obtained in step 3 of Example 112 was dissolved in THF (1 mL), and a 2 mol/L ethylamine/THF solution (1 mL, 2.00 mmol) was added. The mixture was stirred at room temperature for 1 hour. The reaction mixture was extracted with chloroform after adding saturated brine. The organic layer was concentrated under reduced pressure, and the obtained residue was purified by HPLC (0.01 mol/L ammonium acetate aqueous solution/methanol) to give Compound 113 (11.2 mg, 2 steps 16%).

ESI-MS: m/z 395 [M+H]⁺. ¹H-NMR (DMSO-d₆) δ (ppm): 11.83 (s, 1H), 8.45 (s, 1H), 8.14 (s, 1H), 7.27-6.88 (m, 2H), 4.22-4.08 (m, 1H), 3.89-3.54 (m, 4H), 3.41 (s, 3H), 3.36-3.25 (m, 2H), 2.21-2.02 (m, 1H), 2.03-1.87 (m, 1H), 1.87-1.69 (m, 1H), 1.69-1.48 (m, 1H), 1.18-1.08 (m, 3H).

Example 114

(S)-2-Methylamino-6-(3-methyl-4-oxo-3H-thieno[2,3-d]pyrimidin-5-yl)-6,7,7a,8,9,10-hexahydro-5H-pyrimido[5,4-f]pyrrolo[1,2-a][1,4]diazepin-5-one (Compound 114)

Compound 114 was obtained in the same manner as in Example 34, using Compound bg in Reference Example 45.

ESI-MS: m/z 398 [M+H]⁺. ¹H-NMR (CDCl₃) δ (ppm): 1.79 (m, 1H), 1.92 (m, 1H), 2.11 (m, 1H), 2.39 (m, 1H), 3.01 (d, J=4.9 Hz, 3H), 3.61 (s, 3H), 3.71-3.92 (m, 4H), 4.34 (m, 1H), 5.62 (br s, 1H), 6.90 (s, 1H), 7.99 (s, 1H), 8.79 (s, 1H).

Example 115

(7aS,9R)-2-Ethylamino-9-fluoro-6-(3-methyl-4-oxo-3,4-dihydroquinazolin-8-yl)-6,7,7a,8,9,10-hexahydro-5H-pyrimido[5,4-f]pyrrolo[1,2-a][1,4]diazepin-5-one (Compound 115)

Step 1

Commercially available (2S,4R)-1-(tert-butoxycarbonyl)-4-fluoropyrrolidine-2-carboxylic acid (3.0 g, 12.9 mmol) was dissolved in 2,2-dimethoxyethane (43 mL). After cooling the mixture to −20° C., isobutyl chloroformate (1.86 mL, 14.2 mmol) and N-methylmorpholine (1.56 mL, 14.2 mmol) were added, and the mixture was stirred at −20° C. for 30 minutes. After removing the precipitate by filtration, the filtrate was cooled to −20° C., and a sodium borohydride (0.535 g, 14.2 mmol) aqueous solution (15 mL) was added. The mixture was stirred at −20° C. for 30 minutes. After concentrating the reaction mixture under reduced pressure, a 1 mol/L sodium hydroxide aqueous solution was added, and the mixture was extracted three times with ethyl acetate. The organic layer was dried over anhydrous magnesium sulfate, and concentrated under reduced pressure. The obtained residue was purified by silica gel column chromatography (heptane/ethyl acetate=3/1) to give (2S,4R)-tert-butyl 4-fluoro-2-(hydroxymethyl)pyrrolidine-1-carboxylate (2.81 g, quant.).

ESI-MS: m/z 120 [M−Boc+H]⁺. ¹H-NMR (CDCl₃, 80° C.) δ (ppm): 1.49 (s, 9H), 1.87 (m, 1H), 2.35 (m, 1H), 3.44 (ddd, J=3.3, 13.2, 35.9 Hz, 1H), 3.58 (dd, J=5.9, 11.7 Hz, 1H), 3.77-3.94 (m, 2H), 4.12 (m, 1H), 5.09 (ddd, J=4.0, 4.0, 53.1 Hz, 1H).

Step 2

(2S,4R)-tert-Butyl 4-fluoro-2-(hydroxymethyl)pyrrolidine-1-carboxylate (2.81 g, 12.8 mmol) obtained in step 1 was dissolved in toluene (64 mL), and N-Boc-2-nitrobenzenesulfonamide (5.81 g, 19.2 mmol), triphenylphosphine (5.04 g, 19.2 mmol), and a 40% diethylazodicarboxylate/toluene solution (7.61 mL, 19.2 mmol) were added. The mixture was stirred at 65° C. for 1 hour. The reaction mixture was cooled to room temperature, and the precipitate was removed by filtration. After adding a 2 mol/L sodium hydroxide aqueous solution to the filtrate, the mixture was extracted with toluene, and washed with saturated brine. The organic layer was dried over anhydrous magnesium sulfate, and concentrated under reduced pressure. The obtained residue was purified by silica gel column chromatography (heptane/ethyl acetate=3/1) to give (2S,4R)-tert-butyl 2-((N-(tert-butoxycarbonyl)-2-nitrophenylsulfonamido)methyl)-4-fluoropyrrolidine-1-carboxylate (2.92 g, 45%).

ESI-MS: m/z 504 [M+H]⁺. ¹H-NMR (CDCl₃, 80° C.) δ (ppm): 1.37 (s, 9H), 1.52 (s, 9H), 2.16 (m, 1H), 2.38 (m, 1H), 3.47 (ddd, J=4.0, 13.2, 33.4 Hz, 1H), 3.88-4.01 (m, 2H), 4.17 (dd, J=5.5, 14.7 Hz, 1H), 4.46 (m, 1H), 5.17 (brd, J=53.9 Hz, 1H), 7.64-7.74 (m, 3H), 8.30 (m, 1H).

Step 3

(2S,4R)-tert-Butyl 2-((N-(tert-butoxycarbonyl)-2-nitrophenylsulfonamido)methyl)-4-fluoropyrrolidine-1-carboxylate (2.79 g, 5.54 mmol) obtained in step 2 was dissolved in ethyl acetate (15 mL), and 4 mol/L hydrogen chloride/ethyl acetate (30 mL) was added. The mixture was stirred at room temperature for 3 hours. The precipitated crystals were collected by filtration to give N-(((2S,4R)-4-fluoropyrimidin-2-yl)methyl)-2-nitrobenzenesulfonamide (1.41 g, 75%).

ESI-MS: m/z 304 [M+H]⁺. ¹H-NMR (CDCl₃, 80° C.) δ (ppm): 1.94 (m, 1H), 2.33 (m, 1H), 3.30-3.67 (m, 4H), 3.85 (m, 1H), 5.41 (ddd, J=3.3, 3.3, 52.8 Hz, 1H), 7.85-7.99 (m, 3H), 8.09 (m, 1H), 8.36 (brs, 1H), 9.64 (brs, 1H).

Step 4

N-((2S,4R)-4-Fluoropyrimidin-2-yl)methyl)-2-nitrobenzenesulfonamide (1.41 g, 4.15 mmol) obtained in step 3 was dissolved in 1,4-dioxane (21 mL), and ethyl 4-chloro-2-methylthiopyrimidine-5-carboxylate (1.93 g, 8.30 mmol) and N,N-diisopropylethylamine (2.90 mL, 16.6 mmol) were added. The mixture was stirred at 90° C. for 2.5 hours. The reaction mixture was cooled to room temperature, diluted with ethyl acetate, and washed with water and saturated brine. The organic layer was dried over anhydrous magnesium sulfate, and concentrated under reduced pressure. The obtained residue was purified by silica gel column chromatography (heptane/ethyl acetate=1/1) to give ethyl 4-((2S,4R)-4-fluoro-2-((2-nitrophenylsulfonamido)pyrrolidin-1-yl)-2-(methylthio)pyrimidine-5-carboxylate (2.01 g, 97%).

ESI-MS: m/z 304 [M+H]⁺. ¹H-NMR (CDCl₃, 80° C.) δ (ppm): 1.37 (t, J=7.3 Hz, 3H), 2.17-2.57 (m, 2H), 2.45 (s, 3H), 3.10 (ddd, J=2.6, 13.5, 20.5 Hz, 1H), 3.45-3.65 (m, 2H), 3.89 (ddd, J=2.9, 13.6, 40.0 Hz, 1H), 4.33 (q, J=7.3 Hz, 2H), 4.89 (m, 1H), 5.23 (ddd, J=2.9, 2.9, 52.4 Hz, 1H), 5.70 (dd, J=4.8, 7.7 Hz, 1H), 7.67-7.83 (m, 3H), 8.08 (m, 1H), 8.55 (s, 1H).

Step 5

Ethyl 4-((2S,4R)-4-fluoro-2-((2-nitrophenylsulfonamido)pyrrolidin-1-yl)-2-(methylthio)pyrimidine-5-carboxylate (2.01 g, 4.02 mmol) obtained in step 4 was dissolved in ethanol (20 mL), and mercaptoacetic acid (1.12 mL, 16.1 mmol) and 1,8-diazabicyclo[5.4.0]-7-undecene (DBU)(4.85 mL, 32.2 mmol) were added. The mixture was stirred at 70° C. for 2 hours. The reaction mixture was concentrated under reduced pressure, diluted with ethyl acetate, and washed with a saturated sodium bicarbonate aqueous solution, water, and saturated brine. The organic layer was dried over anhydrous magnesium sulfate, and concentrated under reduced pressure. The obtained residue was purified by silica gel column chromatography (ethyl acetate) to give (7aS,9R)-9-fluoro-2-(methylthio)-6,7,7a,8,9,10-hexahydro-5H-pyrimido[1,2-a][1,4]diazepin-5-one (0.841 g, 78%).

ESI-MS: m/z 269 [M+H]⁺. ¹H-NMR (CDCl₃, 80° C.) δ (ppm): 1.86 (m, 1H), 2.55 (m, 1H), 2.54 (s, 3H), 3.35 (ddd, J=3.7, 8.1, 15.0 Hz, 1H), 3.57 (ddd, J=1.1, 8.4, 15.0 Hz, 1H), 4.01-4.23 (m, 3H), 5.31 (ddd, J=3.3, 3.3, 52.8 Hz, 1H), 7.42 (brs, 1H), 8.89 (s, 1H).

Step 6

Compound 115 was obtained in the same manner as in steps 1 and 2 of Example 34, and Example 35, using (7aS,9R)-9-fluoro-2-(methylthio)-6,7,7a,8,9,10-hexahydro-5H-pyrimido[1,2-a][1,4]diazepin-5-one obtained in step 5, and Compound e obtained in Reference Example 5.

ESI-MS: m/z 424 [M+H]⁺. ¹H-NMR (CDCl₃) δ (ppm): 1.25 (t, J=7.0 Hz, 3H), 1.76 (m, 1H), 2.40 (m, 1H), 3.42-3.53 (m, 2H), 3.58 (s, 3H), 3.72 (d, J=14.7 Hz, 1H), 3.91-4.26 (m, 4H), 4.64 (m, 1H), 5.20 (br s, 1H), 5.29 (ddd, J=3.3, 52.4 Hz, 1H), 7.54 (dd, J=7.7, 8.1 Hz, 1H), 7.69 (dd, J=1.5, 7.7 Hz, 1H), 8.03 (s, 1H), 8.30 (dd, J=1.5, 8.1 Hz, 1H), 8.84 (s, 1H).

Example 116

(7aS,9S)-9-Fluoro-6-(3-methyl-4-oxo-3,4-dihydroquinazolin-8-yl)-2-methylamino-6,7,7a,8,9,10-hexahydro-5H-pyrimido[5,4-f]pyrrolo[1,2-a][1,4]diazepin-5-one (Compound 116)

Compound 116 was obtained in the same manner as in Example 115 using (2S,4S)-1-(tert-butoxycarbonyl)-4-fluoropyrrolidine-2-carboxylic acid, instead of using (2S,4R)-1-(tert-butoxycarbonyl)-4-fluoropyrrolidine-2-carboxylic acid.

ESI-MS: m/z 410 [M+H]⁺. ¹H-NMR (CDCl₃) δ (ppm): 2.13 (m, 1H), 2.63 (m, 1H), 3.03 (s, 3H), 3.57 (s, 3H), 3.65-3.85 (m, 3H), 4.08 (m, 1H), 4.58 (m, 1H), 5.26 (br d, J=53.7 Hz, 1H), 5.44 (br s, 1H), 7.53 (dd, J=7.8, 7.8 Hz, 1H), 7.66 (dd, J=1.1, 7.8 Hz, 1H), 8.01 (s, 1H), 8.30 (dd, J=1.1, 7.8 Hz, 1H), 8.95 (s, 1H).

Example 117

(7aS,9S)-2-Ethylamino-9-methoxy-6-(3-methyl-4-oxo-3,4-dihydroquinazolin-8-yl)-6,7,7a,8,9,10-hexahydro-5H-pyrimido[5,4-f]pyrrolo[1,2-a][1,4]diazepin-5-one (Compound 117)

Step 1

Di-tert-butyl carbonate (15.8 g, 72.4 mmol) was dissolved in THF (40 mL), and commercially available (2S,4R)-4-hydroxypyrrolidine-2-carboxylic acid (10.0 g, 76.0 mmol) and a 10% sodium carbonate aqueous solution (80 mL) were added. The mixture was stirred at room temperature for 24 hours. The organic solvent was removed under reduced pressure, and washed with ethyl acetate. After adjusting the pH to 3 by adding 1 mol/L hydrochloric acid to the aqueous layer, the mixture was extracted once with ethyl acetate. The organic layer was dried over anhydrous magnesium sulfate, and concentrated under reduced pressure.

The obtained residue was dissolved in 2,2-dimethoxyethane (70 mL), and cooled to −20° C. Then, isobutyl chloroformate (9.51 mL, 72.4 mmol) and N-methylmorpholine (7.96 mL, 72.4 mmol) were added, and the mixture was stirred at −20° C. for 30 minutes. After removing the precipitate by filtration, the filtrate was cooled to 20° C., and a sodium borohydride (2.74 g, 72.4 mmol) aqueous solution (60 mL) was added. The mixture was stirred at −20° C. for 30 minutes. The reaction mixture was concentrated under reduced pressure, and then, after adding a 1 mol/L sodium hydroxide aqueous solution, extracted three times with ethyl acetate. The organic layer was dried over anhydrous magnesium sulfate, and concentrated under reduced pressure. The obtained residue was purified by silica gel column chromatography (ethyl acetate) to give (2S,4R)-tert-butyl 4-hydroxy-2-(hydroxymethyl)pyrrolidine-1-carboxylate (12.3 g, 78%).

ESI-MS: m/z 118 [M−Boc+H]⁺. ¹H-NMR (CDCl₃, 80° C.) δ (ppm): 1.43 (s, 9H), 1.66 (br m, 1H), 2.01 (m, 1H), 3.33-3.73 (m. 5H), 4.14 (m, 1H), 4.35 (br m, 1H), 5.25 (br d, J=6.5 Hz, 1H).

Step 2

(2S,4R)-tert-Butyl 4-hydroxy-2-(hydroxymethyl)pyrrolidine-1-carboxylate (3.0 g, 13.8 mmol) obtained in step 1 was dissolved in dichloromethane (70 mL), and tert-butyldimethylsilyl chloride (2.71 g, 18.0 mmol), triethylamine (2.50 mL, 18.0 mmol), and 4-dimethylaminopyridine (0.169 g, 1.38 mmol) were added. The mixture was stirred at room temperature for 24 hours. After concentrating the reaction mixture under reduced pressure, the obtained residue was purified by silica gel column chromatography (heptane/ethyl acetate=2/1) to give (2S,4R)-tert-butyl 2-((tert-butyldimethylsilyloxy)methyl)-4-hydroxypyrrolidine-1-carboxylate (3.52 g, 77%).

ESI-MS: m/z 232 [M−Boc+H]⁺. ¹H-NMR (CDCl₃, 80° C.) δ (ppm): 0.05 (s, 6H), 0.90 (s, 9H), 1.43 (br d, J=4.0 Hz, 1H), 1.48 (s, 9H), 1.96 (m, 1H), 2.22 (m, 1H), 3.45 (br d, J=3.7 Hz, 2H), 3.64 (br d, J=9.5 Hz, 1H), 3.84 (m, 1H), 4.00 (m, 1H), 4.46 (m, 1H).

Step 3

(2S,4R)-tert-Butyl 2-((tert-butyldimethylsilyloxy) methyl)-4-hydroxypyrrolidine-1-carboxylate (2.0 g, 6.03 mmol) obtained in step 2 was dissolved in DMF (30 mL), and the mixture was cooled to 0° C. Then, 60% sodium hydride (0.314 g, 7.84 mmol) was added, and the mixture was stirred at 0° C. for 20 minutes. After adding methyl iodide (0.745 mL, 12.1 mmol), the mixture was stirred at room temperature for 2.5 hours, and a saturated ammonium chloride aqueous solution was added. The mixture was diluted by adding ethyl acetate, and washed with water and saturated brine. The organic layer was dried over anhydrous magnesium sulfate, and concentrated under reduced pressure. The obtained residue was purified by silica gel column chromatography (heptane/ethyl acetate=10/1) to give (2S,4R)-tert-butyl 2-((tert-butyldimethylsilyloxy)methyl)-4-methoxypyrrolidine-1-carboxylate (1.96 g, 94%).

ESI-MS: m/z 246 [M−Boc+H]$^+$. $^1$H-NMR (CDCl$_3$, 80° C.) δ (ppm): 0.05 (s, 3H), 0.06 (s, 3H), 0.91 (s, 9H), 1.47 (s, 9H), 2.01 (m, 1H), 2.16 (m, 1H), 3.30 (s, 3H), 3.40 (dd, J=5.1, 11.4 Hz, 1H), 3.52 (br m, 1H), 3.63 (dd, J=2.6, 9.9 Hz, 1H), 3.80 (br s, 1H), 3.90-4.03 (m, 2H).

Step 4

(2S,4R)-tert-Butyl 2-((tert-butyldimethylsilyloxy) methyl)-4-methoxypyrrolidine-1-carboxylate (1.96 g, 5.67 mmol) obtained in step 3 was dissolved in THF (28 mL), and a 1.0 mol/L tetrabutylammonium fluoride/THF solution (11.3 mL, 11.3 mmol) was added. The mixture was stirred at room temperature for 1 hour. The reaction mixture was concentrated under reduced pressure, and the obtained residue was purified by silica gel column chromatography (heptane/ethyl acetate=1/1) to give (2S,4R)-tert-butyl 2-(hydroxymethyl)-4-methoxypyrrolidine-1-carboxylate (1.29 g, 98%).

ESI-MS: m/z 132 [M−Boc+H]$^+$.

$^1$H-NMR (CDCl$_3$, 80° C.) δ (ppm): 1.47 (s, 9H), 1.73 (m, 1H), 2.09 (m, 1H), 3.29 (s, 3H), 3.37 (dd, J=4.4, 11.7 Hz, 1H), 3.51-3.64 (m, 2H), 3.70 (dd, J=2.9, 11.7 Hz, 1H), 3.85 (m, 1H), 4.01 (m, 1H).

Step 5

Compound 117 was obtained in the same manner as in Example 115, using (2S,4R)-tert-butyl 2-(hydroxymethyl)-4-methoxypyrrolidine-1-carboxylate obtained in step 4.

ESI-MS: m/z 436 [M+H]$^+$. $^1$H-NMR (CDCl$_3$) δ (ppm): 1.25 (t, J=7.0 Hz, 3H), 1.67 (m, 1H), 2.24 (m, 1H), 3.38 (s, 3H), 3.57 (s, 3H), 3.42-3.54 (m, 2H), 3.67 (m, 1H), 3.84-4.03 (m, 4H), 4.49 (m, 1H), 5.14 (br s, 1H), 7.53 (dd, J=7.7, 7.7 Hz, 1H), 7.67 (dd, J=1.8, 7.7 Hz, 1H), 8.02 (s, 1H), 8.28 (dd, J=1.8, 7.7 Hz, 1H), 8.83 (s, 1H).

Example 118

(7aS,9R)-2-Ethylamino-9-hydroxy-6-(3-methyl-4-oxo-3,4-dihydroquinazolin-8-yl)-6,7,7a,8,9,10-hexahydro-5H-pyrimido[5,4-f]pyrrolo[1,2-a][1,4]diazepin-5-one (Compound 118)

Step 1

Commercially available (2S,4R)-1-(tert-butoxycarbonyl)-4-hydroxypyrrolidine-2-carboxylic acid (10 g, 43.2 mmol) was dissolved in DMF (108 mL), and cooled to 0° C. Then, potassium carbonate (17.9 g, 130 mmol) and methyl iodide (4.06 mL, 64.9 mmol) were added, and the mixture was stirred at room temperature for 5 hours. The reaction mixture was diluted with ethyl acetate, and washed with water and saturated brine. The organic layer was dried over anhydrous magnesium sulfate, and concentrated under reduced pressure.

The obtained residue was dissolved in DMF (108 mL), and tert-butyldimethylsilyl chloride (13.0 g, 80.0 mmol) and imidazole (11.8 g, 173 mmol) were added at 0° C. The mixture was stirred at room temperature for 2 hours. The reaction mixture was diluted with ethyl acetate, and washed with water and saturated brine. The organic layer was dried over anhydrous magnesium sulfate, and concentrated under reduced pressure. The obtained residue was purified by silica gel column chromatography (heptane/ethyl acetate=5/1) to give (2S,4R)-1-tert-butyl 2-methyl-4-(tert-butyldimethylsilyloxy)pyrrolidine-1,2-dicarboxylate (15.3 g, 98%).

$^1$H-NMR (CDCl$_3$) δ (ppm): 0.07 (s, 6H), 0.88 (s, 9H), 1.43 (s, 9H), 2.03 (m, 1H), 2.17 (m, 1H), 3.38 (br d, J=11.0 Hz, 1H), 3.60 (dd, J=5.1, 11.4 Hz, 1H), 3.72 (s, 3H), 4.33-4.46 (m, 2H).

Step 2

Lithium aluminum hydride (0.739 g, 19.5 mmol) was dissolved in THF (60 mL), and cooled to 0° C. Then, a THF solution (30 mL) of (2S,4R)-1-tert-butyl 2-methyl-4-(tert-butyldimethylsilyloxy)pyrrolidine-1,2-dicarboxylate (7.0 g, 19.5 mmol) obtained in step 1 was added, and the mixture was stirred at room temperature for 40 minutes. The reaction mixture was extracted twice with ethyl acetate after adding a 2 mol/L sodium hydroxide aqueous solution. The organic layer was washed with saturated brine, dried over anhydrous magnesium sulfate, and concentrated under reduced pressure. The obtained residue was purified by silica gel column chromatography (heptane/ethyl acetate=5/1) to give (2S,4R)-1-tert-butyl 4-(tert-butyldimethylsilyloxy)-2-(hydroxymethyl)pyrrolidine-1,2-dicarboxylate (4.62 g, 72%).

$^1$H-NMR (CDCl$_3$) δ (ppm): 0.08 (s, 6H), 0.90 (s, 9H), 1.48 (s, 9H), 1.71 (m, 1H), 1.96 (m, 1H), 3.36 (dd, J=4.4, 11.4 Hz, 1H), 3.46 (br d, J=11.3 Hz, 1H), 3.55 (m, 1H), 3.70 (m, 1H), 4.09 (m, 1H), 4.31 (m, 1H).

Step 3

(2S,4R)-1-tert-Butyl 4-(tert-butyldimethylsilyloxy)-2-(hydroxymethyl)pyrrolidine-1,2-dicarboxylate (5.29 g, 16.0 mmol) obtained in step 2 was dissolved in toluene (80 mL), and N-tert-butyloxycarbonyl-2-nitrobenzenesulfonamide (7.24 g, 23.9 mmol), triphenylphosphine (6.28 g, 23.9 mmol), and a 40% diethylazodicarboxylate/toluene solution (9.47 mL, 23.9 mmol) were added. The mixture was stirred at 65° C. for 1 hour. After cooling the reaction mixture to room temperature, the precipitate was removed by filtration. After adding a 2 mol/L sodium hydroxide aqueous solution to the filtrate, the mixture was extracted with toluene, and washed with saturated brine. The organic layer was dried over anhydrous magnesium sulfate, and concentrated under reduced pressure. The obtained residue was purified by silica gel column chromatography (heptane/ethyl acetate=3/1).

The resulting product was dissolved in ethyl acetate (20 mL), and a 4 mol/L hydrogen chloride/1,4-dioxane solution (40 mL) was added. The mixture was stirred at room temperature for 1.5 hours. The precipitated crystals were collected by filtration to give N-(((2S,4R)-4-hydroxypyrrolidin-2-yl)methyl)-2-nitrobenzenesulfonamide (1.58 g, 29%).

ESI-MS: m/z 338 [M+H]$^+$. $^1$H-NMR (DMSO-d$_6$) δ (ppm): 1.79 (m, 1H), 1.98 (m, 1H), 3.03 (m, 1H), 3.33 (m, 3H), 3.82 (m, 1H), 4.39 (m, 1H), 7.83-7.98 (m, 3H), 8.09 (m, 1H), 8.37 (br s, 1H), 9.38 (br s, 1H).

Step 4

N-(((2S,4R)-4-Hydroxypyrrolidin-2-yl)methyl)-2-nitrobenzenesulfonamide (1.58 g, 4.68 mmol) obtained in step 3 was dissolved in 1,4-dioxane (31 mL), and ethyl 4-chloro-2-methylthiopyrimidine-5-carboxylate (2.18 g, 9.36 mmol) and N,N-diisopropylethylamine (3.27 mL, 18.7 mmol) were added. The mixture was stirred at 90° C. for 1.5 hours. The reaction mixture was cooled to room temperature, diluted with ethyl acetate, and washed with water and saturated brine. The organic layer was dried over anhydrous magnesium sulfate, and concentrated under reduced pressure. The obtained residue was purified by silica gel column chromatography (heptane/ethyl acetate=1/4) to give ethyl 4-((2S,4R)-4-hydroxy-2-((2-nitrophenylsulfonamido)methyl)pyrrolidin-1-yl)-2-(methylthio)pyrimidine-5-carboxylate (2.22 g, quant.).

ESI-MS: m/z 498 [M+H]$^+$. $^1$H-NMR (CDCl$_3$, 80° C.) δ (ppm): 1.36 (t, J=7.3 Hz, 3H), 2.19 (m, 1H), 2.44 (s, 3H), 2.45 (m, 1H), 2.85 (br dd, J=1.8, 12.8 Hz, 1H), 3.45-3.61 (m, 2H), 3.80 (dd, J=3.3, 12.5 Hz, 1H), 4.26-4.36 (m, 2H), 4.49 (br s, 1H), 4.88 (m, 1H), 5.75 (m, 1H), 7.65-7.72 (m, 2H), 7.79 (m, 1H), 8.06 (m, 1H), 8.41 (s, 1H).

Step 5

Ethyl 4-((2S,4R)-4-hydroxy-2-((2-nitrophenylsulfonamido)methyl)pyrrolidin-1-yl)-2-(methylthio)pyrimidine-5-carboxylate (2.15 g, 4.32 mmol) obtained in step 4 was dissolved in DMF (43 mL), and tert-butyldimethylsilyl chloride (1.30 g, 8.64 mmol) and imidazole (1.18 g, 17.3 mmol) were added at 0° C. The mixture was stirred at room temperature for 1.5 hours. The reaction mixture was diluted with ethyl acetate, washed with water and saturated brine, dried over anhydrous magnesium sulfate, and concentrated under reduced pressure. The obtained residue was purified by silica gel column chromatography (heptane/ethyl acetate=1/1) to give ethyl 4-((2S,4R)-4-(tert-butyldimethylsilyloxy)-2-((2-nitrophenylsulfonamido)methyl)pyrrolidin-1-yl)-2-(methylthio)pyrimidine-5-carboxylate (2.51 g, 95%).

ESI-MS: m/z 612 [M+H]$^+$. $^1$H-NMR (CDCl$_3$, 80° C.) δ (ppm): 0.02 (s, 3H), 0.05 (s, 3H), 0.74 (s, 9H), 1.37 (t, J=7.3 Hz, 3H), 2.07-2.12 (m, 2H), 2.47 (s, 3H), 2.72 (d, J=12.1 Hz, 1H), 3.45-3.61 (m, 2H), 3.74 (dd, J=3.3, 11.7 Hz, 1H), 4.28-4.43 (m, 3H), 4.79 (m, 1H), 5.71 (m, 1H), 7.65-7.73 (m, 2H), 7.79 (m, 1H), 8.08 (m, 1H), 8.49 (s, 1H).

Step 6

Ethyl 4-((2S,4R)-4-(tert-butyldimethylsilyloxy)-2-((2-nitrophenylsulfonamido)methyl)pyrrolidin-1-yl)-2-(methylthio)pyrimidine-5-carboxylate (2.51 g, 4.10 mmol) obtained in step 5 was dissolved in ethanol (27 mL), and mercaptoacetic acid (0.855 mL, 12.3 mmol) and DBU (3.71 mL, 24.6 mmol) were added. The mixture was stirred at 70° C. for 1.5 hours. The reaction mixture was concentrated under reduced pressure, diluted with ethyl acetate, and washed with a saturated sodium bicarbonate aqueous solution, water, and saturated brine. The organic layer was dried over anhydrous magnesium sulfate, and concentrated under reduced pressure. The obtained residue was purified by silica gel column chromatography (ethyl acetate) to give (7aS,9R)-9-(tert-butyldimethylsiloxy)-2-methylthio-6,7,7a,8,9,10-hexahydro-5H-pyrimido[5,4-f]pyrrolo[1,2-a][1,4]diazepin-5-one (1.37 g, 88%).

ESI-MS: m/z 381 [M+H]$^+$. $^1$H-NMR (CDCl$_3$, 80° C.) δ (ppm): 0.08 (s, 3H), 0.09 (s, 3H), 0.87 (s, 9H), 1.73 (m, 1H), 2.10 (m, 1H), 2.52 (s, 3H), 3.29 (ddd, J=3.7, 8.1, 14.7 Hz, 1H), 3.51 (dd, J=8.1, 14.7 Hz, 1H), 3.69 (dd, J=1.5, 13.2 Hz, 1H), 3.93 (dd, J=4.0, 13.6 Hz, 1H), 4.16 (m, 1H), 4.42 (t, J=3.3 Hz, 1H), 7.63 (br s, 1H), 8.83 (s, 1H).

Step 7

A Compound obtained in the same manner as in step 1 of Example 34 using (7aS,9R)-9-(tert-butyldimethylsiloxy)-2-methylthio-6,7,7a,8,9,10-hexahydro-5H-pyrimido[5,4-f]pyrrolo[1,2-a][1,4]diazepin-5-one obtained in step 6 and Compound e obtained in Reference Example 5 was treated with a 1.0 mol/L tetrabutylammonium fluoride/THF solution, then Compound 118 was obtained in the same manner as in step 2 of Example 34, and Example 35.

ESI-MS: m/z 422 [M+H]$^+$. $^1$H-NMR (CDCl$_3$, 80° C.) δ (ppm): 1.25 (t, J=7.3 Hz, 3H), 1.72 (m, 1H), 2.02 (m, 1H), 3.37-3.51 (m, 3H), 3.53 (s, 3H), 3.65 (m, 1H), 3.79 (m, 1H), 3.90-4.06 (m, 1H), 4.51 (m, 1H), 4.66 (m, 1H), 5.60 (br s, 1H), 7.47 (dd, J=7.8, 7.8 Hz, 1H), 7.66 (d, J=7.8 Hz, 1H), 7.97 (s, 1H), 8.26 (d, J=7.8 Hz, 1H), 8.82 (s, 1H).

Example 119

(7aS,9S)-2-Ethylamino-9-hydroxy-6-(3-methyl-4-oxo-3,4-dihydroquinazolin-8-yl)-6,7,7a,8,9,10-hexahydro-5H-pyrimido[5,4-f]pyrrolo[1,2-a][1,4]diazepin-5-one (Compound 119)

Step 1

A Compound obtained in the same manner as in step 1 of Example 34 using (7aS,9R)-9-(tert-butyldimethylsiloxy)-2-methylthio-6,7,7a,8,9,10-hexahydro-5H-pyrimido[5,4-f]pyrrolo[1,2-a][1,4]diazepin-5-one obtained in step 6 of Example 118 and Compound e obtained in Reference Example 5 was dissolved in THF (10 mL). Then, 4-nitrobenzoic acid (252 mg, 1.51 mmol), triphenylphosphine (395 mg, 1.51 mmol), and a 40% diethylazodicarboxylate/toluene solution (0.685 mL, 1.51 mmol) were added, and the mixture was stirred at 60° C. for 1 hour. The reaction mixture was concentrated under reduced pressure, diluted with chloroform, and washed with a 2 mol/L sodium hydroxide aqueous solution. The organic layer was dried over anhydrous magnesium sulfate, and concentrated under reduced pressure. The obtained residue was purified by silica gel column chromatography (ethyl acetate) to give (7aS,9S)-6-(3-methyl-4-oxo-3,4-dihydroquinazolin-8-yl)-2-methylthio-9-(4-nitrobenzoyloxy)-6,7,7a,8,9,10-hexahydro-5H-pyrimido[5,4-f]pyrrolo[1,2-a][1,4]diazepin-5-one (397 mg, 73%).

ESI-MS: m/z 574 [M+H]$^+$. $^1$H-NMR (CDCl$_3$) δ: 2.08 (m, 1H), 2.59 (s, 3H), 2.77 (m, 1H), 3.60 (s, 3H), 3.79 (d, J=15.0 Hz, 1H), 4.06-4.38 (m, 4H), 5.65 (m, 1H), 7.56 (dd, J=7.7, 7.7 Hz, 1H), 7.71 (dd, J=1.5, 7.7 Hz, 1H), 8.04 (s, 1H), 8.19-8.37 (m, 4H), 8.98 (s, 1H).

Step 2

(7aS,9S)-6-(3-Methyl-4-oxo-3,4-dihydroquinazolin-8-yl)-2-methylthio-9-(4-nitrobenzoyloxy)-6,7,7a,8,9,10-hexahydro-5H-pyrimido[5,4-f]pyrrolo[1,2-a][1,4]diazepin-5-one (947 mg, 1.65 mmol) obtained in step 1 was dissolved in methanol (8.2 mL), and a 1 mol/L sodium hydroxide aqueous solution (3.3 mL, 3.3 mmol) was added. The mixture was stirred at room temperature for 5 hours. The reaction mixture was concentrated under reduced pressure, diluted with chloroform, and washed with water and saturated brine. The organic layer was dried over anhydrous magnesium sulfate, and concentrated under reduced pressure. The obtained residue was purified by silica gel column chromatography (chloroform/methanol=10/1) to give (7aS,9S)-9-hydroxy-6-(3-methyl-4-oxo-3,4-dihydroquinazolin-8-yl)-2-methylthio-6,7,7a,8,9,10-hexahydro-5H-pyrimido[5,4-f]pyrrolo[1,2-a][1,4]diazepin-5-one (317 mg, 45%).

ESI-MS: m/z 425 [M+H]⁺. ¹H-NMR (CDCl₃, 80° C.) δ: 1.79 (m, 1H), 2.49 (m, 1H), 2.58 (s, 3H), 3.55 (s, 3H), 3.68 (d, J=15.0 Hz, 1H), 3.90-4.14 (m, 3H), 4.42-4.59 (m, 2H), 7.51 (dd, J=7.3, 7.7 Hz, 1H), 7.65 (dd, J=1.5, 7.3 Hz, 1H), 7.97 (s, 1H), 8.30 (dd, J=1.5, 7.7 Hz, 1H), 8.95 (s, 1H).

Step 3

Compound 119 was obtained in the same manner as in step 2 of Example 34, and Example 35, using (7aS,9S)-9-hydroxy-6-(3-methyl-4-oxo-3,4-dihydroquinazolin-8-yl)-2-methylthio-6,7,7a,8,9,10-hexahydro-5H-pyrimido[5,4-f]pyrrolo[1,2-a][1,4]diazepin-5-one obtained in step 2.

ESI-MS: m/z 422 [M+H]⁺. ¹H-NMR (CDCl₃) δ (ppm): 1.24 (t, J=7.8 Hz, 3H), 1.76 (m, 1H), 2.41 (m, 1H), 3.42-3.50 (m, 3H), 3.58 (s, 3H), 3.63 (d, J=15.0 Hz, 1H), 3.79-4.13 (m, 3H), 4.47 (m, 1H), 5.41 (br s, 1H), 7.53 (dd, J=7.8, 7.8 Hz, 1H), 7.65 (d, J=7.8 Hz, 1H), 8.04 (s, 1H), 8.28 (d, J=7.8 Hz, 1H), 8.79 (s, 1H).

Example 120

(7aS,9S)-2-Ethylamino-9-methoxy-6-(3-methyl-4-oxo-3,4-dihydroquinazolin-8-yl)-6,7,7a,8,9,10-hexahydro-5H-pyrimido[5,4-f]pyrrolo[1,2-a][1,4]diazepin-5-one (Compound 120)

Step 1

(7aS,9S)-9-Hydroxy-6-(3-methyl-4-oxo-3,4-dihydroquinazolin-8-yl)-2-methylthio-6,7,7a,8,9,10-hexahydro-5H-pyrimido[5,4-f]pyrrolo[1,2-a][1,4]diazepin-5-one (113 mg, 0.266 mmol) obtained in step 2 of Example 119 was dissolved in DMF (2.7 mL), and 60% sodium hydride (13.0 mg, 0.319 mmol) was added at 0° C. The mixture was stirred at 0° C. for 15 minutes. After adding methyl iodide (0.050 mL, 0.319 mmol), the mixture was stirred at room temperature for 6 hours. After adding a saturated ammonium chloride aqueous solution, the reaction mixture was diluted with ethyl acetate, and washed with water and saturated brine. The organic layer was dried over anhydrous magnesium sulfate, and concentrated under reduced pressure. The obtained residue was purified by silica gel column chromatography (chloroform/methanol=20/1) to give (7aS,9S)-9-methoxy-6-(3-methyl-4-oxo-3,4-dihydroquinazolin-8-yl)-2-methylthio-6,7,7a,8,9,10-hexahydro-5H-pyrimido[5,4-f]pyrrolo[1,2-a][1,4]diazepin-5-one (45.0 mg, 39%).

ESI-MS: m/z 439 [M+H]⁺. ¹H-NMR (CDCl₃) δ (ppm): 1.78 (m, 1H), 2.49 (m, 1H), 2.56 (s, 3H), 3.39 (s, 3H), 3.56 (s, 3H), 3.66 (d, J=14.6 Hz, 1H), 3.92 (m, 1H), 4.00-4.14 (m, 4H), 7.53 (dd, J=7.8, 7.8 Hz, 1H), 7.66 (dd, J=1.9, 7.8 Hz, 1H), 8.00 (s, 1H), 8.31 (dd, J=1.9, 7.7 Hz, 1H), 8.93 (s, 1H).

Step 2

Compound 120 was obtained in the same manner as in step 2 of Example 34, and Example 35, using (7aS,9S)-9-methoxy-6-(3-methyl-4-oxo-3,4-dihydroquinazolin-8-yl)-2-methylthio-6,7,7a,8,9,10-hexahydro-5H-pyrimido[5,4-f]pyrrolo[1,2-a][1,4]diazepin-5-one (27.0 mg, 0.062 mmol) obtained in step 1.

ESI-MS: m/z 436 [M+H]⁺. ¹H-NMR (CDCl₃) δ (ppm): 1.24 (d, J=6.8 Hz, 3H), 1.75 (m, 1H), 2.46 (m, 1H), 3.39 (s, 3H), 3.44-3.51 (m, 2H), 3.57 (s, 3H), 3.63 (d, J=14.6 Hz, 1H), 3.86-4.10 (m, 4H), 4.39 (m, 1H), 5.14 (br s, 1H), 7.52 (dd, J=7.8, 7.8 Hz, 1H), 7.65 (dd, J=1.9, 7.8 Hz, 1H), 8.01 (s, 1H), 8.29 (dd, J=1.9, 7.8 Hz, 1H), 8.86 (s, 1H).

Example 121

Tablet (Compound 39)

Tablets having the following ingredients are prepared according to the conventional method. Compound 39 (40 g), lactose (286.8 g), and potato starch (60 g) are mixed, and a 10% aqueous solution of hydroxypropylcellulose (120 g) is added thereto. The resulting mixture is kneaded by using a conventional method, granulated and dried, and sized to form tableting granules. Magnesium stearate (1.2 g) is added and mixed with the tableting granules, and the mixture is tableted using a tableting machine with a pestle having a diameter of 8-mm (Kikusui, Model RT-15) (containing 20 mg of active ingredient per tablet).

TABLE 14

| Formulation | |
|---|---|
| Compound 39 | 20 mg |
| lactose | 143.4 mg |
| potato starch | 30 mg |
| hydroxypropylcellulose | 6 mg |
| magnesium stearate | 0.6 mg |
| | 200 mg |

INDUSTRIAL APPLICABILITY

Compound (I) has affinity for α₂δ protein, and can be used as a therapeutic and/or preventive agent for diseases such as pain (for example, neuropathic pain, trigeminal neuralgia, diabetic pain, postherpetic neuralgia, phantom pain, neuropathic lower back pain, HIV-related pain, fibromyalgia syndrome, cancer pain, inflammatory pain, acute pain, chronic pain, postoperative pain, pain after teeth extraction, chronic musculoskeletal pain, nociceptive pain, psychogenic pain, menstrual pain, and the like), migraine, pruritus, lower urinary tract symptoms, irritable bowel syndrome, epilepsy, restless legs syndrome, hot flash, mood disorder, and sleep disorder, and the like.

The invention claimed is:

1. A compound represented by formula (I), or a pharmaceutically acceptable salt thereof,

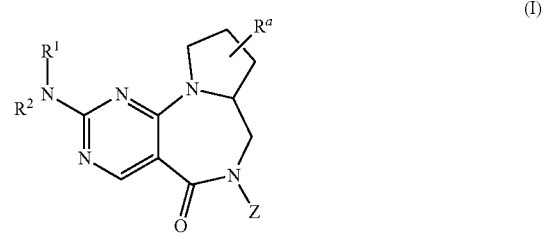

wherein $R^a$ represents a hydrogen atom, halogen, hydroxy, or lower alkoxy, $R^1$ and $R^2$ may be the same or different, and each represents a hydrogen atom, optionally substituted lower alkyl or cycloalkyl, or $R^1$ and $R^2$ are combined together with the adjacent nitrogen atom thereto to form a nitrogen-containing heterocyclic group, and Z represents a bicyclic heterocyclic group in which optionally substituted two six-membered rings are fused to each other.

2. The compound or the pharmaceutically acceptable salt thereof according to claim 1, wherein $R^a$ is a hydrogen atom.

3. The compound or the pharmaceutically acceptable salt thereof according to claim 1, wherein the bicyclic heterocyclic ring moiety of the bicyclic heterocyclic group in which two six-membered rings are fused to each other is a heterocyclic ring represented by any one of the following formulae (A) to (R)

4. The compound or the pharmaceutically acceptable salt thereof according to claim 1, wherein the bicyclic heterocyclic ring moiety of the bicyclic heterocyclic group in which two six-membered rings are fused to each other is a heterocyclic ring represented by the following formula (A), (B), (D), (E), (J), or (L)

5. The compound or the pharmaceutically acceptable salt thereof according to claim 1, wherein the bicyclic heterocyclic ring moiety of the bicyclic heterocyclic group in which two six-membered rings are fused to each other is a heterocyclic ring represented by the following formula (E), (J), or (L)

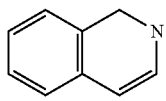
(E)

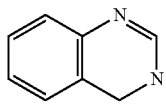
(J)

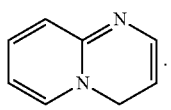
(L)

6. The compound or the pharmaceutically acceptable salt thereof according to claim 1, wherein the bicyclic heterocyclic group in which two six-membered rings are fused to each other is a group represented by the following formula (A1), (A2), (B1), (B2), (D1), (D2), (E1), (E2), (J1), (J2), (L1), or (L2)

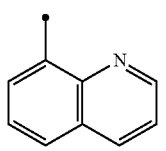
(A1)

(A2)

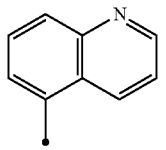
(B1)

(B2)

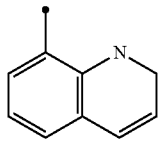
(D1)

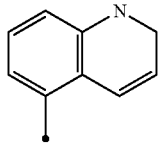
(D2)

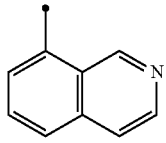

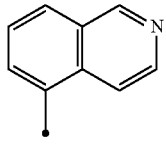

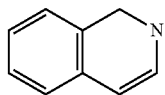
(E1)

(E2)

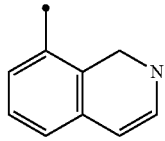
(J1)

(J2)

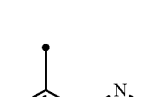
(L1)

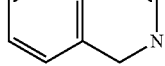
(L2)

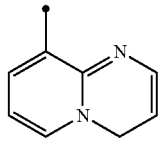

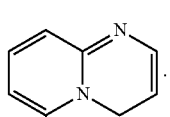

7. The compound or the pharmaceutically acceptable salt thereof according to claim 1, wherein the bicyclic heterocyclic group in which optionally substituted two six-membered rings are fused to each other is a group represented by the following formula (L1a), (J1a), (J2a), or (E1a),

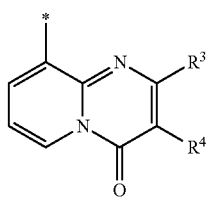
(L1a)

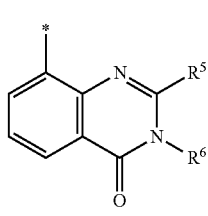
(J1a)

-continued

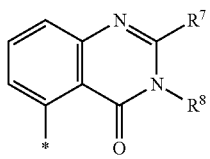
(J2a)

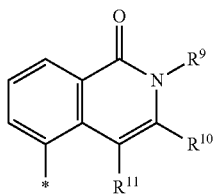
(E1a)

wherein R³, R⁴, R⁵, R⁶, R⁷, R⁸, R⁹, R¹⁰, and R¹¹ may be the same or different, and each represents a hydrogen atom, or optionally substituted lower alkyl.

8. The compound or the pharmaceutically acceptable salt thereof according to claim 1, wherein the bicyclic heterocyclic group in which optionally substituted two six-membered rings are fused to each other is a group represented by the following formula (L1a) or (J1a),

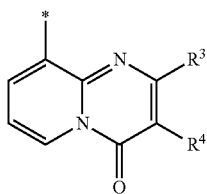
(L1a)

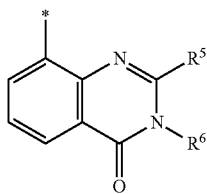
(J1a)

wherein R³, R⁴, R⁵, and R⁶ may be the same or different, and each represents a hydrogen atom, or optionally substituted lower alkyl.

9. The compound or the pharmaceutically acceptable salt thereof according to claim 1, wherein R¹ is lower alkyl or cycloalkyl, and R² is a hydrogen atom.

10. The compound or the pharmaceutically acceptable salt thereof according to claim 1, wherein R¹ is lower alkyl, and R² is a hydrogen atom.

11. The compound or the pharmaceutically acceptable salt thereof according to claim 1, wherein the compound represented by formula (I) is selected from the group consisting of:

(S)-6-(2,3-dimethyl-4-oxo-4H-pyrido[1,2-a]pyrimidin-9-yl)-2-ethylamino-6,7,7a,8,9,10-hexahydro-5H-pyrimido[5,4-f]pyrrolo[1,2-a][1,4]diazepin-5-one (compound 7), (S)-6-(2,3-dimethyl-4-oxo-4H-pyrido[1,2-a]pyrimidin-9-yl)-2-methylamino-6,7,7a,8,9,10-hexahydro-5H-pyrimido[5,4-f]pyrrolo[1,2-a][1,4]diazepin-5-one (compound 8), (S)-6-(3-methyl-4-oxo-3,4-dihydroquinazolin-8-yl)-2-methylamino-6,7,7a,8,9,10-hexahydro-5H-pyrimido[5,4-f]pyrrolo[1,2-a][1,4]diazepin-5-one (compound 10), (S)-2-ethylamino-6-(2,3-dimethyl-4-oxo-3,4-dihydroquinazolin-8-yl)-6,7,7a,8,9,10-hexahydro-5H-pyrimido[5,4-f]pyrrolo[1,2-a][1,4]diazepin-5-one (compound 11), (S)-6-(3-ethyl-4-oxo-3,4-dihydroquinazolin-8-yl)-2-methylamino-6,7,7a,8,9,10-hexahydro-5H-pyrimido[5,4-f]pyrrolo[1,2-a][1,4]diazepin-5-one (compound 14), (S)-2-ethylamino-6-(3-methyl-4-oxo-3,4-dihydroquinazolin-5-yl)-6,7,7a,8,9,10-hexahydro-5H-pyrimido[5,4-f]pyrrolo[1,2-a][1,4]diazepin-5-one (compound 15), (S)-6-(3-(3-(dimethylamino)propyl)-4-oxo-3,4-dihydroquinazolin-8-yl)-2-(methylamino)-6,7,7a,8,9,10-hexahydro-5H-pyrimido[5,4-f]pyrrolo[1,2-a][1,4]diazepin-5-one (compound 38), (S)-6-(3-(3-(dimethylamino)propyl)-4-oxo-3,4-dihydroquinazolin-8-yl)-2-(ethylamino)-6,7,7a,8,9,10-hexahydro-5H-pyrimido[5,4-f]pyrrolo[1,2-a][1,4]diazepin-5-one (compound 39), (S)-2-ethylamino-6-(2-(methoxymethyl)-3-methyl-4-oxo-3,4-dihydroquinazolin-8-yl)-6,7,7a,8,9,10-hexahydro-5H-pyrimido[5,4-f]pyrrolo[1,2-a][1,4]diazepin-5-one (compound 65), and (S)-6-(3-methyl-4-oxo-3,4-dihydroquinazolin-8-yl)-2-propylamino-6,7,7a,8,9,10-hexahydro-5H-pyrimido[5,4-f]pyrrolo[1,2-a][1,4]diazepin-5-one (compound 71).

12. A method of treating diabetic pain, which comprises administering an effective amount of the compound or the pharmaceutically acceptable salt thereof according to claim 1.

13. A method of treating pain, which comprises administering an effective amount of the compound or the pharmaceutically acceptable salt thereof according to claim 1.

* * * * *

UNITED STATES PATENT AND TRADEMARK OFFICE
CERTIFICATE OF CORRECTION

PATENT NO. : 9,453,021 B2
APPLICATION NO. : 14/116702
DATED : September 27, 2016
INVENTOR(S) : Nobumasa Otsubo et al.

It is certified that error appears in the above-identified patent and that said Letters Patent is hereby corrected as shown below:

On the Title Page

After item "(75) Inventors:" remove "Shuko Okazaki, Tokyo (JP)" and "Kyoichiro Iida, Kanagawa (JP)".

Signed and Sealed this
Seventh Day of November, 2017

Joseph Matal
*Performing the Functions and Duties of the*
*Under Secretary of Commerce for Intellectual Property and*
*Director of the United States Patent and Trademark Office*